(12) United States Patent
Storer et al.

(10) Patent No.: US 9,067,922 B2
(45) Date of Patent: Jun. 30, 2015

(54) CHEMICAL COMPOUNDS

(71) Applicant: Pfizer Limited, Sandwich, Kent (GB)

(72) Inventors: Robert Ian Storer, Great Abington (GB); Nigel Alan Swain, Great Abington (GB); Robert McKenzie Owen, Great Abington (GB)

(73) Assignee: Pfizer Limited, Sandwich, Kent (GB)

( * ) Notice: Subject to any disclaimer, the term of this patent is extended or adjusted under 35 U.S.C. 154(b) by 0 days.

(21) Appl. No.: 14/254,988

(22) Filed: Apr. 17, 2014

(65) Prior Publication Data

US 2014/0315878 A1 Oct. 23, 2014

Related U.S. Application Data

(60) Provisional application No. 61/917,532, filed on Dec. 18, 2013, provisional application No. 61/813,809, filed on Apr. 19, 2013.

(51) Int. Cl.

| | | |
|---|---|---|
| *A61K 31/50* | (2006.01) | |
| *C07D 213/76* | (2006.01) | |
| *C07D 401/14* | (2006.01) | |
| *A61K 31/505* | (2006.01) | |
| *A61K 31/444* | (2006.01) | |
| *A61K 31/44* | (2006.01) | |
| *C07D 237/20* | (2006.01) | |
| *C07D 239/42* | (2006.01) | |
| *C07D 401/12* | (2006.01) | |
| *C07D 213/75* | (2006.01) | |
| *C07D 241/22* | (2006.01) | |

(52) U.S. Cl.
CPC .............. *C07D 401/14* (2013.01); *A61K 31/50* (2013.01); *A61K 31/505* (2013.01); *A61K 31/444* (2013.01); *A61K 31/44* (2013.01); *C07D 237/20* (2013.01); *C07D 239/42* (2013.01); *C07D 401/12* (2013.01); *C07D 213/76* (2013.01); *C07D 213/75* (2013.01); *C07D 241/22* (2013.01)

(58) Field of Classification Search
CPC ..... A61K 31/50; A61K 31/505; A61K 31/44; A61K 31/444; C07D 213/75; C07D 213/76; C07D 241/22; C07D 237/20; C07D 239/42; C07D 401/14; C07D 401/12
USPC ........................................................ 546/290
See application file for complete search history.

(56) References Cited

U.S. PATENT DOCUMENTS

| | | | |
|---|---|---|---|
| 5,571,821 A | 11/1996 | Chan et al. | |
| 5,607,954 A | 3/1997 | Weidmann et al. | |
| 8,153,814 B2 * | 4/2012 | Beaudoin et al. | 548/190 |
| 8,541,588 B2 * | 9/2013 | Beaudoin et al. | 546/290 |
| 2002/0045751 A1 | 4/2002 | Kukkola | |
| 2002/0107390 A1 | 8/2002 | Kukkola | |
| 2005/0245535 A1 | 11/2005 | Hangeland et al. | |
| 2009/0281089 A1 | 11/2009 | Gunzner et al. | |
| 2010/0029753 A1 | 2/2010 | Anderson et al. | |
| 2010/0197655 A1 | 8/2010 | Beaudoin et al. | |

FOREIGN PATENT DOCUMENTS

| | | |
|---|---|---|
| CN | 102206172 | 10/2011 |
| DE | 3737748 | 5/1989 |
| EP | 0104483 | 4/1984 |
| EP | 0472053 | 2/1992 |
| EP | 0532239 | 3/1993 |
| EP | 0569193 | 11/1993 |
| EP | 0590520 | 4/1994 |
| EP | 0768305 | 10/1995 |
| EP | 0682016 | 11/1995 |
| EP | 1541563 | 1/2004 |
| GB | 2295616 | 6/1996 |
| JP | 58124758 | 1/1982 |
| JP | 2064538 | 8/1988 |
| JP | 2000159665 | 11/1998 |
| JP | 2003292485 | 4/2002 |
| WO | 9427979 | 12/1994 |
| WO | 9526957 | 10/1995 |
| WO | 9938845 | 8/1999 |

(Continued)

OTHER PUBLICATIONS

Rozze, S.J., et al., "Unusual base-catalyzed exchange in the synthesis of deuterated PF-2413873a", Journal of Labelled Compounds and Radiopharmaceutical, 2009, pp. 435-442, 52(10).
French, F.A., et al., "α-(N)-Formylheteroaromatic Thiosemicarbazones. Inhibition of Tumor-Derived Ribonucleoside Diphosphate Reductase and Correlation with in Vivo Antitumor Activity", Journal of Medicinal Chemistry, 1974 pp. 172-181, 17(2).
International Search Report and Written Opinion, mailed Jun. 6, 2014 for PCT Application No. PCT/IB2014/060494, filed Apr. 7, 2014, 10 pages.
Johnson, S.L, et al., "Structure-activity relationship studies of a novel series of anthrax lethal factor inhibitors", Bioorganic & Medicinal Chemistry, May 1, 2009, pp. 3352-3368, 17(9).

(Continued)

*Primary Examiner* — D M Seaman
(74) *Attorney, Agent, or Firm* — Richard V. Zanzalari

(57) ABSTRACT

The present invention relates to new sulfonamide URAT-1 inhibitor compounds of formula (I) or a pharmaceutically acceptable salt thereof:

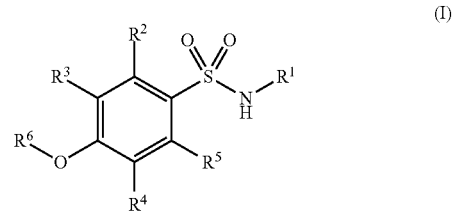

(I)

to compositions containing them, to processes for their preparation and to intermediates used in such processes, and to methods of treatment, wherein $R^1$, $R^2$, $R^3$, $R^4$, $R^5$ and $R^6$ are as defined in the description.

16 Claims, 8 Drawing Sheets

(56) References Cited

FOREIGN PATENT DOCUMENTS

| WO | 0058279 | 10/2000 |
|---|---|---|
| WO | 0112611 | 2/2001 |
| WO | 0123347 | 4/2001 |
| WO | 2011159840 | 5/2001 |
| WO | 0149289 | 7/2001 |
| WO | 0190090 | 11/2001 |
| WO | 0190091 | 11/2001 |
| WO | 0190092 | 11/2001 |
| WO | 0190093 | 11/2001 |
| WO | 0190094 | 11/2001 |
| WO | 0200647 | 1/2002 |
| WO | 0234726 | 5/2002 |
| WO | 02051397 | 7/2002 |
| WO | 02062750 | 8/2002 |
| WO | 02092606 | 11/2002 |
| WO | 03043999 | 5/2003 |
| WO | 03044000 | 5/2003 |
| WO | 03044009 | 5/2003 |
| WO | 03079986 | 10/2003 |
| WO | 2004011443 | 2/2004 |
| WO | 2004014825 | 2/2004 |
| WO | 2004021997 | 3/2004 |
| WO | 2004084898 | 10/2004 |
| WO | 2004103980 | 12/2004 |
| WO | 2004112781 | 12/2004 |
| WO | 2004112782 | 12/2004 |
| WO | 2004112784 | 12/2004 |
| WO | 2004113310 | 12/2004 |
| WO | 2004121779 | 12/2004 |
| WO | 2005000309 | 1/2005 |
| WO | 2005007621 | 1/2005 |
| WO | 2005054176 | 6/2005 |
| WO | 2005060963 | 7/2005 |
| WO | 2005086904 | 9/2005 |
| WO | 2005097764 | 10/2005 |
| WO | 2006000371 | 1/2006 |
| WO | 2006022374 | 3/2006 |
| WO | 2006024823 | 3/2006 |
| WO | 2006037501 | 4/2006 |
| WO | 2006042638 | 4/2006 |
| WO | 2006048331 | 5/2006 |
| WO | 2006050908 | 5/2006 |
| WO | 2006051662 | 5/2006 |
| WO | 2006060762 | 6/2006 |
| WO | 2006066109 | 6/2006 |
| WO | 2007003934 | 1/2007 |
| WO | 2007008541 | 1/2007 |
| WO | 2007034312 | 3/2007 |
| WO | 2007044565 | 4/2007 |
| WO | 2007067993 | 6/2007 |
| WO | 2007067994 | 6/2007 |
| WO | 2007071440 | 6/2007 |
| WO | 2007118859 | 10/2007 |
| WO | 2008045668 | 4/2008 |
| WO | 2008118758 | 10/2008 |
| WO | 2008141249 | 11/2008 |
| WO | 2009012242 | 1/2009 |
| WO | 2009017719 | 2/2009 |
| WO | 2009086303 | 7/2009 |
| WO | 2009126863 | 10/2009 |
| WO | 2009129267 | 10/2009 |
| WO | 2010044410 | 4/2010 |
| WO | 2010075376 | 7/2010 |
| WO | 2010079443 | 7/2010 |
| WO | 2010111653 | 9/2010 |
| WO | 2010111713 | 9/2010 |
| WO | 2011009943 | 1/2011 |
| WO | 2012004706 | 1/2012 |
| WO | 2012004714 | 1/2012 |
| WO | 2012004743 | 1/2012 |
| WO | 2012007869 | 1/2012 |
| WO | 2012010183 | 1/2012 |
| WO | 2013057722 | 4/2013 |

OTHER PUBLICATIONS

Mastrukova, T.A., et al., "The application of the Hammett equation to the theory of tautomeric equilibrium-II" Tautomerism of a-arylsulphaminopyridines, Tetrahedron, 1963, pp. 357-372, 19(2).

Murugesan, N., et al., Biphenylsulfonamide Endothelin Antogonists: Structure-Activity Relationships of a Series of Mono- and Disubstituted Analogues and Pharmacology of the Orally Active Endothelin Antagonist 2'-Amino-N-(3,4-dimethyl-5-isoxazoly1)-4'-(2-methylpropyl)[1,1'-biphenyl]-2-sulfonamide (BMA-187308), Journal of Medicinal Chemistry, 1998, pp. 5198-5218, 41(26).

Norinder, U., et al., "QSAR investigation of NaV1.7 active compounds using the SVM/SIgnature approach and the Bioclipse Modeling platform", Bioorganic & Medicinal Chemistry Letters, Jan. 1, 2013, pp. 261-263, 23(1).

Wilson, L.J., et al., "Discovery of novel Cobaction-T based matrix metalloproteinase inhibitors via a ring closing metathesis strategy", Bioorganic & Medicinal Chemistry Letters, Nov. 1, 2011, pp. 6485-6490, 21(21).

Zhang, Yue-Mei, et al., "1-Hydroxy-2-pyridinone-based MMP inhibitors: Synthesis and biological evaluation for the treatment of icshemic stroke", Bioorganic & Medicinal Chemistry Letters, Jan. 1, 2008, pp. 409-413, 18(1).

Zasshi, Yakugaku, "p-Hydroxy-benzenesulfonamide", Chemotherapeutics, XViii, 4, 1951, pp. 315-318, 71(5). English Abstract.

Chemical Abstracts Services (CAS): American Chemical Society, Columbus, Ohio, Apr. 19, 2009, Registry No. 1136471-06-1, Index Name Not Yet Available.

Chemical Abstracts Services (CAS): American Chemical Society, Columbus, Ohio, Mar. 14, 2013, Registry No. 1423476-49-6, Index Name Not Yet Available.

Takatori, Kichitaro, et al., "Synthesis of p-hydroxybenzenesulfonamide derivatives", Gifu Yakka Daigaku Diyo, 1956, pp. 55-58, No. 6. English Abstract.

* cited by examiner

FIG. 1A

FIG. 1B

```
GGGCCCCTCTTCTGGGCCCCTTGAGTAGGTTCCATGGCATTTTCTGAACTCCTGGACCTC
                          ||||| ||      |   || |||||||||
              ACAAGTTTGTACAAAAAAGCAGGCTTCGCCACCATGGCCTTCAGCGAGCTGCTGGACCTG
---------+---------+---------+---------+---------+---------+60
                                        M  A  F  S  E  L  L  D  L
attB1-5'                                URAT1 Initiation codon GTGGGTGGCCTGGGCAGGTTCCAGGTTCTCCAGACGATGGCTCTGATGGTCTCCATCATG
|||||  ||||||||||||  |||||||| ||  |||||  |||||  ||||||||||||
GTGGGAGGCCTGGGCAGATTCCAGGTGCTGCAGACCATGGCCCTGATGGTGTCCATCATG
---------+---------+---------+---------+---------+---------+120
V  G  G  L  G  R  F  Q  V  L  Q  T  M  A  L  M  V  S  I  M TGGCTGTGTACCCAGAGCATGCTGGAGAACTTCTCGGCCGCCGTGCCCAGCCACCGCTGC
||||||||  |||||||||||||||||| |||||||  |||||||||||||||||  |||
TGGCTGTGCACCCAGAGCATGCTGGAAAACTTCTCTGCCGCCGTGCCCAGCCACAGATGC
---------+---------+---------+---------+---------+---------+180
W  L  C  T  Q  S  M  L  E  N  F  S  A  A  V  P  S  H  R  C TGGGCACCCCTCCTGGACAACAGCACGGCTCAGGCCAGCATCCTAGGGAGCTTGAGTCCT
|||||  || || ||||||||||||||  || ||||||||||||||  ||| ||  |||
TGGGCCCCTCTGCTGGACAACAGCACCGCCCAGGCCAGCATCCTGGGCAGCCTGTCTCCA
---------+---------+---------+---------+---------+---------+240
W  A  P  L  L  D  N  S  T  A  Q  A  S  I  L  G  S  L  S  P
``` continued

FIG. 1B

```
GAGGCCCTCCTGGCTATTTCCATCCCGCCGGGCCCCAACCAGAGGCCCCACCAGTGCCGC
|||||||| |||||| ||   |||||| || ||||||||||||||||||||||||| |
GAGGCCCTGCTGGCCATCAGCATCCCCCCTGGCCCCAACCAGAGGCCCCACCAGTGCAGA
---------+---------+---------+---------+---------+---------+300
 E  A  L  L  A  I  S  I  P  P  G  P  N  Q  R  P  H  Q  C  R
```

```
CGCTTCCGCCAGCCACAGTGGCAGCTCTTGGACCCCAATGCCACGGCCACCAGCTGGAGC
|| |||||| |||||| |||||||||||| |||| |||||| |||||| ||||| ||||||
CGGTTCCGGCAGCCTCAGTGGCAGCTGCTGGATCCCAACGCCACCGCCACCTCTTGGAGC
---------+---------+---------+---------+---------+---------+360
 R  F  R  Q  P  Q  W  Q  L  L  D  P  N  A  T  A  T  S  W  S
```

```
GAGGCCGACACGGAGCCGTGTGTGGATGGCTGGGTCTATGACCGCAGCATCTTCACCTCC
|||||||||||| ||||| ||||||||| ||||||||| || |||||    |||||||||| |
GAGGCCGACACCGAGCCCTGTGTGGACGGCTGGGTGTACGACCGGTCCATCTTCACCAGC
---------+---------+---------+---------+---------+---------+420
 E  A  D  T  E  P  C  V  D  G  W  V  Y  D  R  S  I  F  T  S
```

```
ACAATCGTGGCCAAGTGGAACCTCGTGTGTGACTCTCATGCTCTGAAGCCCATGGCCCAG
|| |||||||||||||||||||| |||||  |||  ||  || |||| ||||||||||||||||
ACCATCGTGGCCAAGTGGAACCTGGTGTGCGACAGTCACGCCCTGAAGCCCATGGCCCAG
---------+---------+---------+---------+---------+---------+480
 T  I  V  A  K  W  N  L  V  C  D  S  H  A  L  K  P  M  A  Q
```

```
TCCATCTACCTGGCTGGGATTCTGGTGGGAGCTGCTGCGTGCGGCCCTGCCTCAGACAGG
   |||||||||| || ||||||||||||| || || ||  ||||||||||  ||  ||
AGCATCTACCTGGCCGGCATTCTGGTGGGAGCCGCCGCTTGTGGCCCTGCCAGCGATAGA
---------+---------+---------+---------+---------+---------+540
 S  I  Y  L  A  G  I  L  V  G  A  A  A  C  G  P  A  S  D  R
``` continued

FIG. 1B

```
TTTGGGCGCAGGCTGGTGCTAACCTGGAGCTACCTTCAGATGGCTGTGATGGGTACGGCA
|| ||  |  ||||||||||| ||||||  ||||||  ||||||||| |||||||| || ||
TTCGGCAGACGGCTGGTGCTGACCTGGTCCTACCTGCAGATGGCCGTGATGGGCACCGCC
---------+---------+---------+---------+---------+---------+600
 F   G   R   R   L   V   L   T   W   S   Y   L   Q   M   A   V   M   G   T   A

GCTGCCTTCGCCCCTGCCTTCCCCGTGTACTGCCTGTTCCGCTTCCTGTTGGCCTTTGCC
|| |||||  |||||||||||||||  ||||||||||||||||||  |||||| ||||||| |||
GCAGCCTTTGCCCCTGCCTTCCCTGTGTACTGCCTGTTCCGGTTCCTGCTGGCCTTCGCC
---------+---------+---------+---------+---------+---------+660
 A   A   F   A   P   A   F   P   V   Y   C   L   F   R   F   L   L   A   F   A

GTGGCAGGCGTCATGATGAACACGGGCACTCTCCTGATGGAGTGGACGGCGGCACGGGCC
|||||  |||||  ||||||||||||||| |||||  |||||||||  |||||  || ||   | |||
GTGGCCGGCGTGATGATGAACACCGGCACCCTGCTGATGGAATGGACCGCCGCCAGAGCC
---------+---------+---------+---------+---------+---------+720
 V   A   G   V   M   M   N   T   G   T   L   L   M   E   W   T   A   A   R   A

CGACCCTTGGTGATGACCTTGAACTCTCTGGGCTTCAGCTTCGGCCATGGCCTGACAGCT
 |||||  |||||||||||||  |||||     ||||||||||||||||||  ||||||||| |||||
AGACCCCTGGTGATGACCCTGAACAGCCTGGGCTTCAGCTTCGGACATGGCCTCACAGCC
---------+---------+---------+---------+---------+---------+780
 R   P   L   V   M   T   L   N   S   L   G   F   S   F   G   H   G   L   T   A

GCAGTGGCCTACGGTGTGCGGGACTGGACACTGCTGCAGCTGGTGGTCTCGGTCCCCTTC
|| |||||| || ||  |||||||||||||||||||||||||||||||||||  || ||  ||||||
GCTGTGGCTTATGGCGTGCGGGACTGGACACTGCTGCAGCTGGTGGTGTCCGTGCCCTTC
---------+---------+---------+---------+---------+---------+840
 A   V   A   Y   G   V   R   D   W   T   L   L   Q   L   V   V   S   V   P   F
``` continued

FIG. 1B

```
TTCCTCTGCTTTTTGTACTCCTGGTGGCTGGCAGAGTCGGCACGATGGCTCCTCACCACA
||||| |||||  |||||  |||||||||| || ||||  || || ||||| ||  ||||||
TTCCTGTGCTTCCTGTACAGCTGGTGGCTCGCTGAGAGCGCCCGGTGGCTGCTGACCACA
---------+---------+---------+---------+---------+---------+900
 F  L  C  F  L  Y  S  W  W  L  A  E  S  A  R  W  L  L  T  T

GGCAGGCTGGATTGGGGCCTGCAGGAGCTGTGGAGGGTGGCTGCCATCAACGGAAAGGGG
||||| ||||| ||||||||||||||||| ||||||  ||||  || ||||||||| || |||||
GGCAGACTGGACTGGGGCCTGCAGGAACTGTGGCGGGTCGCCGCCATCAATGGCAAGGGC
---------+---------+---------+---------+---------+---------+960
 G  R  L  D  W  G  L  Q  E  L  W  R  V  A  A  I  N  G  K  G

GCAGTGCAGGACACCCTGACCCCTGAGGTCTTGCTTTCAGCCATGCGGGAGGAGCTGAGC
|| ||||||||||||||||||||||||||||| ||||        ||||||||| ||||| ||||||
GCCGTGCAGGACACCCTGACCCCTGAGGTGCTGCTGAGCGCCATGCGCGAGGAACTGAGC
---------+---------+---------+---------+---------+---------+1020
 A  V  Q  D  T  L  T  P  E  V  L  L  S  A  M  R  E  E  L  S

ATGGGCCAGCCTCCTGCCAGCCTGGGCACCCTGCTCCGCATGCCCGGACTGCGCTTCCGG
|||||||||||||| |||||||||||||||| |||||  |  ||||||||| ||||| ||||||
ATGGGCCAGCCTCCAGCCAGCCTGGGCACACTGCTGAGAATGCCCGGCCTGCGGTTCCGG
---------+---------+---------+---------+---------+---------+1080
 M  G  Q  P  P  A  S  L  G  T  L  L  R  M  P  G  L  R  F  R

ACCTGTATCTCCACGTTGTGCTGGTTCGCCTTTGGCTTCACCTTCTTCGGCCTGGCCCTG
||||| ||| |||   ||||  |||||||||||||| |||||||||||||||||||||||||||||||
ACCTGCATCAGCACCCTGTGTTGGTTCGCCTTCGGCTTCACCTTCTTCGGCCTGGCCCTG
---------+---------+---------+---------+---------+---------+1140
 T  C  I  S  T  L  C  W  F  A  F  G  F  T  F  F  G  L  A  L
``` continued

FIG. 1B

```
GACCTGCAGGCCCTGGGCAGCAACATCTTCCTGCTCCAAATGTTCATTGGTGTCGTGGAC
|||||  |||||||||||||||||||||||||||||||| || |||||||| || || ||||||
GACCTCCAGGCCCTGGGCAGCAACATCTTCCTGCTGCAGATGTTCATCGGCGTGGTGGAC
---------+---------+---------+---------+---------+---------+1200
D   L   Q   A   L   G   S   N   I   F   L   L   Q   M   F   I   G   V   V   D

ATCCCAGCCAAGATGGGCGCCCTGCTGCTGCTGAGCCACCTGGGCCGCCGCCCCACGCTG
|||||  |||||||||||||||||||||||||||||||    |||||||||  |  ||  ||  |||
ATCCCGCCAAGATGGGCGCCCTGCTGCTGCTGTCTCACCTGGGCAGAAGGCCTACCCTG
---------+---------+---------+---------+---------+---------+1260
I   P   A   K   M   G   A   L   L   L   L   S   H   L   G   R   R   P   T   L

GCCGCATCCCTGTTGCTGGCAGGGCTCTGCATTCTGGCCAACACGCTGGTGCCCCACGAA
|||||  ||  |||  ||||||||  ||  ||  ||||||  ||||||||||||  |||||||||||||
GCCGCCTCTCTGCTGCTGGCCGGACTGTGCATCCTGGCCAACACCCTGGTGCCCCACGAG
---------+---------+---------+---------+---------+---------+1320
A   A   S   L   L   A   G   L   C   I   L   A   N   T   L   V   P   H   E

ATGGGGGCTCTGCGCTCAGCCTTGGCCGTGCTGGGGCTGGGCGGGGTGGGGGCTGCCTTC
|||||  ||  |||  |  ||  |||  ||||||||  |||||  |||||  ||  |||||  |||||||||
ATGGGAGCCCTGAGATCTGCCCTGGCCGTCCTGGGACTGGGAGGCGTGGGAGCTGCCTTC
---------+---------+---------+---------+---------+---------+1380
M   G   A   L   R   S   A   L   A   V   L   G   L   G   G   V   G   A   A   F

ACCTGCATCACCATCTACAGCAGCGAGCTCTTCCCCACTGTGCTCAGGATGACGGCAGTG
|||||  ||||||||||||||||||||||||||||  ||||||||||  |||||  |||||||| || |||
ACCTGTATCACCATCTACAGCAGCGAGCTGTTCCCCACCGTGCTGCGGATGACAGCCGTG
---------+---------+---------+---------+---------+---------+1440
T   C   I   T   I   Y   S   S   E   L   F   P   T   V   L   R   M   T   A   V
``` continued

FIG. 1B

```
GGCTTGGGCCAGATGGCAGCCCGTGGAGGAGCCATCCTGGGGCCTCTGGTCCGGCTGCTG
||| |||| |||||||||| ||| | || ||||||||||||||| |||||||| || ||||||
GGCCTGGGACAGATGGCCGCCAGAGGCGGAGCCATCCTGGGACCTCTGGTGCGCCTGCTG
---------+---------+---------+---------+---------+---------+1500
 G  L  G  Q  M  A  A  R  G  G  A  I  L  G  P  L  V  R  L  L

GGTGTCCATGGCCCCTGGCTGCCCTTGCTGGTGTATGGGACGGTGCCAGTGCTGAGTGGC
|| || || || || |||||| ||  |||||||||||| || || |||||||||||  |||
GGAGTGCACGGACCTTGGCTCCCTCTGCTGGTGTACGGCACCGTGCCTGTGCTGTCTGGA
---------+---------+---------+---------+---------+---------+1560
 G  V  H  G  P  W  L  P  L  L  V  Y  G  T  V  P  V  L  S  G

CTGGCCGCACTGCTTCTGCCCGAGACCCAGAGCTTGCCGCTGCCCGACACCATCCAAGAT
||||| || |||||| |||||||||||| |||||| |||| |||||||||||||||| ||
CTGGCTGCTCTGCTGCTGCCCGAGACACAGAGCCTGCCCCTGCCCGACACCATCCAGGAC
---------+---------+---------+---------+---------+---------+1620
 L  A  A  L  L  L  P  E  T  Q  S  L  P  L  P  D  T  I  Q  D

GTGCAGAACCAGGCAGTAAAGAAGGCAACACATGGCACGCTGGGGAACTCTGTCCTAAAA
|||||||||||||| || |||||||| || || |||||| ||||| |||   || || ||
GTGCAGAACCAGGCCGTGAAGAAGGCCACCCACGGCACCCTGGGCAACAGCGTGCTGAAG
---------+---------+---------+---------+---------+---------+1680
 V  Q  N  Q  A  V  K  K  A  T  H  G  T  L  G  N  S  V  L  K

TCCACACAGTTT
|||||| ||||||
TCCACCCAGTTCATGGTGTCCAAGGGGGAGGAACTGTTTACCGGCGTGGTGCCCATCCTG
---------+---------+---------+---------+---------+---------+1740
 S  T  Q  F  M  V  S  K  G  E  E  L  F  T  G  V  V  P  I  L
         End of URAT1 sequence
            Initiation for eGFP
``` continued

FIG. 1B

```
GTGGAACTGGACGGCGACGTGAACGGCCACAAGTTCAGCGTGTCCGGCGAGGGCGAAGGC
---------+---------+---------+---------+---------+---------+1800
 V  E  L  D  G  D  V  N  G  H  K  F  S  V  S  G  E  G  E  G

GACGCCACCTACGGCAAGCTGACCCTGAAGTTCATCTGCACCACCGGCAAGCTGCCCGTG
---------+---------+---------+---------+---------+---------+1860
 D  A  T  Y  G  K  L  T  L  K  F  I  C  T  T  G  K  L  P  V

CCTTGGCCCACCCTGGTGACAACCTTCACCTACGGCGTGCAGTGCTTCGCCAGATACCCC
---------+---------+---------+---------+---------+---------+1920
 P  W  P  T  L  V  T  T  F  T  Y  G  V  Q  C  F  A  R  Y  P

GACCACATGAAGCAGCACGATTTCTTCAAGTCCGCCATGCCCGAGGGCTACGTGCAGGAA
---------+---------+---------+---------+---------+---------+1980
 D  H  M  K  Q  H  D  F  F  K  S  A  M  P  E  G  Y  V  Q  E

CGGACCATCTTCTTCAAGGACGACGGCAACTACAAGACCAGAGCCGAAGTGAAGTTCGAG
---------+---------+---------+---------+---------+---------+2040
 R  T  I  F  F  K  D  D  G  N  Y  K  T  R  A  E  V  K  F  E

GGCGATACCCTGGTGAACCGGATCGAGCTGAAGGGCATCGACTTCAAAGAGGACGGCAAT
---------+---------+---------+---------+---------+---------+2100
 G  D  T  L  V  N  R  I  E  L  K  G  I  D  F  K  E  D  G  N

ATCCTGGGCCACAAGCTGGAGTACAACTACAACAGCCACAAGGTGTACATCACCGCCGAC
---------+---------+---------+---------+---------+---------+2160
 I  L  G  H  K  L  E  Y  N  Y  N  S  H  K  V  Y  I  T  A  D

AAGCAGAAAAACGGCATCAAAGTGAACTTCAAGACCCGGCACAACATCGAGGACGGAAGC
---------+---------+---------+---------+---------+---------+2220
 K  Q  K  N  G  I  K  V  N  F  K  T  R  H  N  I  E  D  G  S
``` continued

FIG. 1B

```
GTGCAGCTGGCCGACCACTACCAGCAGAACACCCCCATCGGCGACGGCCCCGTGCTGCTG
---------+---------+---------+---------+---------+---------+2280
 V  Q  L  A  D  H  Y  Q  Q  N  T  P  I  G  D  G  P  V  L  L

CCTGACAACCACTACCTGAGCACCCAGTCCGCCCTGAGCAAGGACCCCAACGAGAAGCGG
---------+---------+---------+---------+---------+---------+2340
 P  D  N  H  Y  L  S  T  Q  S  A  L  S  K  D  P  N  E  K  R

GACCACATGGTGCTGCTGGAATTCGTGACCGCCGCTGGCATCACACTGGGCATGGACGAG
---------+---------+---------+---------+---------+---------+2400
 D  H  M  V  L  L  E  F  V  T  A  A  G  I  T  L  G  M  D  E attB2-3'
CTGTACAAGTACCCAGCTTTCTTGTACAAAGTGGTTGATATCCAGCACAGTGGCGGCCGC
---------+---------+---------+---------+---------+---------+2460
 L  Y  K  I  P  A  F  L  Y  K  V  V  N  I  Q  H  S  G  G  R
      End of Egfp TCGAGTCTAGAGGGCCCGCGGTTCGAAGGTAAGCCTATCCCTAACCCTCTCCTCGGTCTC
---------+---------+---------+---------+---------+---------+2520
 S  S  L  E  G  P  R  F  E  G  K  P  I  P  N  P  L  L  G  L
                               V5 EPITOPE GATTCTACGCGTACCGGTTAGTAATGA
---------+---------+-------2547
 D  S  T  R  T  G  *  *  *
                 STOP
```

CHEMICAL COMPOUNDS

This application claims the benefit under 35 U.S.C. §119 (e) of U.S. Provisional Patent Application No. 61/917,532, filed on Dec. 18, 2013, and U.S. Provisional Patent Application No. 61/813,809, filed on Apr. 19, 2013, the disclosures of which are hereby incorporated by reference in their entirety.

FIELD OF THE INVENTION

The invention relates to sulfonamide derivatives, to their use in medicine, to compositions containing them, to processes for their preparation and to intermediates used in such processes.

Uric acid is the final product of purine metabolism in humans. In humans, unlike many other animals, uric acid is not further broken down, but is predominantly (70%) excreted into the urine with the remaining 30% excreted in faeces. Hyperuricemia is defined as an excessive production or decreased excretion of uric acid and can occur as an overproduction or under excretion of serum uric acid (sUA), or a combination of the both. Renal under excretion of uric acid is the primary cause of hyperuricemia in about 90% of cases, while overproduction is the cause in less than 10%. Increased sUA concentration above 6.8 mg/dL results in crystallisation of uric acid in the form of salts, such as monosodium urate, and to precipitation of these crystals in joints, on tendons and in the surrounding tissues. These crystals (known as tophi) trigger a local immune-mediated inflammatory reaction, leading to gout. The risk of gout increases with increased sUA levels.

Gout is a painful condition that can present in a number of ways, although the most usual is a recurrent attack of acute inflammatory arthritis (a red, tender, hot, swollen joint) often occurring in big toes, heels, knees, wrists and fingers.

Gout is treated by agents to both decrease the cause and effects of uric acid crystal inflammation and pain.

The pain associated with gout is commonly treated with pain and anti-inflammatory drugs such as nonsteroidal anti-inflammatory drugs (NSAIDs), colchicine and steroids. Agents that decrease sUA levels may be used to treat the cause of gout. These include agents that: inhibit the enzymes that result in uric acid production, such as xanthine oxidase inhibitors (e.g. allopurinol, febuxostat or tisopurine), or purine nucleoside phosphorylase (PNP) inhibitors (e.g. ulodesine); metabolise uric acid, such as urate oxidases—also known as uricases (e.g. pegloticase); or increase the excretion of uric acid in the urine (uricosurics), Uricosurics include agents that inhibit the transporters responsible for renal reabsorption of uric acid back into the blood, such as benziodarone, isobromindione, probenecid and sulphinpyrazone, and URAT-1 inhibitors (e.g. benzbromarone).

URAT-1 is also known as solute carrier family 22 (organic anion/cation transporter), member 12, and is encoded by the gene SLC22A12. Human genetic analysis has demonstrated that polymorphisms in the SLC22A12 gene are directly associated with changes in serum uric acid. Inhibitors of uric acid transport, such as URAT-1, are therefore effective in the treatment of gout.

There is a continuing need to provide new treatments for gout that are more effective and/or are better tolerated.

Certain URAT-1 inhibitors for the treatment of gout are known. WO2011/159840 discloses phenylthioacetate URAT-1 inhibitors. Additionally, WO2008/118758, WO2009/012242, WO2010/079443, WO2012/004706, WO2012/004714 and WO2012/004743 disclose sulphonamides.

There is, however, an ongoing need to provide new URAT-1 inhibitors that are good drug candidates.

Furthermore, preferred compounds should have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile as URAT-1 inhibitors. They should be non-toxic and demonstrate few side-effects. Ideal drug candidates should exist in a physical form that is stable, non-hygroscopic and easily formulated.

SUMMARY OF THE INVENTION

We have now found new sulphonamide URAT-1 inhibitors.

According to a first aspect of the invention there is provided a compound of formula (I)

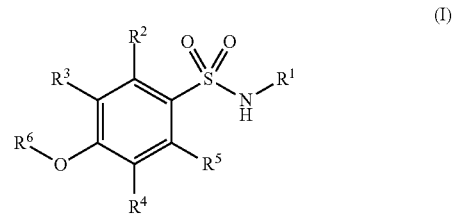

or a pharmaceutically acceptable salt thereof, wherein:
$R^1$ is a 'C-linked' 6-membered heteroaryl containing one, two or three nitrogen atoms wherein said heteroaryl is optionally substituted by one, two or three, valency permitting, $X^1$;
each $X^1$ is independently selected from: F; Cl; CN; $(C_1-C_4)$ alkyl optionally substituted by one, two or three F; and $(C_1-C_4)$alkyloxy optionally substituted by one two or three F;
$R^2$, $R^3$ and $R^5$ are independently selected from: H; halogen; CN; $(C_1-C_4)$alkyl optionally substituted by one, two or three F; and $(C_1-C_4)$alkyloxy optionally substituted by one, two or three F;
$R^4$ is selected from: halogen; CN; $(C_1-C_4)$alkyl optionally substituted by one, two or three F; and $(C_1-C_4)$alkyloxy optionally substituted by one, two or three F;
$R^6$ is phenyl substituted by one, two or three $X^2$; or a 'C-linked' 6-membered heteroaryl containing one or two nitrogen atoms wherein said heteroaryl is optionally substituted by one, two or three $X^2$;
each $X^2$ is independently selected from: F; Cl; CN; —S($C_1$-$C_4$)alkyl; —NR$^7$R$^8$; $(C_1-C_6)$alkyloxy optionally substituted by one, two or three F; $(C_3-C_6)$cycloalkyloxy; $(C_1-C_6)$alkyl optionally substituted by one, two or three F; and $(C_1-C_6)$ alkyl substituted by OH; and
$R^7$ and $R^8$ are independently H or $(C_1-C_4)$alkyl or, together with the nitrogen atom to which they are attached, form a saturated 4- to 6-membered nitrogen containing monocycle.

Described below are a number of embodiments (E) of this first aspect of the invention, where for convenience E1 is identical thereto.

E1 A compound of formula (I) as defined above or a pharmaceutically acceptable salt thereof.

E2 A compound according to E1 wherein $R^1$ is a 'C-linked' 6-membered heteroaryl containing one or two nitrogen atoms, wherein said heteroaryl is optionally substituted by one or two $X^1$.

E3 A compound according to either E1 or E2 wherein $R^1$ is a 'C-linked' 6-membered heteroaryl containing one or two nitrogen atoms, wherein said heteroaryl is optionally substituted by $X^1$.

E4 A compound according to any of E1 to E3 wherein $R^1$ is a 'C-linked' pyridinyl optionally substituted by $X^1$.

E5 A compound according to any of E1 to E4 wherein $R^1$ is a 'C-linked' pyridinyl substituted by $X^1$.

E6 A compound according to any of E1 to E5 wherein $X^1$ is F.

E7 A compound according to any of E1 to E3 wherein $R^1$ is a 'C-linked' 6-membered heteroaryl containing one or two nitrogen atoms.

E8 A compound according to any of E1 to E7 wherein $R^4$ is either halogen or CN, and $R^2$, $R^3$ and $R^5$ are independently selected from: H; halogen; or CN.

E9 A compound according to any of E1 to E8 wherein $R^4$ is CN; and each of $R^2$, $R^3$ and $R^5$ are H.

E10 A compound according to any of E1 to E9 wherein $R^6$ is phenyl substituted by one, two or three $X^2$.

E11 A compound according to E10 wherein $R^6$ is phenyl substituted by two or three $X^2$.

E12 A compound according to any of E1 to E9 wherein $R^6$ is a 'C-linked' 6-membered heteroaryl containing one or two nitrogen atoms, wherein said heteroaryl is optionally substituted by one, two or three $X^2$.

E13 A compound according to E12 wherein $R^6$ is a 'C-linked' 6-membered heteroaryl containing one or two nitrogen atoms, wherein said heteroaryl is substituted by one or two $X^2$.

E14 A compound according to any of E1 to E13 wherein each $X^2$ is independently selected from: F; Cl; CN; —S($C_1$-$C_3$) alkyl; ($C_1$-$C_4$)alkyloxy optionally substituted by one, two or three F; and ($C_1$-$C_4$)alkyl optionally substituted by one, two or three F.

E15 A compound according to any of E1 to E14 wherein each $X^2$ is independently selected from: F; Cl; CN; ($C_1$-$C_3$) alkyloxy; and ($C_1$-$C_3$)alkyl.

E16 A compound according to any of E1 to E15 wherein each $X^2$ is independently selected from: F; Cl; CN; methoxy; and methyl.

E17 A compound according to E1 selected from:

3-cyano-4-(4-cyano-3,5-dimethylphenoxy)-N-(5-fluoropyridin-2-yl)benzenesulfonamide;
4-(3-chloro-4-cyanophenoxy)-3-cyano-N-(5-fluoropyridin-2-yl)benzenesulfonamide;
4-(3-chloro-4-cyanophenoxy)-3-cyano-N-(4-fluoropyridin-2-yl)benzenesulfonamide;
4-(3-chloro-4-fluorophenoxy)-3-cyano-N-(5-fluoropyridin-2-yl)benzenesulfonamide;
3-cyano-N-(5-fluoropyridin-2-yl)-4-(2-methoxy-6-methylphenoxy)benzenesulfonamide;
4-[(5-chloro-6-methoxypyridin-3-yl)oxy]-3-cyano-N-(5-fluoropyridin-2-yl)benzenesulfonamide;
4-(3-chloro-5-cyanophenoxy)-3-cyano-N-(5-fluoropyridin-2-yl)benzenesulfonamide;
4-(4-chloro-3-methoxyphenoxy)-3-cyano-N-(5-fluoropyridin-2-yl)benzenesulfonamide;
4-(4-cyano-3-fluorophenoxy)-2-fluoro-N-(5-fluoropyridin-2-yl)benzenesulfonamide;
4-[(5-chloropyridin-3-yl)oxy]-3-cyano-N-(5-fluoropyridin-2-yl)benzenesulfonamide;
3-cyano-4-(3-fluoro-4-methoxyphenoxy)-N-(5-fluoropyridin-2-yl)benzenesulfonamide;
3-cyano-4-(4-cyano-3-methylphenoxy)-N-(5-fluoropyridin-2-yl)benzenesulfonamide;
3-cyano-4-(4,5-difluoro-2-methoxyphenoxy)-N-(5-fluoropyridin-2-yl)benzenesulfonamide;
3-cyano-4-(3,4-difluorophenoxy)-N-(5-fluoropyridin-2-yl)benzenesulfonamide;
3-cyano-4-(4-fluoro-3-methylphenoxy)-N-(5-fluoropyridin-2-yl)benzenesulfonamide;
3-cyano-4-(4-cyano-2-fluorophenoxy)-N-(5-fluoropyridin-2-yl)benzenesulfonamide;
4-(4-chloro-2-fluorophenoxy)-3-cyano-N-(5-fluoropyridin-2-yl)benzenesulfonamide;
3-cyano-4-(2,6-dimethylphenoxy)-N-(5-fluoropyridin-2-yl)benzenesulfonamide;
4-(2-chloro-3,4-difluorophenoxy)-3-cyano-N-(5-fluoropyridin-2-yl)benzenesulfonamide;
3-cyano-N-(5-fluoropyridin-2-yl)-4-(2,3,4-trifluorophenoxy)benzenesulfonamide;
3-cyano-4-(4-cyano-3-fluorophenoxy)-N-(5-fluoropyridin-2-yl)benzenesulfonamide;
4-(3-chloro-4-methoxyphenoxy)-3-cyano-N-(5-fluoropyridin-2-yl)benzenesulfonamide;
3-cyano-N-(5-fluoropyridin-2-yl)-4-(5-methoxy-2-methylphenoxy)benzenesulfonamide;
3-cyano-4-(2,3-dichloro-4-fluorophenoxy)-N-(5-fluoropyridin-2-yl)benzenesulfonamide;
3-cyano-4-(3-cyano-4-fluorophenoxy)-N-(5-fluoropyridin-2-yl)benzenesulfonamide;
4-(2-chloro-5-cyano-4-methylphenoxy)-3-cyano-N-(5-fluoropyridin-2-yl)benzenesulfonamide;
3-cyano-4-(4-cyano-3-methoxyphenoxy)-N-(5-fluoropyridin-2-yl)benzenesulfonamide;
3-cyano-4-(2,5-dichloro-4-fluorophenoxy)-N-(5-fluoropyridin-2-yl)benzenesulfonamide;
3-cyano-4-(2,4-difluorophenoxy)-N-(5-fluoropyridin-2-yl)benzenesulfonamide;
4-(2-chloro-6-methoxyphenoxy)-3-cyano-N-(5-fluoropyridin-2-yl)benzenesulfonamide;
3-cyano-4-(4-cyanophenoxy)-N-(5-fluoropyridin-2-yl)benzenesulfonamide;
3-cyano-4-(2-fluoro-6-methoxyphenoxy)-N-(5-fluoropyridin-2-yl)benzenesulfonamide;
3-cyano-N-(5-fluoropyridin-2-yl)-4-(4-methoxy-2-methylphenoxy)benzenesulfonamide;
3-cyano-N-(5-fluoropyridin-2-yl)-4-(2-methoxyphenoxy)benzenesulfonamide;
3-cyano-4-(4-cyano-2,5-difluorophenoxy)-N-(5-fluoropyridin-2-yl)benzenesulfonamide;
4-(2-chloro-4-fluorophenoxy)-3-cyano-N-(5-fluoropyridin-2-yl)benzenesulfonamide;
4-(4-chloro-2-methoxyphenoxy)-3-cyano-N-(5-fluoropyridin-2-yl)benzenesulfonamide;
4-(4-chloro-3-methylphenoxy)-3-cyano-N-(5-fluoropyridin-2-yl)benzenesulfonamide;
4-(5-chloro-2-methylphenoxy)-3-cyano-N-(5-fluoropyridin-2-yl)benzenesulfonamide;
3-cyano-4-(2,4-dichlorophenoxy)-N-(5-fluoropyridin-2-yl)benzenesulfonamide;
3-cyano-4-(5-fluoro-2-methylphenoxy)-N-(5-fluoropyridin-2-yl)benzenesulfonamide;
4-(3-chlorophenoxy)-3-cyano-N-(5-fluoropyridin-2-yl)benzenesulfonamide;
4-(4-chlorophenoxy)-3-cyano-N-(5-fluoropyridin-2-yl)benzenesulfonamide;
3-cyano-4-(2,6-difluoro-3-methylphenoxy)-N-(5-fluoropyridin-2-yl)benzenesulfonamide;
4-(2-chloro-6-methylphenoxy)-3-cyano-N-(5-fluoropyridin-2-yl)benzenesulfonamide;
4-(3-chloro-5-fluorophenoxy)-3-cyano-N-(5-fluoropyridin-2-yl)benzenesulfonamide;

4-(4-chloro-3-cyanophenoxy)-3-cyano-N-(5-fluoropyridin-2-yl)benzenesulfonamide;
4-(4-chloro-3,5-dimethylphenoxy)-3-cyano-N-(5-fluoropyridin-2-yl)benzenesulfonamide;
3-cyano-4-(4-fluoro-2-methylphenoxy)-N-(5-fluoropyridin-2-yl)benzenesulfonamide;
4-(2-chloro-6-fluoro-3-methylphenoxy)-3-cyano-N-(5-fluoropyridin-2-yl)benzenesulfonamide; or
3-cyano-4-(3,4-dichlorophenoxy)-N-(5-fluoropyridin-2-yl)benzenesulfonamide;
or a pharmaceutically acceptable salt thereof.

E18 A compound of formula (I)

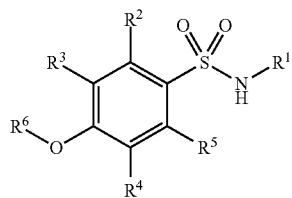

(I)

or a pharmaceutically acceptable salt thereof, wherein:
$R^1$ is a 'C-linked' 6-membered heteroaryl containing one, two or three nitrogen atoms wherein said heteroaryl is optionally substituted by one, two or, valency permitting, three $X^1$;
each $X^1$ is independently selected from: F; Cl; CN; $(C_1$-$C_4)$alkyl optionally substituted by one, two or three F; and $(C_1$-$C_4)$alkyloxy optionally substituted by one two or three F;
one of $R^2$, $R^3$, $R^4$ and $R^5$ is either halogen or CN, and the remainder thereof are independently selected from: H; halogen; or CN;
$R^6$ is phenyl substituted by one, two or three $X^2$; or a 'C-linked' 6-membered heteroaryl containing one or two nitrogen atoms wherein said heteroaryl is optionally substituted by one, two or three $X^2$;
each $X^2$ is independently selected from: F; Cl; CN; —S$(C_1$-$C_4)$alkyl; —NR$^7$R$^8$; $(C_1$-$C_6)$alkyloxy optionally substituted by one, two or three F; $(C_3$-$C_6)$cycloalkyloxy; $(C_1$-$C_6)$alkyl optionally substituted by one, two or three F; and $(C_1$-$C_6)$alkyl substituted by OH; and
each $R^7$ and $R^8$ is independently H or $(C_1$-$C_4)$alkyl or, together with the nitrogen atom to which they are attached, form a saturated 4- to 6-membered nitrogen containing monocycle.

E19 A compound according to E18 wherein $R^1$ is a 'C-linked' 6-membered heteroaryl containing one or two nitrogen atoms, wherein said heteroaryl is optionally substituted by one or two $X^1$.

E20 A compound according to either E18 or E19 wherein $R^1$ is a 'C-linked' 6-membered heteroaryl containing one or two nitrogen atoms, wherein said heteroaryl is optionally substituted by $X^1$.

E21 A compound according to any of E18 to E20 wherein $R^1$ is a 'C-linked' pyridinyl optionally substituted by $X^1$.

E22 A compound according to any of E18 to E21 wherein $R^1$ is a 'C-linked' pyridinyl substituted by $X^1$.

E23 A compound according to any of E18 to E22 wherein $X^1$ is F.

E24 A compound according to any of E18 to E23 wherein $R^1$ is a 'C-linked' 6-membered heteroaryl containing one or two nitrogen atoms.

E25 A compound according to any of E18 to E24 wherein $R^4$ is either halogen or CN, and $R^2$, $R^3$ and $R^5$ are independently selected from: H; halogen; or CN.

E26 A compound according to any of E18 to E25 wherein $R^4$ is CN; and each of $R^2$, $R^3$ and $R^5$ are H.

E27 A compound according to any of E18 to E26 wherein $R^6$ is phenyl substituted by one, two or three $X^2$.

E28 A compound according to E27 wherein $R^6$ is phenyl substituted by two or three $X^2$.

E29 A compound according to any of E18 to E26 wherein $R^6$ is a 'C-linked' 6-membered heteroaryl containing one or two nitrogen atoms, wherein said heteroaryl is optionally substituted by one, two or three $X^2$.

E30 A compound according to E29 wherein $R^6$ is a 'C-linked' 6-membered heteroaryl containing one or two nitrogen atoms, wherein said heteroaryl is substituted by one or two $X^2$.

E31 A compound according to any of E18 to E30 wherein each $X^2$ is independently selected from: F; Cl; CN; —S$(C_1$-$C_3)$alkyl; $(C_1$-$C_4)$alkyloxy optionally substituted by one, two or three F; and $(C_1$-$C_4)$alkyl optionally substituted by one, two or three F.

E32 A compound according to any of E18 to E31 wherein each $X^2$ is independently selected from: F; Cl; CN; $(C_1$-$C_3)$alkyloxy; and $(C_1$-$C_3)$alkyl.

E33 A compound according to any of E18 to E32 wherein each $X^2$ is independently selected from: F: Cl; CN; methoxy; and methyl.

E34 A compound according to E1 which is:
4-[3-chloro-4-(hydroxymethyl)phenoxy]-3-cyano-N-(5-fluoropyridin-2-yl)benzenesulfonamide;
4-{[5-chloro-6-(hydroxymethyl)pyridin-3-yl]oxy}-2-fluoro-N-(5-fluoropyridin-2-yl)benzenesulfonamide;
4-(3-chloro-4-cyanophenoxy)-3-cyano-N-(5-fluoropyridin-2-yl)benzenesulfonamide;
4-[(5-chloropyridin-3-yl)oxy]-3-cyano-N-(5-fluoropyridin-2-yl)benzenesulfonamide;
4-[(6-amino-5-chloropyridin-3-yl)oxy]-3-cyano-N-(5-fluoropyridin-2-yl)benzenesulfonamide;
3-cyano-4-(3,5-dichloro-4-cyanophenoxy)-N-(5-fluoropyridin-2-yl)benzenesulfonamide;
4-(3-chloro-4-cyanophenoxy)-3-cyano-N-(4-fluoropyridin-2-yl)benzenesulfonamide;
4-(3-chloro-4-cyano-5-fluorophenoxy)-3-cyano-N-(5-fluoropyridin-2-yl)benzenesulfonamide;
4-(3-chloro-4-cyanophenoxy)-N-(5-chloropyridin-2-yl)-3-cyanobenzenesulfonamide; or
3-cyano-4-(4-cyano-3,5-dimethylphenoxy)-N-(5-fluoropyridin-2-yl)benzenesulfonamide;
or a pharmaceutically acceptable salt thereof.

Alkyl and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy.

Examples of cycloalkyl include cyclopropyl, cyclobutyl, cyclopentyl and cyclohexyl.

Halo means fluoro, chloro, bromo or iodo.

The term 'C-linked' used in the definitions of formula (I) means that the group in question is joined via a ring carbon.

Specific examples of 'C-linked' 6-membered heteroaryl containing one, two or three nitrogen atoms include pyridinyl, pyridazinyl, pyrimidinyl and pyrazinyl.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $—COO^-Na^+$, $—COO^-K^+$, or $—SO_3^-Na^+$) or non-ionic (such as $—N^-N^+(CH_3)_3$) polar head group. For more information, see *Crystals and the Polarizing Microscope* by N. H. Hartshorne and A. Stuart, 4$^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl) phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (-Ph>-PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994.

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing a compound of formula (I) in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

BRIEF DESCRIPTION OF THE DRAWINGS

FIG. 1A represents a schematic showing organization of the URAT1(L)GFP construct (N to C terminal direction).

FIG. 1B represents a sequence alignment of the codon optimized URAT1(L)GFP construct with the wild type human URAT1 sequence deposited as NM_144585.

Alignment row 1 is the sequence from accession NM_144585.

Alignment row 2 is the sequence of the construct in the Gateway destination vector pLenti6.3V5/DEST (encoding URAT1(L)GFP) with the nucleotide alignment indicated with NM_144585 above and the nucleotide numbering below.

Alignment row 3 is the amino acid translation with sequence annotation indicated in italics below.

DETAILED DESCRIPTION

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, fourth edition, (John Wiley and Sons, 2006), in particular chapters 7 ("Protection for the Amino Group") and 5 ("Protection for the Carboxyl Group"), incorporated herein by reference, which also describes methods for the removal of such groups.

In the following general processes $R^1$, $R^2$, $R^3$, $R^4$, $R^5$ and $R^6$ are as previously defined for a compound of formula (I) unless otherwise stated. PG is a suitable amino protecting group, such as methoxymethyl or dimethoxybenzyl. Hal is a suitable halogen, such as F or Cl. Where ratios of solvents are given, the ratios are by volume.

According to a first process, compounds of formula (I) may be prepared from compounds of formula (II) and (III), as illustrated by Scheme 1.

Scheme 1

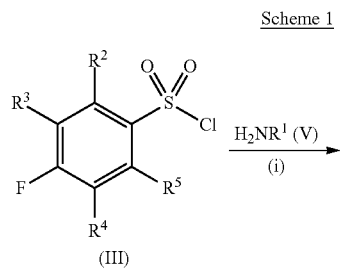

(III)

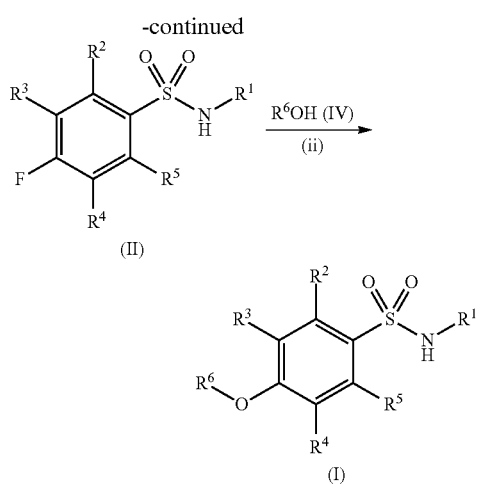

Compounds of formula (I) may be prepared from compounds of formula (II) according to reaction step (ii) by nucleophilic aromatic substitution reaction with compounds of formula (IV) under basic reaction conditions. Convenient conditions are potassium carbonate in DMF or DMSO; cesium carbonate in DMSO; or potassium phosphate in DMSO; and at from room temperature to elevated temperature. Typical conditions comprise potassium carbonate in DMSO at 80-100° C. for 18 hours.

Compounds of formula (II) may be prepared from compounds of formula (III) according to reaction step (i) by displacement of a sulfonyl chloride with compounds of formula (V) under basic reaction conditions. Convenient conditions are pyridine in DCM; 1,4-diazabicyclo[2.2.2]octane in acetonitrile; N-methylmorpholine in THF; or an excess of compound of formula (V). Preferred conditions comprise pyridine in DCM at room temperature.

According to a second process, compounds of formula (I) may be prepared from compounds of formulae (II) and (VIII), as illustrated by Scheme 2.

Compounds of formula (I) may be prepared from compound of formula (VI) according to process step (ii) according to the conditions described in Scheme 1 step (ii), followed by deprotection step (iii), typically mediated by an inorganic or organic acid. Preferred conditions comprise potassium carbonate in DMSO at room temperature, followed by trifluoroacetic acid in DCM or HCl in 1,4-dioxane. It is also possible that deprotection step (iii) may occur under the conditions for effecting the nucleophilic aromatic substitution of step (ii).

Scheme 2

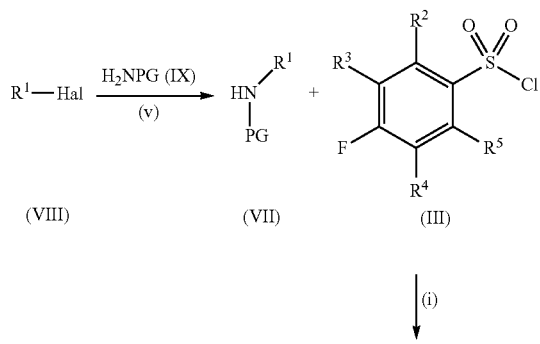

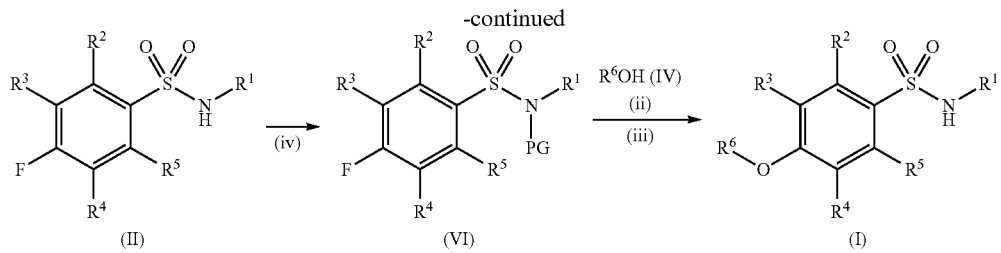

Compounds of formula (VI) may be prepared from compounds of formula (II) according to process step (iv) by introduction of a suitable protecting group, such as methoxymethyl or dimethoxybenzyl, under basic reaction conditions or Mitsunobu reaction conditions. Typical conditions comprise diisopropylethylamine in DCM with chloromethoxymethane.

Alternatively, compounds of formula (VI) may be prepared from compounds of formula (III) according to process step (i) according to the conditions described in Scheme 1 step (i), or by using sodium or lithium hexamethyldisilazane in THF at from −78° C. to room temperature.

Compounds of formulae (II) and (III) may be prepared as described in Scheme 1.

Compounds of formula (VII) may be prepared from compounds of formula (VIII) according to reaction step (v) by a nucleophilic aromatic substitution reaction with compounds of formula (IX) under basic reaction conditions. Preferred conditions comprise diisopropylethylamine in n-butanol at 100° C. or potassium carbonate in DMSO at 110° C.

According to a third process, compounds of formula (I) may be prepared from compounds of formula (XIII) as illustrated by Scheme 3.

Compounds of formula (X) may be prepared from compounds of formula (XI) according to process step (vii), an oxidation reaction in the presence of trichloroisocyanuric acid. Preferred conditions comprise trichloroisocyanuric acid with benzyltrimethylammonium chloride and sodium carbonate in acetonitrile and water.

Compounds of formula (XI) may be prepared from compounds of formula (XII) according to process step (ii), a nucleophilic aromatic substitution reaction with compounds of formula (IV) as described in Scheme 1, step (i).

Compounds of formula (XII) may be prepared from compounds of formula (XIII) according to process step (vi), a cross-coupling reaction with benzylmercaptan in the presence of a suitable catalyst. Conveniently the catalyst is a palladium catalyst. Preferred conditions comprise diisopropylethyamine with [1,1-bis(di-tert-butylphosphino)]ferrocene palladium (II) in toluene at 60° C.

The skilled person will appreciate that a compound of formula (I) wherein $R^2$, $R^3$, $R^4$ or $R^5$ is Cl, Br or I may be converted into the corresponding compound of formula (I) wherein the group in question is H, by dehalogenation in the presence of a suitable catalyst. Typical conditions comprise zinc dust in acetic acid at room temperature, or triethylsilane with tetrakis(triphenylphosphine)palladium(0) in THF at reflux.

Scheme 3

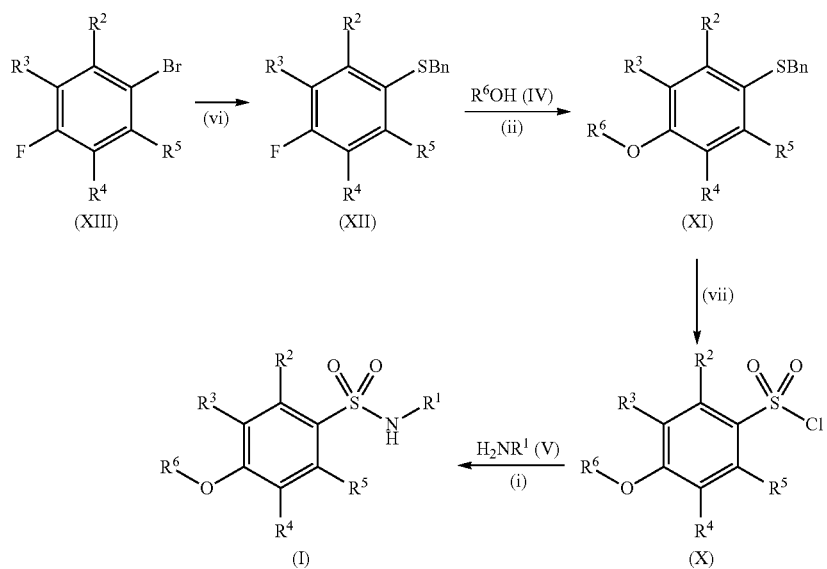

Compounds of formula (I) may be prepared from compounds of formula (X) according to the conditions described in Scheme 2, step(i).

The skilled person will further appreciate that a compound of formula (I) wherein $R^6$ is 2- or 4-halo substituted 'C-linked' 6-membered heteroaryl containing one or two nitrogen atoms may be converted into the corresponding compound of formula (I) substituted by —NR$^7$R$^8$, by reaction with an appropriate amine. Where halo is fluoro, typical conditions comprise heating the compound of formula (I) and the amine of formula HNR$^7$R$^8$ in a solvent such as DMSO, in the presence of an inorganic base such as potassium carbonate, to a temperature of between 50-70° C.

The skilled person will further appreciate that in the aforementioned conversion, when R$^7$ and R$^8$ are both H, it may be necessary or desirable to employ an amino protecting group, such as dimethoxybenzyl, to introduce a protected amine; the protecting group is then removed under conventional conditions, such as in the presence of an organic acid. Preferred conditions comprise dimethoxybenzylamine with potassium carbonate in THF at 70° C., followed by stirring in TFA at room temperature.

Compounds of formula (III), (IV), (V), (VIII), (IX) and (XIII) are commercially available, known from the literature, easily prepared by methods well known to those skilled in the art, or can be made according to preparations described herein.

All new processes for preparing compounds of formula (I), and corresponding new intermediates employed in such processes, form further aspects of the present invention.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™ Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 µg to 100 mg of the compound of formula (I). The overall daily dose will typically be in the range 1 µg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e., URAT-1 inhibition. More particularly, the compounds of the invention are of use in the treatment of disorders for which a URAT-1 inhibitor is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a URAT-1 inhibitor is indicated.

In a further aspect of the invention there is provided use of a compound of the invention for the preparation of a medicament for the treatment of a disorder for which a URAT-1 inhibitor is indicated.

In a further aspect of the invention there is provided a method of treating a disorder in an animal (preferably a mammal, more preferably a human) for which a URAT-1 inhibitor is indicated, comprising administering to said animal a therapeutically effective amount of a compound of the invention.

Disorders for which a URAT-1 inhibitor is indicated include diseases associated with high levels of uric acid in humans and other mammals including (but not limited to) hyperuricemia, asymptomatic hyperuricemia, gout (including juvenile forms), gouty arthritis, inflammatory arthritis, joint inflammation, deposition of urate crystals in the joint, tophaceous gout, chronic kidney disease, nephrolithiasis (kidney stones), Lesch-Nyhan syndrome and Kelley-Seegmiller syndrome.

Hyperuricemia may be defined by blood uric acid levels over 6.8 mg/dL. Guidelines for the management of hyperuricemia recommend that therapies aimed at lowering blood uric acid levels should be maintained until such blood uric acid levels are lowered to below 6.0 mg/dL, such as below 5.0 mg/dL.

The skilled person will appreciate that while by definition without symptoms, asymptomatic hyperuricemia may nevertheless lead to the onset of diseases associated with high levels of uric acid.

The skilled person will also appreciate that the compounds of formula (I) may be used in the treatment of hyperuricemia where this is present together with one or more other diseases, such as kidney failure, type 2 diabetes, cardiovascular disease (e.g. hypertension, myocardial infarction, heart failure, coronary artery disease, cerebrovascular disease, atherosclerosis, angina, aneurism, hyperlipidemia and stroke), obesity, metabolic syndrome, myeloproliferative disorders, lymphoproliferative disorders and disorders associated with certain medications, such as a diuretic (e.g. a thiazide), an immunosuppressant (e.g. a cyclosporine therapy), a chemotherapeutic agent (e.g. cisplatin) or aspirin.

The skilled person will also appreciate that the compounds of formula (I) may be used in the treatment of hyperuricemia where this is present following organ transplant.

A URAT-1 inhibitor may be usefully combined with another pharmacologically active compound, or with two or more other pharmacologically active compounds, particularly in the treatment of a disease associated with elevated blood uric acid levels. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

The compounds of formula (I) may be administered in combination with one or more additional therapeutic agents. Agents of interest include those that also lower blood uric acid levels. Other agents of interest include those that reduce inflammation or pain. The one or more additional therapeutic agents may be selected from any of the agents or types of agent that follow:

a xanthine oxidase inhibitor (e.g. allopurinol, febuxostat or tisopurine);

a purine nucleoside phosphorylase (PNP) inhibitor (e.g. ulodesine);

a uricase (e.g. pegloticase or rasburicase);

a uricosuric, such as an agent that inhibits one or more transporters responsible for reabsorption of uric acid back into the blood at renal or intestinal sites, for example another URAT1 inhibitor (e.g. benzbromarone, PN2107 or RDEA3170); a glucose transporter (GLUT) inhibitor, such as a GLUT9 inhibitor; an organic anion transporter (OAT) inhibitor, such as an OAT4 inhibitor or an OAT10 inhibitor; or an agent which inhibits one or more of the above transporters, such as benziodarone; isobromindione, probenecid, sulphinpyrazone, arhalofenate, tranilast, lesinurad or KUX-1151;

an agent that otherwise exerts blood uric acid lowering effects, such as amlodipine, atorvastatin, fenofibrate or indomethacin;

an anti-inflammatory drug such as an NSAID (e.g. celecoxib), colchicine, a steroid, an interleukin 1 inhibitor (e.g. rilonacept) or an agent that modulates inflammosome signaling cascades (e.g. an IRAK4 inhibitor); or an agent that reduces pain, such as an ion channel modulator (e.g. an inhibitor of Nav1.7, TRPV1 or TRPM2).

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl)acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a URAT-1 inhibitor is indicated.

It is to be appreciated that all references herein to treatment include curative, palliative and prophylactic treatment.

The invention is further illustrated by the non-limiting Examples and Preparations that follow (for the avoidance of doubt, those compounds marked as Reference Examples do not fall within formula (I)).

In these non-limiting Examples and Preparations, and in the aforementioned Schemes, the following abbreviations, definitions and analytical procedures may be referred to:
AcOH is acetic acid;
nBuOH is n-butanol
Cu(acac)$_2$ is copper (II) acetylacetonate;
Cu(OAc)$_2$ is copper (II) acetate;
DABCO is 1,4-diazabicyclo[2,2,2]octane
DAD is diode array detector;
DCM is dichloromethane; methylene chloride;
DEA is diethylamine
DIP-Cl is chlorodiisopinocampheylborane;
DIPEA is N-ethyldiisopropylamine, N,N-diisopropylethylamine;
DMAP is 4-dimethylaminopyridine;
DMF is N,N-dimethylformamide;
DMSO is dimethyl sulphoxide;
EDCI is 1-(3-dimethylaminopropyl)-3-ethylcarbodiimide hydrochloride;
EDTA is ethylenediaminetetraacetic acid;
ELSD is evaporative light scattering detection;
Et$_2$O is diethyl ether;
EtOAc is ethyl acetate;
EtOH is ethanol;
HPLC is high-performance liquid chromatography
IPA is isopropanol;
Ir$_2$(OMe)$_2$COD$_2$ is bis(1,5-cyclooctadiene)di-μ-methoxydiiridium (I);
KOAc is potassium acetate;
K$_3$PO$_4$ is potassium phosphate tribasic;
LCMS is liquid chromatography mass spectrometry (R$_t$=retention time)
Me is methyl
MeOH is methanol;
MS is mass spectrometry
NMM is N-methylmorpholine
NMP is N-Methyl-2-pyrrolidone;
Pd/C is palladium on carbon;
Pd(PPh$_3$)$_4$ is palladium tetrakis;
Pd(dppf)$_2$Cl$_2$ is [1,1'-bis(diphenylphosphino)ferrocene]dichloropalladium(II), complex with dichloromethane;
TBAF is tetra-n-butylammonium fluoride
TBME is tert-butyl methyl ether;
TFA is trifluoroacetate;
THF is tetrahydrofuran;
THP is tetrahydropyran;
TLC is thin layer chromatography;
UV is ultraviolet; and
WSCDI is 1-(3-dimethylaminopropyl)-3-ethylcarbodiimide hydrochloride.

$^1$H and $^{19}$F Nuclear magnetic resonance (NMR) spectra were in all cases consistent with the proposed structures. Characteristic chemical shifts (δ) are given in parts-per-million downfield from tetramethylsilane (for $^1$H-NMR) and upfield from trichloro-fluoro-methane (for $^{19}$F NMR) using conventional abbreviations for designation of major peaks: e.g. s, singlet; d, doublet; t, triplet; q, quartet; m, multiplet; br, broad. The following abbreviations have been used for common solvents: CDCl$_3$, deuterochloroform; d$_6$-DMSO, deuterodimethylsulphoxide; and CD$_3$OD, deuteromethanol.

Mass spectra, MS (m/z), were recorded using either electrospray ionisation (ESI) or atmospheric pressure chemical ionisation (APCI). Where relevant and unless otherwise stated the m/z data provided are for isotopes $^{19}$F, $^{35}$Cl, $^{79}$Br and $^{127}$I.

LCMS Conditions:
System 1
A: 0.1% formic acid in water
B: 0.1% formic acid in acetonitrile
Column: C18 phase Phenomenex 20×4.0 mm with 3 micron particle size
Gradient: 98-2% or 98-10% A over 1.5 min, 0.3 min hold, 0.2 re-equilibration, 1.8 mL/min flow rate
UV: 210 nm-450 nm DAD
Temperature: 75° C.
System 2
A: 0.1% formic acid in water
B: 0.1% formic acid in acetonitrile
Using either:
Column: Agilent Extend C18 phase 50×3 mm with 3 micron particle size
Gradient: 95-0% A over 3.5 min, 1 min hold, 0.4 min re-equilibration, 1.2 mL/min flow rate
Or
Column: C18 phase Waters Sunfire 50×4.6 mm with 5 micron particle size
Gradient: 95-5% A over 3 min, 1 min hold, 2 min re-equilibration, 1 mL/min flow rate
UV: 210 nm-450 nm DAD
Temperature: 50° C.

System 3
A: 10 mM Ammonium Acetate in water (basic Buffer)
B: Acetonitrile
Column: Xbridge C18 4.6×50 mm with 5 micron particle size
Gradient: from 90% [Buffer] and 10% [MeCN] to 70% [Buffer] and 30% [MeCN] in 1.5 min, further to 10% [buffer] and 90% [MeCN] in 3.0 min, held for 4 min and back to initial condition in 5 min),
1.2 mL/min flow rate
UV: 220 nm
Temperature: 25° C.

DETAILED DESCRIPTION OF THE PREFERRED EMBODIMENTS

Example 1

4-(3-chloro-4-cyanophenoxy)-3-cyano-N-(5-fluoro-pyridin-2-yl)benzenesulfonamide

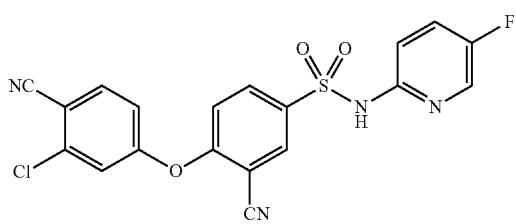 [SMILES: N#Cc1ccc(Oc2ccc(S(=O)(=O)Nc3ccc(F)cn3)cc2C#N)cc1Cl]

3-Cyano-4-fluoro-N-(5-fluoropyridin-2-yl)benzene-sulfonamide (Preparation 2, 10.5 g, 35.6 mmol) was added to a solution of 2-chloro-4-hydroxybenzonitrile (8.19 g, 53.3 mmol) and potassium carbonate (14.74 g, 106.7 mmol) in dimethylsulfoxide (100 mL) at room temperature. The resulting mixture was stirred at 80° C. for 44 hours. On cooling, the reaction mixture was poured into saturated aqueous sodium hydrogen carbonate solution (200 mL) and ethyl acetate (1000 mL) was added. The aqueous layer was separated and the organic layer was washed with saturated aqueous sodium hydrogen carbonate solution (3×200 mL), water (2×200 mL) and brine (2×200 mL). The organic layer was dried over sodium sulphate, filtered and concentrated in vacuo. The residue was purified by reverse phase column chromatography eluting with acetonitrile (containing 0.1% $HCO_2H$): water (containing 0.1% $HCO_2H$) from 0 to 100% to afford the title compound as a white solid (6.982 g, 46%).

$^1$H NMR (400 MHz, DMSO-$d_6$): δ ppm 7.09 (dd, 1H), 7.28 (d, 1H), 7.44 (dd, 1H), 7.68 (td, 1H), 7.81 (d, 1H), 8.09-8.15 (m, 2H), 8.19 (d, 1H), 8.41 (d, 1H), 11.30 (br s, 1H).

$^{19}$F NMR (400 MHz, DMSO-$d_6$): δ ppm −134

MS m/z 427 [M−H]$^-$

General Method:

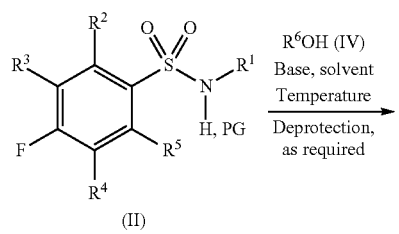

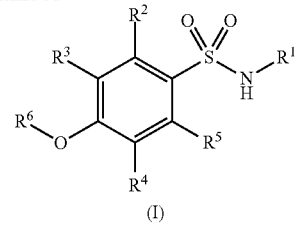

Wherein $R^1$, $R^2$, $R^3$, $R^4$, $R^5$ and $R^6$ are as previously defined for a compound of formula (I), unless otherwise stated, and PG (where present) is a suitable amino protecting group, such as methoxymethyl or dimethoxybenzyl.

a) To a solution of a compound of formula (IV) was added an inorganic base (as specifically described in the Method Variations below), followed by a compound of formula (II). The reaction mixture was: cooled, kept at room temperature or heated, as required.

The reaction mixture was diluted with water, or an aqueous solution of an inorganic acid such as saturated aqueous ammonium chloride or 2N HCl, or an aqueous solution of an inorganic base such as 1N NaOH; extracted into a solvent such as DCM or EtOAc; dried over a drying agent such as $MgSO_4$ or $Na_2SO_4$; and concentrated in vacuo to afford a residue. Alternatively, the reaction was concentrated in vacuo directly. The residue was purified as necessary.

b) Where required, the residue was deprotected using an acid such as TFA or HCl in dioxane/DCM, to afford the compound of formula (I).

Method Variations (MV):

Method 1: a) Unprotected compound (II), $K_2CO_3$ in DMSO at 80-100° C. for 48 hours.

Method 2: a) Unprotected compound (II), $K_2CO_3$ in DMF at 90° C. for 24 hours.

Method 3: a) Methoxymethyl protected compound (II), $K_2CO_3$ in DMSO at 80-100° C. for 24 hours. Deprotection occurs under the conditions for effecting the nucleophilic aromatic substitution.

Method 4: a) Methoxymethyl protected compound (II), $K_2CO_3$ or $Cs_2CO_3$ in DMSO at from room temperature to 100° C. for 18 hours.

b) Followed by deprotection with 4M HCl in dioxane or TFA at room temperature for 18 hours.

Method 5: a) Dimethoxybenzyl protected compound (II), $K_2CO_3$ in DMSO at from room temperature to 60° C. for 18 hours.

b) Followed by deprotection with 4M HCl in dioxane or TFA at room temperature for 18 hours.

Method 6: a) Unprotected compound (II), $Cs_2CO_3$ in DMSO at 80-100° C. for 48 hours.

Method 7: a) Dimethoxybenzyl protected compound (II), $K_3PO_4$ in DMSO at 80° C. for 18 hours.

b) Followed by deprotection with 4M HCl in dioxane at room temperature for 18 hours.

Purification Methods (PM):

Purification Method A: Preparative HPLC

For compounds of the Examples prepared as singletons (i.e. other than via the Library Protocols described hereinafter), one of two preparative HPLC methods was used, as shown below:

Acidic Conditions

| Column | Gemini NX C18, 5 um 21.2 × 100 mm |
|---|---|
| Temperature | Ambient |
| Detection | ELSD-MS |
| Mobile Phase A | 0.1% formic acid in water |
| Mobile Phase B | 0.1% formic acid in acetonitrile |
| Gradient | initial 0% B, 1 mins—5% B; 7 mins—98% B; 9 mins—98% B; 9.1 mins—5% B; 10 mins—5% B |
| Flow rate | 18 mL/min |
| Injection volume | 1000 uL |

Basic Conditions

| Column | Gemini NX C18, 5 um 21.2 × 100 mm |
|---|---|
| Temperature | Ambient |
| Detection | ELSD-MS |
| Mobile Phase A | 0.1% diethylamine in water |
| Mobile Phase B | 0.1% diethylamine in acetonitrile |
| Gradient | initial 0% B, 1 mins—5% B; 7 mins—98% B; 9 mins—98% B; 9.1 mins—5% B; 10 mins—5% B |
| Flow rate | 18 mL/min |
| Injection volume | 1000 uL |

Purification Method B: Silica gel column chromatography eluting with:
i) 95:5 DCM:EtOAc;
ii) 12-75% EtOAc in heptanes;
iii) 1:1 TBME:Heptanes; or
iv) 0-1% MeOH in DCM.

Purification Method C: Reverse phase column chromatography using:
Column: Phenomenex Luna C18 5 u 110A 21.2×150 mm
Detection @ 254 nm, threshold 25 mV
Solvent system:
　A: 0.05% formic acid in water, B: 0.05% formic acid in acetonitrile, 0 min 95% A, 2.25 min 95% A, 17.5 min 95% B, 22.5 min 95% B;
　Between 5-60% MeCN in water; or
　85% A to 100% B over 25 minutes, where mobile phase A is water:MeCN:TFA 7800:200:8 and mobile phase B is MeCN:water:TFA 7200:800:8.

Purification Method D: Trituration with MeOH and/or DCM or EtOAc.

Purification Method E: Reverse phase silica gel column chromatography eluting with (0.1% formic acid in MeCN): (0.1% formic acid in water) from 0-100%.

Unless stated otherwise, the compounds of the Examples in the table below were prepared from 3-cyano-4-fluoro-N-(5-fluoropyridin-2-yl)benzenesulfonamide (Preparation 2) and the appropriate phenol according to Method Variation 1 (MV1), and then purified according to Purification Method A (PM A).

| Ex | Name | Phenol | MS Data (MV, PM) |
|---|---|---|---|
| 2 | 3-cyano-4-(3-ethylphenoxy)-N-(5-fluoropyridin-2-yl)benzenesulfonamide formate salt | 3-ethylphenol | m/z 396 [M − H]− |
| 3 | 3-cyano-4-(2,3-dichlorophenoxy)-N-(5-fluoropyridin-2-yl)benzenesulfonamide formate salt | 2,3-dichlorophenol | m/z 438 [M + H]+ |
| 4 | 3-cyano-N-(5-fluoropyridin-2-yl)-4-[2-fluoro-5-(trifluoromethyl)phenoxy]benzenesulfonamide | 2-fluoro-5-trifluoromethyl-phenol | m/z 456 [M + H]+ |
| 5 | 4-(4-chloro-2-methylphenoxy)-3-cyano-N-(5-fluoropyridin-2-yl)benzenesulfonamide formate salt | 4-chloro-2-methylphenol | m/z 416 [M − H]− |
| 6 | 3-cyano-4-[4-cyano-3-(trifluoromethyl)phenoxy]-N-(5-fluoropyridin-2-yl)benzenesulfonamide formate salt | 4-cyano-3-trifluoromethyl phenol | m/z 463 [M + H]+ |
| 7 | 3-cyano-4-(2,4-difluorophenoxy)-N-(5-fluoropyridin-2-yl)benzenesulfonamide formate salt | 2,4-difluorophenol | m/z 406 [M + H]+ |
| 8 | 3-cyano-4-(3-fluoro-5-methoxyphenoxy)-N-(5-fluoropyridin-2-yl)benzenesulfonamide formate salt | 3-fluoro-5-methoxyphenol | m/z 418 [M + H]+ |
| 9 | 4-(2-chlorophenoxy)-3-cyano-N-(5-fluoropyridin-2-yl)benzenesulfonamide formate salt | 2-chlorophenol | m/z 404 [M + H]+ |
| 10 | 3-cyano-4-(4-cyanophenoxy)-N-(5-fluoropyridin-2-yl)benzenesulfonamide diethylamine salt | 4-cyanophenol | m/z 395 [M + H]+ |
| 11 | 3-cyano-4-(3,5-difluorophenoxy)-N-(5-fluoropyridin-2-yl)benzenesulfonamide formate salt | 3,5-difluorophenol | m/z 406 [M + H]+ |
| 12 | 3-cyano-4-(4-cyano-2-fluorophenoxy)-N-(5-fluoropyridin-2-yl)benzenesulfonamide diethylamine salt | 4-cyano-2-fluorophenol | m/z 825 [2M + H]+ |
| 13 | 3-cyano-4-(2,4-dichlorophenoxy)-N-(5-fluoropyridin-2-yl)benzenesulfonamide diethylamine salt | 2,4-dichlorophenol | m/z 875 [2M + H]+ |
| 14 | 3-cyano-4-(3-cyanophenoxy)-N-(5-fluoropyridin-2-yl)benzenesulfonamide formate salt | 3-cyanophenol | m/z 395 [M + H]+ |
| 15 | 4-(3-chloro-5-methylphenoxy)-3-cyano-N-(5-fluoropyridin-2-yl)benzenesulfonamide diethylamine salt | 3-chloro-5-methylphenol | m/z 418 [M + H]+ |

-continued

| Ex | Name | Phenol | MS Data (MV, PM) |
|---|---|---|---|
| 16 | 3-cyano-4-(2,3-difluorophenoxy)-N-(5-fluoropyridin-2-yl)benzenesulfonamide formate salt | 2,3-difluorophenol | m/z 406 [M + H]+ |
| 17 | 3-cyano-4-(2-cyanophenoxy)-N-(5-fluoropyridin-2-yl)benzenesulfonamide formate salt | 2-cyanophenol | m/z 789 [2M + H]+ |
| 18 | 3-cyano-N-(5-fluoropyridin-2-yl)-4-[3-(trifluoromethoxy)phenoxy]benzenesulfonamide formate salt | 3-(trifluoromethoxy)phenol | m/z 454 [M + H]+ |
| 19 | 3-cyano-4-(3-cyano-4-fluorophenoxy)-N-(5-fluoropyridin-2-yl)benzenesulfonamide formate salt | 3-cyano-4-fluorophenol | m/z 413 [M + H]+ |
| 20 | 4-(4-chlorophenoxy)-3-cyano-N-(5-fluoropyridin-2-yl)benzenesulfonamide formate salt | 4-chlorophenol | m/z 404 [M + H]+ |
| 21 | 3-cyano-4-(5-fluoro-2-methylphenoxy)-N-(5-fluoropyridin-2-yl)benzenesulfonamide formate salt | 5-fluoro-2-methylphenol | m/z 402 [M + H]+ |
| 22 | 4-(3-chloro-4-methylphenoxy)-3-cyano-N-(5-fluoropyridin-2-yl)benzenesulfonamide diethylamine salt | 3-chloro-4-methylphenol | m/z 418 [M + H]+ |
| 23 | 3-cyano-N-(5-fluoropyridin-2-yl)-4-[3-(trifluoromethyl)phenoxy]benzenesulfonamide formate salt | 3-(trifluoromethyl)phenol | m/z 438 [M + H]+ |
| 24 | 4-(3-chloro-2-fluorophenoxy)-3-cyano-N-(5-fluoropyridin-2-yl)benzenesulfonamide formate salt | 3-chloro-2-fluorophenol | m/z 422 [M + H]+ |
| 25 | 4-(3-chlorophenoxy)-3-cyano-N-(5-fluoropyridin-2-yl)benzenesulfonamide diethylamine salt | 3-chlorophenol | m/z 404 [M + H]+ |
| 26 | 4-(2-chloro-5-cyano-4-methylphenoxy)-3-cyano-N-(5-fluoropyridin-2-yl)benzenesulfonamide formate salt | 2-chloro-5-cyano-4-methylphenol | m/z 443 [M + H]+ |
| 27 | 3-cyano-N-(5-fluoropyridin-2-yl)-4-[2-(trifluoromethoxy)phenoxy]benzenesulfonamide diethylamine salt | 2-(trifluoromethoxy)phenol | m/z 454 [M + H]+ |
| 28 | 4-(3-chloro-5-fluorophenoxy)-3-cyano-N-(5-fluoropyridin-2-yl)benzenesulfonamide diethylamine salt | 3-chloro-5-fluorophenol | m/z 422 [M + H]+. |
| 29 | 3-cyano-N-(5-fluoropyridin-2-yl)-4-[2-fluoro-3-(trifluoromethyl)phenoxy]benzenesulfonamide diethylamine salt | 2-fluoro-3-(trifluoromethyl)phenol | m/z 456 [M + H]+ |
| 30 | 4-(2-chloro-4-cyanophenoxy)-3-cyano-N-(5-fluoropyridin-2-yl)benzenesulfonamide diethylamine salt | 2-chloro-4-cyanophenol | m/z 429 [M + H]+ |
| 31 | 4-(2-chloro-4-fluorophenoxy)-3-cyano-N-(5-fluoropyridin-2-yl)benzenesulfonamide formate salt | 2-chloro-4-fluorophenol | m/z 422 [M + H]+ |
| 32 | 4-(2-chloro-3,5-difluorophenoxy)-3-cyano-N-(5-fluoropyridin-2-yl)benzenesulfonamide formate salt | 2-chloro-3,5-difluorophenol | m/z 440 [M + H]+ |
| 33 | 3-cyano-4-(2-fluoro-5-methylphenoxy)-N-(5-fluoropyridin-2-yl)benzenesulfonamide formate salt | 2-fluoro-5-methylphenol | m/z 803 [2M + H]+ |
| 34 | 4-(4-chloro-3-methylphenoxy)-3-cyano-N-(5-fluoropyridin-2-yl)benzenesulfonamide formate salt | 4-chloro-3-methylphenol | m/z 418 [M + H]+ |
| 35 | 3-cyano-N-(5-fluoropyridin-2-yl)-4-[4-(trifluoromethoxy)phenoxy]benzenesulfonamide formate salt | 4-(trifluoromethoxy)phenol | m/z 454 [M + H]+ |
| 36 | 3-cyano-4-(2-cyano-4-fluorophenoxy)-N-(5-fluoropyridin-2-yl)benzenesulfonamide diethylamine salt | 2-cyano-4-fluorophenol | m/z 413 [M + H]+ |
| 37 | 4-(2-chloro-5-methylphenoxy)-3-cyano-N-(5-fluoropyridin-2-yl)benzenesulfonamide formate salt | 2-chloro-5-methylphenol | m/z 835 [2M + H]+ |
| 38 | 3-cyano-4-(2,3-dichloro-4-fluorophenoxy)-N-(5-fluoropyridin-2-yl)benzenesulfonamide formate salt | 2,3-dichloro-4-fluorophenol | m/z 456 [M + H]+ |
| 39 | 4-(5-chloro-2-methylphenoxy)-3-cyano-N-(5-fluoropyridin-2-yl)benzenesulfonamide formate salt | 5-chloro-2-methylphenol | m/z 418 [M + H]+ |
| 40 | 3-cyano-N-(5-fluoropyridin-2-yl)-4-[3-fluoro-5-(trifluoromethyl)phenoxy]benzenesulfonamide formate salt | 3-fluoro-5-(trifluoromethyl)phenol | m/z 456 [M + H]+ |

-continued

| Ex | Name | Phenol | MS Data (MV, PM) |
|---|---|---|---|
| 41 | 3-cyano-4-(2-fluorophenoxy)-N-(5-fluoropyridin-2-yl)benzenesulfonamide formate salt | 2-fluorophenol | m/z 388 [M + H]+ |
| 42 | 4-(2-chloro-4-methylphenoxy)-3-cyano-N-(5-fluoropyridin-2-yl)benzenesulfonamide formate salt | 2-chloro-4-methylphenol | m/z 418 [M + H]+ |
| 43 | 3-cyano-4-(4-cyano-3-fluorophenoxy)-N-(5-fluoropyridin-2-yl)benzenesulfonamide diethylamine salt | 4-cyano-3-fluorophenol | m/z 413 [M + H]+ |
| 44 | 4-(2-chloro-5-methoxyphenoxy)-3-cyano-N-(5-fluoropyridin-2-yl)benzenesulfonamide diethylamine salt | 2-chloro-5-methoxyphenol | m/z 434 [M + H]+ |
| 45 | 4-(4-chloro-2-cyanophenoxy)-3-cyano-N-(5-fluoropyridin-2-yl)benzenesulfonamide formate salt | 4-chloro-2-cyanophenol | m/z 429 [M + H]+ |
| 46 | 3-cyano-4-(2-ethylphenoxy)-N-(5-fluoropyridin-2-yl)benzenesulfonamide diethylamine salt | 2-ethylphenol | m/z 398 [M + H]+ |
| 47 | 4-(4-chloro-2-fluorophenoxy)-3-cyano-N-(5-fluoropyridin-2-yl)benzenesulfonamide formate salt | 4-chloro-2-fluorophenol | m/z 422 [M + H]+ |
| 48 | 3-cyano-N-(5-fluoropyridin-2-yl)-4-[4-fluoro-3-(trifluoromethyl)phenoxy]benzenesulfonamide | 4-fluoro-3-(trifluoromethyl)phenol | m/z 456 [M + H]+ |
| 49 | 3-cyano-N-(5-fluoropyridin-2-yl)-4-[2-(propan-2-yl)phenoxy]benzenesulfonamide formate salt | 2-(propan-2-yl)phenol | m/z 412 [M + H]+ |
| 50 | 3-cyano-4-(4-ethylphenoxy)-N-(5-fluoropyridin-2-yl)benzenesulfonamide diethylamine salt | 4-ethylphenol | m/z 398 [M + H]+ |
| 51 | 3-cyano-N-(5-fluoropyridin-2-yl)-4-[2-(trifluoromethyl)phenoxy]benzenesulfonamide formate salt | 2-(trifluoromethyl)phenol | m/z 438 [M + H]+ |
| 52 | 3-cyano-4-(3-fluorophenoxy)-N-(5-fluoropyridin-2-yl)benzenesulfonamide formate salt | 3-fluorophenol | m/z 388 [M + H]+ |
| 53 | 3-cyano-4-(2,5-difluorophenoxy)-N-(5-fluoropyridin-2-yl)benzenesulfonamide formate salt | 2,5-difluorophenol | m/z 406 [M + H]+ |
| 54 | 3-cyano-N-(5-fluoropyridin-2-yl)-4-[4-(trifluoromethyl)phenoxy]benzenesulfonamide formate salt | 4-(trifluoromethyl)phenol | m/z 438 [M + H]+ |
| 55 | 4-(4-chloro-3-fluorophenoxy)-3-cyano-N-(5-fluoropyridin-2-yl)benzenesulfonamide | 4-chloro-3-fluorophenol | m/z 422 [M + H]+ |
| 56 | 3-cyano-4-(2-ethyl-4-fluorophenoxy)-N-(5-fluoropyridin-2-yl)benzenesulfonamide | 2-ethyl-4-fluorophenol | m/z 416 [M + H]+ PM B |
| 57 | 3-cyano-N-(5-fluoropyridin-2-yl)-4-[3-(propan-2-yl)phenoxy]benzenesulfonamide | 3-(propan-2-yl)phenol | m/z 412 [M + H]+ MV 2 PM B |
| 58 | 4-(4-chloro-2-iodophenoxy)-3-cyano-N-(5-fluoropyridin-2-yl)benzenesulfonamide (Reference Example) | 4-chloro-2-iodophenol | m/z 530 [M + H]+ MV 2 PM B |
| 59 | 3-cyano-4-(3-cyano-4-methylphenoxy)-N-(5-fluoropyridin-2-yl)benzenesulfonamide | 3-cyano-4-methylphenol | m/z 409 [M + H]+ PM B |
| 60 | 4-(4-chloro-3-cyanophenoxy)-3-cyano-N-(5-fluoropyridin-2-yl)benzenesulfonamide | 4-chloro-3-cyanophenol | m/z 429 [M + H]+ PM B |
| 61 | 3-cyano-4-(4-cyano-3-methylphenoxy)-N-(5-fluoropyridin-2-yl)benzenesulfonamide | 4-cyano-3-methylphenol | m/z 407 [M − H]− PM B |
| 62 | 4-(3-chloro-5-cyanophenoxy)-3-cyano-N-(5-fluoropyridin-2-yl)benzenesulfonamide | 3-chloro-5-cyanophenol | m/z 429 [M + H]+ MV 6 |
| 63 | 4-(2-chloro-5-cyanophenoxy)-3-cyano-N-(5-fluoropyridin-2-yl)benzenesulfonamide | 2-chloro-5-cyanophenol | m/z 429 [M + H]+ MV 6 |
| 64 | 4-(2-chloro-3-cyanophenoxy)-3-cyano-N-(5-fluoropyridin-2-yl)benzenesulfonamide | 2-chloro-3-cyanophenol | m/z 427 [M − H]− |
| 65 | 4-(5-chloro-2-cyanophenoxy)-3-cyano-N-(5-fluoropyridin-2-yl)benzenesulfonamide | 5-chloro-2-cyanophenol | m/z 427 [M − H]− |
| 66 | 3-cyano-4-(3-cyano-4-methoxyphenoxy)-N-(5-fluoropyridin-2-yl)benzenesulfonamide | 3-cyano-4-methoxyphenol | m/z 423 [M − H]− |

-continued

| Ex | Name | Phenol | MS Data (MV, PM) |
|---|---|---|---|
| 67 | 3-cyano-4-[4-cyano-2-(difluoromethoxy)phenoxy]-N-(5-fluoropyridin-2-yl)benzenesulfonamide | 4-cyano-2-(difluoromethoxy)phenol | m/z 459 [M − H]⁻ |
| 68 | 4-[(5-chloro-6-cyanopyridin-3-yl)oxy]-3-cyano-N-(5-fluoropyridin-2-yl)benzenesulfonamide | 5-chloro-6-cyanopyridin-3-yl)ol (WO2011009943) | m/z 430 [M + H]⁺ PM B |
| 69 | 3-cyano-4-(5-cyano-2-fluorophenoxy)-N-(5-fluoropyridin-2-yl)benzenesulfonamide | 5-cyano-2-fluorophenol | m/z 413 [M + H]⁺ |
| 70 | 4-[(5-chloro-6-methoxypyridin-3-yl)oxy]-3-cyano-N-(5-fluoropyridin-2-yl)benzenesulfonamide (from 3-cyano-N-(2,4-dimethoxybenzyl)-4-fluoro-N-(5-fluoropyridin-2-yl)benzenesulfonamide) | 5-chloro-6-methoxypyridin-3-yl)ol | m/z 433 [M − H]⁻ MV 5 PM C |
| 71 | 4-(4-chloro-3-methoxyphenoxy)-3-cyano-N-(5-fluoropyridin-2-yl)benzenesulfonamide (from 3-cyano-N-(2,4-dimethoxybenzyl)-4-fluoro-N-(5-fluoropyridin-2-yl)benzenesulfonamide) | 4-chloro-3-methoxyphenol | m/z 434 [M + H]⁺ MV 5 |
| 72 | 3-cyano-4-(4-cyano-2,5-difluorophenoxy)-N-(5-fluoropyridin-2-yl)benzenesulfonamide (from 3-cyano-N-(2,4-dimethoxybenzyl)-4-fluoro-N-(5-fluoropyridin-2-yl)benzenesulfonamide) | 4-cyano-2,5-difluorophenol | m/z 431 [M + H]⁺ MV 5 PM B |
| 73 | 4-(2-chloro-6-cyanophenoxy)-3-cyano-N-(5-fluoropyridin-2-yl)benzenesulfonamide (from 3-cyano-N-(2,4-dimethoxybenzyl)-4-fluoro-N-(5-fluoropyridin-2-yl)benzenesulfonamide) | 2-chloro-6-cyanophenol | m/z 429 [M + H]⁺ MV 5 PM B |
| 74 | 4-[4-chloro-2-(difluoromethoxy)phenoxy]-3-cyano-N-(5-fluoropyridin-2-yl)benzenesulfonamide (from 3-cyano-N-(2,4-dimethoxybenzyl)-4-fluoro-N-(5-fluoropyridin-2-yl)benzenesulfonamide) | 4-chloro-2-(difluoromethoxy)phenol | m/z 470 [M + H]⁺ MV 5 |
| 75 | 3-cyano-4-(3-cyano-2-fluorophenoxy)-N-(5-fluoropyridin-2-yl)benzenesulfonamide | 3-cyano-2-fluorophenol | m/z 413 [M + H]⁺ PM B |
| 76 | 3-cyano-4-(4-cyano-3-methoxyphenoxy)-N-(5-fluoropyridin-2-yl)benzenesulfonamide | 4-cyano-3-methoxyphenol | m/z 423 [M − H]⁻ |
| 77 | 3-cyano-4-(3,4-difluorophenoxy)-N-(5-fluoropyridin-2-yl)benzenesulfonamide | 3,4-difluorophenol | m/z 404 [M − H]⁻ PM B |
| 78 | 4-(3-chloro-4-fluorophenoxy)-3-cyano-N-(5-fluoropyridin-2-yl)benzenesulfonamide | 3-chloro-4-fluorophenol | m/z 422 [M + H]⁺ PM B |
| 79 | 3-cyano-4-(4-cyano-3,5-dimethylphenoxy)-N-(5-fluoropyridin-2-yl)benzenesulfonamide | 4-cyano-3,5-dimethylphenol | m/z 421 [M − H]⁻ PM D |

The compounds of the Examples in the table below were prepared from appropriate compounds of formulae (II) and (IV) according to the specified Method Variation (MV) and, as necessary, purified according to the specified Purification Method (PM).

| Ex | Name | Phenol & Sulfonamide | MS Data (MV, PM) |
|---|---|---|---|
| 80 | 4-(4-chloro-2-iodophenoxy)-3-cyano-N-(pyridin-2-yl)benzenesulfonamide (Reference Example) | 4-chloro-2-iodophenol and 3-cyano-4-fluoro-N-(pyridin-2-yl)benzenesulfonamide | m/z 512 [M + H]⁺ MV 2 |
| 81 | 3-chloro-4-(4-chloro-2-methoxyphenoxy)-N-(pyridazin-3-yl)benzenesulfonamide | 4-chloro-2-methoxyphenol and 3-chloro-4-fluoro-N-(methoxymethyl)-N-(pyridazin-3-yl)benzenesulfonamide (WO2012004743) | m/z 424 [M − H]⁻ MV 3 PM A |
| 82 | 4-{4-chloro-2-[D₃-methyloxy]phenoxy}-3-cyano-N-(pyridazin-3-yl)benzenesulfonamide | 4-chloro-2-D₃-methoxyphenol and 3-cyano-4-fluoro-N-(methoxymethyl)-N-(pyridazin-3-yl)benzenesulfonamide | m/z 420 [M + H]⁺ MV 4 PM A |

-continued

| Ex | Name | Phenol & Sulfonamide | MS Data (MV, PM) |
|---|---|---|---|
| 83 | 5-chloro-4-[4-chloro-2-(difluoromethoxy)phenoxy]-2-fluoro-N-(pyrimidin-2-yl)benzenesulfonamide | 4-chloro-2-(difluoromethoxy)phenol and 5-chloro-N-(2,4-dimethoxybenzyl)-2,4-difluoro-N-(pyrimidin-2-yl)benzenesulfonamide (WO2012004743) | m/z 480 [M + H]$^+$ MV 5 PM C |
| 84 | 3-chloro-4-[4-chloro-2-(difluoromethoxy)phenoxy]-N-(pyridazin-3-yl)benzenesulfonamide | 4-chloro-2-(difluoromethoxy)phenol and 3-chloro-4-fluoro-N-(methoxymethyl)-N-(pyrimidin-2-yl)benzenesulfonamide (WO2012004743) | m/z 462 [M + H]$^+$ MV 4 PM C |
| 85 | 5-chloro-4-[4-chloro-2-(difluoromethoxy)phenoxy]-2-fluoro-N-(pyridazin-3-yl)benzenesulfonamide | 4-chloro-2-(difluoromethoxy)phenol and 5-chloro-2,4-difluoro-N-(methoxymethyl)-N-(pyrimidin-2-yl)benzenesulfonamide (WO2010079443) | m/z 480 [M + H]$^+$ MV 4 PM B |
| 86 | 4-[4-chloro-2-(difluoromethoxy)phenoxy]-3-cyano-N-(pyridazin-3-yl)benzenesulfonamide | 4-chloro-2-(difluoromethoxy)phenol and 3-cyano-4-fluoro-N-(methoxymethyl)-N-(pyridazin-3-yl)benzenesulfonamide | m/z 453 [M + H]$^+$ MV 4 PM C |
| 87 | 4-(3-chloro-4-cyanophenoxy)-3-cyano-N-(pyrimidin-4-yl)benzenesulfonamide | 3-chloro-4-cyanophenol and 5-chloro-N-(2,4-dimethoxybenzyl)-2,4-difluoro-N-(pyrimidin-4-yl)benzenesulfonamide | m/z 410 [M − H]$^-$ MV 5 PM D |
| 88 | 3-cyano-4-(4-cyano-3-fluorophenoxy)-N-(pyridazin-3-yl)benzenesulfonamide | 4-cyano-3-fluorophenol and 3-cyano-N-(2,4-dimethoxybenzyl)-4-fluoro-N-(pyridazin-3-yl)benzenesulfonamide | m/z 394 [M − H]$^-$ MV 5 PM A |
| 89 | 4-(3-chloro-4-cyanophenoxy)-3-cyano-N-(pyridin-2-yl)benzenesulfonamide | 3-chloro-4-cyanophenol and 3-cyano-4-fluoro-N-(pyridin-2-yl)benzenesulfonamide | m/z 411 [M + H]$^+$ MV 1 PM D |
| 90 | 4-(3-chloro-4-cyanophenoxy)-3-cyano-N-(pyrimidin-2-yl)benzenesulfonamide | 3-chloro-4-cyanophenol and 3-cyano-N-(2,4-dimethoxybenzyl)-4-fluoro-N-(pyrimidin-2-yl)benzenesulfonamide | m/z 412 [M + H]$^+$ MV 7 PM A |
| 91 | 4-(3-chloro-4-cyanophenoxy)-3-cyano-N-(5-fluoropyrimidin-2-yl)benzenesulfonamide | 3-chloro-4-cyanophenol and 3-cyano-N-(2,4-dimethoxybenzyl)-4-fluoro-N-(5-fluoropyrimidin-2-yl)benzenesulfonamide | m/z 428 [M − H]$^-$ MV 5 PM C. |
| 92 | 4-(3-chloro-4-cyanophenoxy)-3-cyano-N-(pyridin-3-yl)benzenesulfonamide | 3-chloro-4-cyanophenol and 3-cyano-4-fluoro-N-(pyridin-3-yl)benzenesulfonamide | m/z 411 [M + H]$^+$ MV 1 PM A |
| 93 | 4-(3-chloro-4-cyanophenoxy)-3-cyano-N-(pyrazin-2-yl)benzenesulfonamide | 3-chloro-4-cyanophenol and 3-cyano-4-fluoro-N-(pyrazin-2-yl)benzenesulfonamide | m/z 412 [M + H]$^+$ MV 1 PM A, followed by PM B |
| 94 | 4-(3-chloro-4-cyanophenoxy)-3-cyano-N-(pyridazin-4-yl)benzenesulfonamide | 3-chloro-4-cyanophenol and 3-chloro-4-fluoro-N-(pyridazin-4-yl)benzenesulfonamide | m/z 412 [M + H]$^+$ MV 1 PM A |
| 95 | 4-(4-cyano-3-fluorophenoxy)-2,5-difluoro-N-(5-fluoropyridin-2-yl)benzenesulfonamide | 4-cyano-3-fluorophenol and N-2,4-dimethoxybenzyl-2,4,5-trifluoro-N-(5-fluoropyridin-2-yl)benzenesulfonamide | m/z 422 [M − H]$^-$ |
| 96 | 4-(3-chloro-4-cyanophenoxy)-3-cyano-N-(pyrimidin-5-yl)benzenesulfonamide | 3-chloro-4-cyanophenol and 3-cyano-4-fluoro-N-(pyrimidin-5-yl)benzenesulfonamide | m/z 410 [M − H]$^-$ MV 5 PM C |
| 97 | 4-(4-cyano-3-fluorophenoxy)-3-fluoro-N-(5-fluoropyridin-2-yl)benzenesulfonamide | 4-cyano-3-fluorophenol and N-3,4-dimethoxybenzyl-3,4-di-fluoro-N-(5-fluoropyridin-2-yl)benzenesulfonamide | m/z 406 [M + H]$^+$ MV 5 PM C |
| 98 | 4-(3-chloro-4-cyanophenoxy)-3-cyano-N-(pyridazin-3-yl)benzenesulfonamide | 3-chloro-4-cyanophenol and 3-cyano-N-(2,4-dimethoxybenzyl)-4-fluoro-N-(pyridazin-3-yl)benzenesulfonamide. | m/z 412 [M + H]$^+$ |

Example 99

4-(4-cyano-3-fluorophenoxy)-2-fluoro-N-(5-fluoropyridin-2-yl)benzenesulfonamide

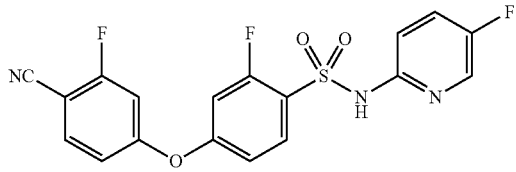 [SMILES: N#Cc1ccc(Oc2ccc(S(=O)(=O)Nc3ccc(F)cn3)c(F)c2)cc1F]

To a solution of 5-bromo-4-(4-cyano-3-fluorophenoxy)-N-(2,4-dimethoxybenzyl)-2-fluoro-N-(5-fluoropyridin-2-yl)benzenesulfonamide (Preparation 1, 220 mg, 0.35 mmol) in THF (8 mL), AcOH (10 mL) and water (2.5 mL) was added zinc dust (800 mg, 12.2 mmol). The reaction mixture was left to stir at room temperature for 70 hours. To the reaction mixture was added EtOAc (25 mL) and the mixture filtered through celite and washed with EtOAc (50 mL). The filtrate was retained and to this was added saturated aqueous NaHCO$_3$ (80 mL). The organic layer was retained, dried over MgSO$_4$, and the solvent removed in vacuo. The residue was purified using reverse phase column chromatography eluting with acetonitrile and water (acidic). The residue was dissolved in DCM and treated with TFA (0.3 mL) and stirred at room temperature for 1 hour. The reaction was concentrated in vacuo azeotroping with MeOH. The residue was purified using preparative HPLC to afford the title compound as a colourless powder (16 mg, 26%).

MS m/z 404 [M−H]$^-$

Example 100

4-(3-chloro-4-cyanophenoxy)-3-cyano-N-(pyridin-4-yl)benzenesulfonamide

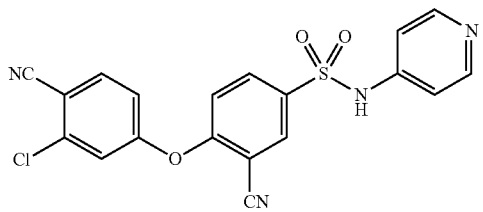 [SMILES: N#Cc1ccc(Oc2ccc(S(=O)(=O)Nc3ccncc3)cc2C#N)cc1Cl]

The title compound was prepared according to the method described for Example 101 using 4-aminopyridine.

MS m/z 411 [M+H]$^+$

Example 101

4-(3-chloro-4-cyanophenoxy)-3-cyano-N-(3-methylpyridin-2-yl)benzenesulfonamide

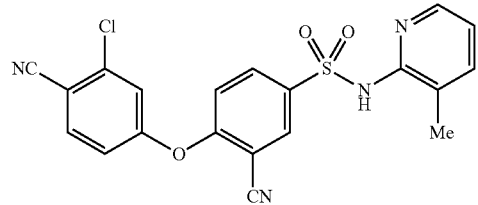 [SMILES: Cc1cccnc1NS(=O)(=O)c1ccc(Oc2ccc(C#N)c(Cl)c2)c(C#N)c1]

To a solution of 4-(3-chloro-4-cyanophenoxy)-3-cyanobenzene-1-sulfonyl chloride (Preparation 21, 240 mg, 0.65 mmol) in dry dichloromethane (3 ml) was added 3-methylpyridin-2-amine (176 mg, 1.63 mmol). The reaction mixture was stirred at room temperature for 16 hours. The reaction mixture was evaporated to dryness under vacuum to leave a brown gum (150 mg). The crude material was dissolved in dimethylsulfoxide and purified by preparative HPLC to afford the title compound as a colourless solid (44 mg, 16%).

$^1$H NMR (400 MHz, DMSO-d$_6$): δ ppm 2.17 (s, 3H), 6.81 (t, 1H), 7.39 (d, 1H), 7.42 (d, 1H), 7.63 (s, 1H), 7.71 (d, 1H), 7.90 (d, 1H), 8.01 (d, 1H), 8.22 (d, 1H), 8.40 (s, 1H).

MS m/z 425 [M+H]$^+$

Example 102

4-(3-chloro-4-cyanophenoxy)-3-cyano-N-(3-methoxypyridin-2-yl)benzenesulfonamide

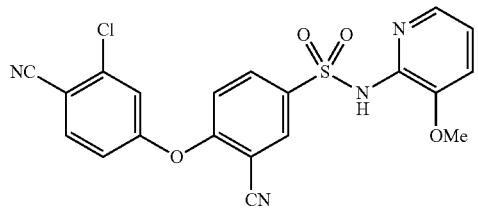 [SMILES: COc1cccnc1NS(=O)(=O)c1ccc(Oc2ccc(C#N)c(Cl)c2)c(C#N)c1]

The title compound was prepared according to the Method described for Example 101 using 3-methoxypyridine-2-amine. The reaction mixture was diluted with dichloromethane and washed with 2 M HCl (100 mL). The organic phase was dried with MgSO$_4$, filtered, and evaporated to dryness under vacuum to leave a light brown solid. The residue was dissolved in dichloromethane and purified using silica gel column chromatography eluting with 0% to 40% ethyl acetate in heptanes.

MS m/z 441 [M+H]$^+$

Example 103

4-(3-chloro-4-cyanophenoxy)-3-cyano-N-(3-fluoropyridin-2-yl)benzenesulfonamide

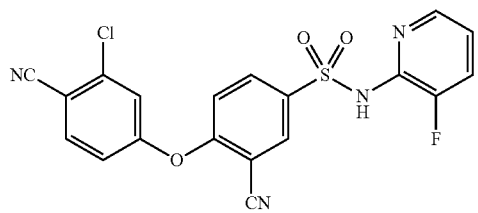 [SMILES: N#Cc1ccc(Oc2ccc(S(=O)(=O)Nc3ncccc3F)cc2C#N)cc1Cl]

The title compound was prepared according to the Method described for Example 101 using 3-fluoropyridine-2-amine.

MS m/z 429 [M+H]$^+$

Example 104

4-(3-chloro-4-cyanophenoxy)-3-cyano-N-(4-fluoropyridin-2-yl)benzenesulfonamide

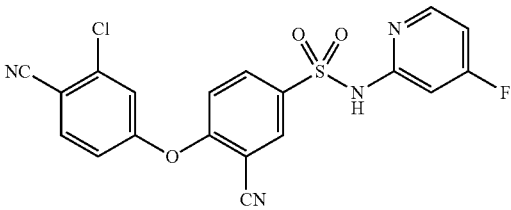 [SMILES: N#Cc1ccc(Oc2ccc(S(=O)(=O)Nc3cc(F)ccn3)cc2C#N)cc1Cl]

The title compound was prepared according to the Method described for Example 101 using 3-fluoropyridine-2-amine in pyridine.

MS m/z 429 [M+H]$^+$

Library Protocol 1

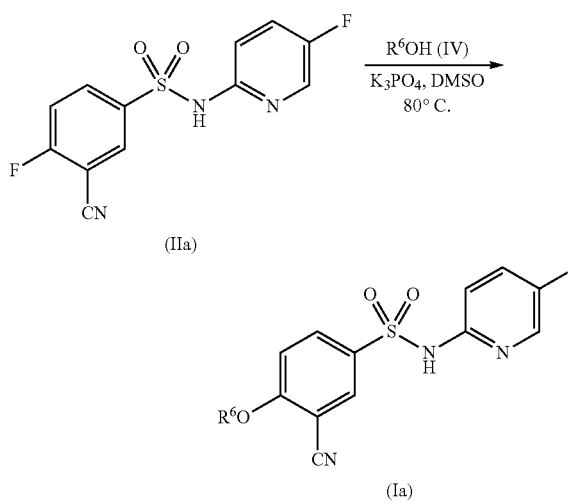

To a 0.2M solution of 3-cyano-4-fluoro-N-(5-fluoropyridin-2-yl)benzenesulfonamide in DMSO (Preparation 2, 500 uL, 100 umol) was added a 0.2M solution in DMSO of the appropriate phenol/hydroxypyridine (compound of formula (IV), 500 uL, 100 umol) followed by anhydrous $K_3PO_4$ (64 mg, 300 umol) and the reaction mixtures were stirred at 80° C. for 18 hours. The reaction mixtures were cooled and purified using one of the two preparative HPLC described below to afford the desired compounds of formula (Ia).

Preparative HPLC Method 1:
Mobile phase A: 10 mM ammonium acetate in water; Mobile phase B: MeCN
Column: Gemini NX C18 (20×100 mm, 5 u)
Gradient: Initial 10% B; 2 mins 40% B; 10 mins 70% B, 11-12 mins 95% B, 13-15 mins 10% B
Flow rate: 20 mL/min.

Preparative HPLC Method 2:
Mobile phase A: 10 mM ammonium acetate in water; Mobile phase B: MeCN
Column: Xbridge C18 (19×50 mm, 5 u)
Gradient: Initial 10% B; 2 mins 20% B; 7 mins 80% B, 7.5-8.5 mins 95% B, 9-10 mins 10% B,
Flow rate: 20 mL/min LCMS Conditions:
Mobile phase A: 0.05% formic acid in water; Mobile phase B: MeCN
Column: RESTEK C18 2.1×30 mm×3µ
Gradient: From 98% A and 2% B to 90% A and 10% B in 1 min, further to 2% A and 98% B in 2.0 min and finally back to initial condition in 3 min
Flow rate: 1.5 mL/min The compounds of the Examples in the table below were prepared from 3-cyano-4-fluoro-N-(5-fluoropyridin-2-yl)benzenesulfonamide in DMSO (Preparation 2) and the appropriate phenol or hydroxypyridine according to Library protocol 1.

| Ex | Name | $R^6OH$ | MS Data |
|---|---|---|---|
| 105 | 3-cyano-N-(5-fluoropyridin-2-yl)-4-[3-methyl-5-(propan-2-yl)phenoxy]benzenesulfonamide | 3-methyl-5-(propan-2-yl)phenol | m/z 426 $[M + H]^+$ |
| 106 | 4-(5-chloro-2-methoxyphenoxy)-3-cyano-N-(5-fluoropyridin-2-yl)benzenesulfonamide | 5-chloro-2-methoxyphenol | m/z 434 $[M + H]^+$ |
| 107 | 3-cyano-4-(2,5-dichloro-4-fluorophenoxy)-N-(5-fluoropyridin-2-yl)benzenesulfonamide | 2,5-dichloro-4-fluorophenol | m/z 456 $[M + H]^+$ |
| 108 | 4-(2-chloro-6-fluoro-3-methylphenoxy)-3-cyano-N-(5-fluoropyridin-2-yl)benzenesulfonamide | 2-chloro-6-fluoro-3-methylphenol | m/z 436 $[M + H]^+$ |
| 109 | 3-cyano-4-(2,4-dichloro-5-methylphenoxy)-N-(5-fluoropyridin-2-yl)benzenesulfonamide | 2,4-dichloro-5-methylphenol | m/z 452 $[M + H]^+$ |
| 110 | 4-(4-chloro-2-ethoxyphenoxy)-3-cyano-N-(5-fluoropyridin-2-yl)benzenesulfonamide | 4-chloro-2-ethoxyphenol | m/z 448 $[M + H]^+$ |
| 111 | 3-cyano-4-(2-fluoro-6-methoxyphenoxy)-N-(5-fluoropyridin-2-yl)benzenesulfonamide | 2-fluoro-6-methoxyphenol | m/z 418 $[M + H]+$ |
| 112 | 4-(2-chloro-4-fluoro-3-methoxyphenoxy)-3-cyano-N-(5-fluoropyridin-2-yl)benzenesulfonamide | 2-chloro-4-fluoro-3-methoxyphenol | m/z 452 $[M + H]^+$ |
| 113 | 3-cyano-4-[3-(diethylamino)phenoxy]-N-(5-fluoropyridin-2-yl)benzenesulfonamide | 3-(diethylamino)phenol | m/z 441 $[M + H]^+$ |
| 114 | 4-(2-chloro-6-methoxyphenoxy)-3-cyano-N-(5-fluoropyridin-2-yl)benzenesulfonamide | 2-chloro-6-methoxyphenol | m/z 434 $[M + H]^+$ |
| 115 | 3-cyano-N-(5-fluoropyridin-2-yl)-4-(2-methoxy-6-methylphenoxy)benzenesulfonamide | 2-methoxy-6-methylphenol | m/z 414 $[M + H]^+$ |
| 116 | 4-(3-chloro-4-ethoxyphenoxy)-3-cyano-N-(5-fluoropyridin-2-yl)benzenesulfonamide | 3-chloro-4-ethoxyphenol | m/z 448 $[M + H]^+$ |
| 117 | 4-{[5-chloro-6-(propan-2-yl)pyridin-3-yl]oxy}-3-cyano-N-(5-fluoropyridin-2-yl)benzenesulfonamide | 5-chloro-6-(propan-2-yl)pyridin-3-yl]ol (WO20120010183) | m/z 447 $[M + H]^+$ |
| 118 | 3-cyano-4-(3-cyclopropylphenoxy)-N-(5-fluoropyridin-2-yl)benzenesulfonamide (Reference Example) | 3-cyclopropylphenol | m/z 410 $[M + H]^+$ |
| 119 | 3-cyano-4-(2,6-difluoro-3-methylphenoxy)-N-(5-fluoropyridin-2-yl)benzenesulfonamide | 2,6-difluoro-3-methylphenol | m/z 420 $M + H]^+$ |
| 120 | 3-cyano-4-(5-fluoro-2-methoxyphenoxy)-N-(5-fluoropyridin-2-yl)benzenesulfonamide | 5-fluoro-2-methoxyphenol | m/z 418 $[M + H]^+$ |

-continued

| Ex | Name | R⁶OH | MS Data |
|---|---|---|---|
| 121 | 3-cyano-N-(5-fluoropyridin-2-yl)-4-{[6-(2-methylpropoxy)pyridin-3-yl]oxy}benzenesulfonamide | 6-(2-methylpropoxy)pyridin-3-yl]ol | m/z 441 [M − H]⁻ |
| 122 | 3-cyano-4-(3,4-dichlorophenoxy)-N-(5-fluoropyridin-2-yl)benzenesulfonamide | 3,4-dichlorophenol | m/z 436 [M − H]⁻ |
| 123 | 4-(2-chloro-6-methylphenoxy)-3-cyano-N-(5-fluoropyridin-2-yl)benzenesulfonamide | 2-chloro-6-methylphenol | m/z 418 [M + H]⁺ |
| 124 | 3-cyano-4-(2,6-difluorophenoxy)-N-(5-fluoropyridin-2-yl)benzenesulfonamide | 2,6-difluorophenol | m/z 406 [M + H]⁺ |
| 125 | 4-[(5-chloro-6-ethoxypyridin-3-yl)oxy]-3-cyano-N-(5-fluoropyridin-2-yl)benzenesulfonamide | 5-chloro-6-ethoxypyridin-3-yl)ol. | m/z 449 [M + H]⁺ |
| 126 | 3-cyano-N-(5-fluoropyridin-2-yl)-4-[4-(propan-2-yl)phenoxy]benzenesulfonamide | 4-(propan-2-yl)phenol | m/z 412 [M + H]⁺ |
| 127 | 4-(4-tert-butyl-2-chlorophenoxy)-3-cyano-N-(5-fluoropyridin-2-yl)benzenesulfonamide | 4-tert-butyl-2-chlorophenol | m/z 460 [M + H]⁺ |
| 128 | 3-cyano-4-(2,3-difluoro-4-methylphenoxy)-N-(5-fluoropyridin-2-yl)benzenesulfonamide | 2,3-difluoro-4-methylphenol | m/z 420 [M + H]⁺ |
| 129 | 4-(3-tert-butylphenoxy)-3-cyano-N-(5-fluoropyridin-2-yl)benzenesulfonamide | 3-tert-butylphenol | m/z 426 [M + H]⁺ |
| 130 | 3-cyano-N-(5-fluoropyridin-2-yl)-4-(2,4,5-trifluorophenoxy)benzenesulfonamide | 2,4,5-trifluorophenol | m/z 424 [M + H]⁺ |
| 131 | 3-cyano-4-[3-(dimethylamino)phenoxy]-N-(5-fluoropyridin-2-yl)benzenesulfonamide | 3-(dimethylamino)phenol | m/z 413 [M + H]⁺ |
| 132 | 3-cyano-4-(3-fluoro-4-methoxyphenoxy)-N-(5-fluoropyridin-2-yl)benzenesulfonamide | 3-fluoro-4-methoxyphenol | m/z 418 [M + H]⁺ |
| 133 | 4-[4-chloro-5-methyl-2-(propan-2-yl)phenoxy]-3-cyano-N-(5-fluoropyridin-2-yl)benzenesulfonamide | 4-chloro-5-methyl-2-(propan-2-yl)phenol | m/z 460 [M + H]⁺ |
| 134 | 3-cyano-N-(5-fluoropyridin-2-yl)-4-(2,3,6-trifluorophenoxy)benzenesulfonamide | 2,3,6-trifluorophenol | m/z 424 [M + H]⁺ |
| 135 | 3-cyano-4-(3-ethoxyphenoxy)-N-(5-fluoropyridin-2-yl)benzenesulfonamide | 3-ethoxyphenol | m/z 414 [M + H]⁺ |
| 136 | 4-(2-chloro-4,5-dimethylphenoxy)-3-cyano-N-(5-fluoropyridin-2-yl)benzenesulfonamide | 2-chloro-4,5-dimethylphenol | m/z 432 [M + H]⁺ |
| 137 | 4-(4-tert-butylphenoxy)-3-cyano-N-(5-fluoropyridin-2-yl)benzenesulfonamide | 4-tert-butylphenol | m/z 426 [M + H]⁺ |
| 138 | 3-cyano-4-(2-ethoxy-4-methylphenoxy)-N-(5-fluoropyridin-2-yl)benzenesulfonamide | 2-ethoxy-4-methylphenol | m/z 428 [M + H]⁺ |
| 139 | 3-cyano-N-(5-fluoropyridin-2-yl)-4-[3-methyl-4-(propan-2-yl)phenoxy]benzenesulfonamide | 3-methyl-4-(propan-2-yl)phenol | m/z 426 [M + H]⁺ |
| 140 | 3-cyano-N-(5-fluoropyridin-2-yl)-4-(2-methoxy-4-methylphenoxy)benzenesulfonamide | 2-methoxy-4-methylphenol | m/z 414 [M + H]⁺ |
| 141 | 3-cyano-4-(4-fluoro-3-methylphenoxy)-N-(5-fluoropyridin-2-yl)benzenesulfonamide | 4-fluoro-3-methylphenol | m/z 402 [M + H]⁺ |
| 142 | 3-cyano-N-(5-fluoropyridin-2-yl)-4-(2-methoxyphenoxy)benzenesulfonamide | 2-methoxyphenol | m/z 400 [M + H]⁺ |
| 143 | 4-(4-chloro-2-methoxyphenoxy)-3-cyano-N-(5-fluoropyridin-2-yl)benzenesulfonamide | 4-chloro-2-methoxyphenol | m/z 434 [M + H]⁺ |
| 144 | 3-cyano-4-(4,5-difluoro-2-methoxyphenoxy)-N-(5-fluoropyridin-2-yl)benzenesulfonamide | 4,5-difluoro-2-methoxyphenol | m/z 436 [M + H]⁺ |
| 145 | 3-cyano-4-(4-fluoro-2-methylphenoxy)-N-(5-fluoropyridin-2-yl)benzenesulfonamide | 4-fluoro-2-methylphenol | m/z 402 [M + H]⁺ |
| 146 | 3-cyano-N-(5-fluoropyridin-2-yl)-4-[2-(methylsulfanyl)phenoxy]benzenesulfonamide | 2-(methylsulfanyl)phenol | m/z 416 [M + H]⁺ |
| 147 | 4-(2-chloro-4-fluoro-3-methylphenoxy)-3-cyano-N-(5-fluoropyridin-2-yl)benzenesulfonamide | 2-chloro-4-fluoro-3-methylphenol | m/z 436 [M + H]⁺ |
| 148 | 4-(3-chloro-4-methoxyphenoxy)-3-cyano-N-(5-fluoropyridin-2-yl)benzenesulfonamide | 3-chloro-4-methoxyphenol | m/z 434 [M + H]⁺ |
| 149 | 4-(4-chloro-3,5-dimethylphenoxy)-3-cyano-N-(5-fluoropyridin-2-yl)benzenesulfonamide | 4-chloro-3,5-dimethylphenol | m/z 432 [M + H]⁺ |
| 150 | 3-cyano-4-(3,5-dimethylphenoxy)-N-(5-fluoropyridin-2-yl)benzenesulfonamide | 3,5-dimethylphenol | m/z 398 [M + H]⁺ |
| 151 | 3-cyano-4-(2-ethoxyphenoxy)-N-(5-fluoropyridin-2-yl)benzenesulfonamide | 2-ethoxyphenol | m/z 414 [M + H]⁺ |
| 152 | 3-cyano-4-(2,6-dimethylphenoxy)-N-(5-fluoropyridin-2-yl)benzenesulfonamide | 2,6-dimethylphenol | m/z 398 [M + H]⁺ |
| 153 | 3-cyano-4-(4-ethoxyphenoxy)-N-(5-fluoropyridin-2-yl)benzenesulfonamide | 4-ethoxyphenol | m/z 414 [M + H]⁺ |

| Ex | Name | R⁶OH | MS Data |
|---|---|---|---|
| 154 | 3-cyano-4-[(2-ethoxypyridin-3-yl)oxy]-N-(5-fluoropyridin-2-yl)benzenesulfonamide | 2-ethoxypyridin-3-yl)ol | m/z 415 [M + H]⁺ |
| 155 | 3-cyano-N-(5-fluoropyridin-2-yl)-4-(2-methoxy-5-methylphenoxy)benzenesulfonamide | 2-methoxy-5-methylphenol | m/z 414 [M + H]⁺ |
| 156 | 3-cyano-4-[5-fluoro-2-(propan-2-yloxy)phenoxy]-N-(5-fluoropyridin-2-yl)benzenesulfonamide | 5-fluoro-2-(propan-2-yloxy)phenol | m/z 446 [M + H]⁺ |
| 157 | 3-cyano-N-(5-fluoropyridin-2-yl)-4-(2,3,4-trifluorophenoxy)benzenesulfonamide | 2,3,4-trifluorophenol | m/z 424 [M + H]⁺ |
| 158 | 3-cyano-4-(2,5-dimethylphenoxy)-N-(5-fluoropyridin-2-yl)benzenesulfonamide | 2,5-dimethylphenol | m/z 398 [M + H]⁺ |
| 159 | 4-(5-chloro-2,3-dimethylphenoxy)-3-cyano-N-(5-fluoropyridin-2-yl)benzenesulfonamide | 5-chloro-2,3-dimethylphenol | m/z 432 [M + H]⁺ |
| 160 | 3-cyano-4-(4-fluoro-2-methoxyphenoxy)-N-(5-fluoropyridin-2-yl)benzenesulfonamide | 4-fluoro-2-methoxyphenol | m/z 418 [M + H]⁺ |
| 161 | 4-(3-tert-butyl-4-cyanophenoxy)-3-cyano-N-(5-fluoropyridin-2-yl)benzenesulfonamide | 3-tert-butyl-4-cyanophenol | m/z 451 [M + H]⁺ |
| 162 | 4-(3-chloro-5-methoxyphenoxy)-3-cyano-N-(5-fluoropyridin-2-yl)benzenesulfonamide | 3-chloro-5-methoxyphenol | m/z 434 [M + H]⁺ |
| 163 | 4-(4-bromophenoxy)-3-cyano-N-(5-fluoropyridin-2-yl)benzenesulfonamide (Reference Example) | 4-bromophenol | m/z 448 [M + H]⁺ |
| 164 | 4-[4-chloro-3-(propan-2-yl)phenoxy]-3-cyano-N-(5-fluoropyridin-2-yl)benzenesulfonamide | 4-chloro-3-(propan-2-yl)phenol | m/z 446 [M + H]⁺ |
| 165 | 3-cyano-4-(4-fluoro-3-methoxy-2-methylphenoxy)-N-(5-fluoropyridin-2-yl)benzenesulfonamide | 4-fluoro-3-methoxy-2-methylphenol | m/z 432 [M + H]⁺ |
| 166 | 3-cyano-4-(2-fluoro-5-methoxyphenoxy)-N-(5-fluoropyridin-2-yl)benzenesulfonamide | 2-fluoro-5-methoxyphenol | m/z 418 [M + H]⁺ |
| 167 | 4-(2-chloro-3,4-difluorophenoxy)-3-cyano-N-(5-fluoropyridin-2-yl)benzenesulfonamide | 2-chloro-3,4-difluorophenol | m/z 440 [M + H]⁺ |
| 168 | 4-(2-chloro-4-methoxyphenoxy)-3-cyano-N-(5-fluoropyridin-2-yl)benzenesulfonamide | 2-chloro-4-methoxyphenol | m/z 434 [M + H]⁺ |
| 169 | 4-(3-chloro-2,6-dimethylphenoxy)-3-cyano-N-(5-fluoropyridin-2-yl)benzenesulfonamide | 3-chloro-2,6-dimethylphenol | m/z 432 [M + H]⁺ |
| 170 | 3-cyano-4-(2,5-dichlorophenoxy)-N-(5-fluoropyridin-2-yl)benzenesulfonamide | 2,5-dichlorophenol | m/z 436 [M + H]⁺ |
| 171 | 4-(3-chloro-4,5-dimethylphenoxy)-3-cyano-N-(5-fluoropyridin-2-yl)benzenesulfonamide | 3-chloro-4,5-dimethylphenol | m/z 432 [M + H]⁺ |
| 172 | 3-cyano-4-(4-fluoro-2,3-dimethylphenoxy)-N-(5-fluoropyridin-2-yl)benzenesulfonamide | 4-fluoro-2,3-dimethylphenol | m/z 416 [M + H]⁺ |
| 173 | 3-cyano-4-(4-fluoro-2-methoxy-3-methylphenoxy)-N-(5-fluoropyridin-2-yl)benzenesulfonamide | 4-fluoro-2-methoxy-3-methylphenol | m/z 432 [M + H]⁺ |
| 174 | 3-cyano-N-(5-fluoropyridin-2-yl)-4-[2-methyl-5-(propan-2-yl)phenoxy]benzenesulfonamide | 2-methyl-5-(propan-2-yl)phenol | m/z 426 [M + H]⁺ |
| 175 | 4-(3-chloro-2,4-dimethylphenoxy)-3-cyano-N-(5-fluoropyridin-2-yl)benzenesulfonamide | 3-chloro-2,4-dimethylphenol | m/z 432 [M + H]⁺ |
| 176 | 4-(2-chloro-5-fluorophenoxy)-3-cyano-N-(5-fluoropyridin-2-yl)benzenesulfonamide | 2-chloro-5-fluorophenol | m/z 420 [M − H]⁻ |
| 177 | 4-(2-chloro-4,5-difluorophenoxy)-3-cyano-N-(5-fluoropyridin-2-yl)benzenesulfonamide | 2-chloro-4,5-difluorophenol | m/z 438 [M − H]⁻ |
| 178 | 4-(2-chloro-3,4-dimethylphenoxy)-3-cyano-N-(5-fluoropyridin-2-yl)benzenesulfonamide | 2-chloro-3,4-dimethylphenol | m/z 432 [M + H]⁺ |

Library Protocol 2

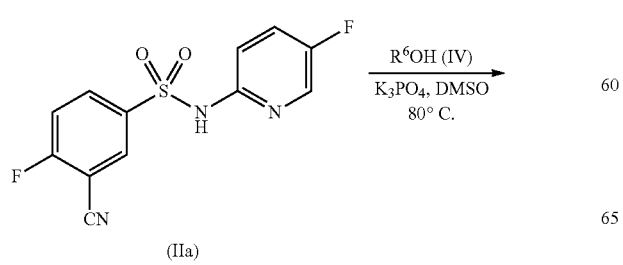

(IIa)

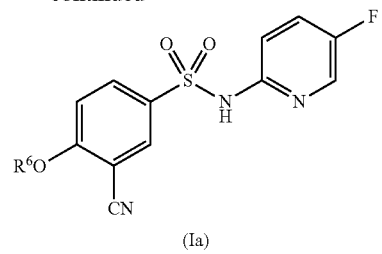

(Ia)

To a 0.2M solution of 3-cyano-4-fluoro-N-(5-fluoropyridin-2-yl)benzenesulfonamide in DMSO (Preparation 2, 500 uL, 100 umol) was added a 0.2M solution in DMSO of the appropriate phenol/hydroxypyridine (compound of formula (IV), 500 uL, 100 umol) followed by anhydrous $K_3PO_4$ (64 mg, 300 umol) and the reaction mixtures were stirred at 80° C. for 18 hours. The reaction mixtures were cooled and purified using one of the two preparative HPLC described below to afford the desired compounds of formula (Ia).
Preparative HPLC Method 1:
Mobile phase A: 10 mM ammonium acetate in water; Mobile phase B: MeCN
Column: Gemini NX C18 (20×100 mm, 5 u)
Gradient: Initial 10% B; 2 mins 40% B; 10 mins 70% B, 11-12 mins 95% B, 13-15 mins 10% B
Flow rate: 20 mL/min.
Preparative HPLC Method 2:
Mobile phase A: 0.1% formic acid in water; Mobile phase B: MeCN
Column: Zorbax SB C18 921×250 mm, 7 u)
Gradient: Initial 10% B; 3 mins 20% B; 18 mins 80% B, 19-20 mins 95% B, 22-25 mins 10% B,
Flow rate: 20 mL/min LCMS Conditions 1:
Mobile phase A: 0.05% formic acid in water; Mobile phase B: MeCN
Column: RESTEK C18 2.1×30 mm×3μ
Gradient: From 98% A and 2% B to 90% A and 10% B in 1 min, further to 2% A and 98% B in 2.0 min and finally back to initial condition in 3 min
Flow rate: 1.5 mL/min
LCMS Conditions 2:
Mobile phase A: 10 mM ammonium acetate in water; Mobile phase B: MeCN
Column: Zorbax Extend C18 (50×4.6 mm, 5 u)
Gradient: From 95% A and 5% B to 85% A and 15% B in 1.5 min, further to 10% A and 90% B in 3-4 min and finally back to initial condition in 5 min
Flow rate: 1.5 mL/min The compounds of the Examples in the table below were prepared from 3-cyano-4-fluoro-N-(5-fluoropyridin-2-yl)benzenesulfonamide in DMSO (Preparation 2) and the appropriate phenol or hydroxypyridine according to Library protocol 2.

| Ex | Name | $R^6OH$ | Data |
|---|---|---|---|
| 179 | 4-(3-chloro-2-cyanophenoxy)-3-cyano-N-(5-fluoropyridin-2-yl)benzenesulfonamide | 3-chloro-2-cyanophenol | m/z 429 [M + H]+ |
| 180 | 4-[(5-chloro-6-cyclopropylpyridin-3-yl)oxy]-3-cyano-N-(5-fluoropyridin-2-yl)benzenesulfonamide (Reference Example) | 5-chloro-6-cyclopropylpyridin-3-yl)ol (WO2012007869) | m/z 445 [M + H]+ |
| 181 | 3-cyano-N-(5-fluoropyridin-2-yl)-4-(3-methoxy-2-methylphenoxy)benzenesulfonamide | 3-methoxy-2-methylphenol | m/z 414 [M + H]+ |
| 182 | 3-cyano-N-(5-fluoropyridin-2-yl)-4-(3-methoxy-5-methylphenoxy)benzenesulfonamide | 3-methoxy-5-methylphenol | m/z 414 [M + H]+ |
| 183 | 3-cyano-4-(4-fluorophenoxy)-N-(5-fluoropyridin-2-yl)benzenesulfonamide | 4-fluorophenol | m/z 388 [M + H]+ |
| 184 | 3-cyano-N-(5-fluoropyridin-2-yl)-4-[(2-methylpyridin-3-yl)oxy]benzenesulfonamide | 2-methylpyridin-3-yl)ol | m/z 385 [M + H]+ |
| 185 | 3-cyano-N-(5-fluoropyridin-2-yl)-4-(3-methylphenoxy)benzenesulfonamide | 3-methylphenol | m/z 384 [M + H]+ |
| 186 | 3-cyano-N-(5-fluoropyridin-2-yl)-4-(2-methylphenoxy)benzenesulfonamide | 2-methylphenol | m/z 384 [M + H]+ |
| 187 | 3-cyano-N-(5-fluoropyridin-2-yl)-4-(pyridin-2-yloxy)benzenesulfonamide | 2-hydroxypyridine | m/z 371 [M + H]+ |
| 188 | 3-cyano-N-(5-fluoropyridin-2-yl)-4-(4-methoxyphenoxy)benzenesulfonamide | 4-methoxyphenol | m/z 400 [M + H]+ |
| 189 | 4-(2-bromophenoxy)-3-cyano-N-(5-fluoropyridin-2-yl)benzenesulfonamide (Reference Example) | 2-bromophenol | m/z 449 [M + H]+ |
| 190 | 3-cyano-N-(5-fluoropyridin-2-yl)-4-[(4-methoxypyridin-3-yl)oxy]benzenesulfonamide | (4-methoxypyridin-3-yl)ol | m/z 401 [M + H]+ |
| 191 | 3-cyano-N-(5-fluoropyridin-2-yl)-4-(4-methylphenoxy)benzenesulfonamide | 4-methylphenol | m/z 384 [M + H]+ |
| 192 | 3-cyano-4-[(2-ethyl-6-methylpyridin-3-yl)oxy]-N-(5-fluoropyridin-2-yl)benzenesulfonamide | (2-ethyl-6-methyl pyridin-3-yl)ol | m/z 413 [M + H]+ |
| 193 | 3-cyano-N-(5-fluoropyridin-2-yl)-4-[(6-methylpyridin-3-yl)oxy]benzenesulfonamide | (6-methylpyridin-3-yl)ol | m/z 385 [M + H]+ |
| 194 | 3-cyano-N-(5-fluoropyridin-2-yl)-4-(pyridin-3-yloxy)benzenesulfonamide | 3-hydroxypyridine | m/z 371 [M + H]+ |
| 195 | 3-cyano-N-(5-fluoropyridin-2-yl)-4-(3,4,5-trifluorophenoxy)benzenesulfonamide | 3,4,5-trifluorophenol | m/z 424 [M + H]+ |
| 196 | 3-cyano-N-(5-fluoropyridin-2-yl)-4-{[6-(trifluoromethyl)pyridin-3-yl]oxy}benzenesulfonamide | 6-(trifluoromethyl)pyridin-3-yl]ol | m/z 439 [M + H]+ |
| 197 | 3-cyano-4-(5-cyano-2-methoxyphenoxy)-N-(5-fluoropyridin-2-yl)benzenesulfonamide | 5-cyano-2-methoxyphenol | m/z 425 [M + H]+ |
| 198 | 3-cyano-N-(5-fluoropyridin-2-yl)-4-[(4-methylpyridin-3-yl)oxy]benzenesulfonamide | (4-methylpyridin-3-yl)ol | m/z 385 [M + H]+ |
| 199 | 3-cyano-N-(5-fluoropyridin-2-yl)-4-[(6-methoxypyridin-3-yl)oxy]benzenesulfonamide | (6-methoxypyridin-3-yl)ol | m/z 401 [M + H]+ |
| 200 | 3-cyano-N-(5-fluoropyridin-2-yl)-4-(5-methoxy-2-methylphenoxy)benzenesulfonamide | 5-methoxy-2-methylphenol | m/z 414 [M + H]+ |

| Ex | Name | R⁶OH | Data |
|---|---|---|---|
| 201 | 3-cyano-N-(5-fluoropyridin-2-yl)-4-(4-methoxy-2-methylphenoxy)benzenesulfonamide | 4-methoxy-2-methylphenol | m/z 414 [M + H]⁺ |
| 202 | 4-[(5-chloropyridin-3-yl)oxy]-3-cyano-N-(5-fluoropyridin-2-yl)benzenesulfonamide | 5-chloro-3-hydroxypyridine | m/z 405 [M + H]⁺ |
| 203 | 3-cyano-4-(4-cyano-3-cyclopropylphenoxy)-N-(5-fluoropyridin-2-yl)benzenesulfonamide (Reference Example) | 4-cyano-3-cyclopropylphenol | m/z 435 [M + H]⁺ |
| 204 | 3-cyano-4-(4-cyano-2-methoxyphenoxy)-N-(5-fluoropyridin-2-yl)benzenesulfonamide | 4-cyano-2-methoxyphenol | m/z 425 [M + H]⁺ |
| 205 | 3-cyano-4-[(6-cyanopyridin-3-yl)oxy]-N-(5-fluoropyridin-2-yl)benzenesulfonamide | 3-hydroxy-6-cyanopyridine | m/z 396 [M + H]⁺ |
| 206 | 3-cyano-4-[(5-cyanopyridin-3-yl)oxy]-N-(5-fluoropyridin-2-yl)benzenesulfonamide | 3-hydroxy-5-cyanipyridine | m/z 396 [M + H]⁺ |
| 207 | 3-cyano-N-(5-fluoropyridin-2-yl)-4-[2-(propan-2-yloxy)phenoxy]benzenesulfonamide | 2-(propan-2-yloxy)phenol | m/z 428 [M + H]⁺ |
| 208 | 3-cyano-N-(5-fluoropyridin-2-yl)-4-(3-methoxyphenoxy)benzenesulfonamide | 3-methoxyphenol | m/z 400 [M + H]⁺ |

Library Protocol 3

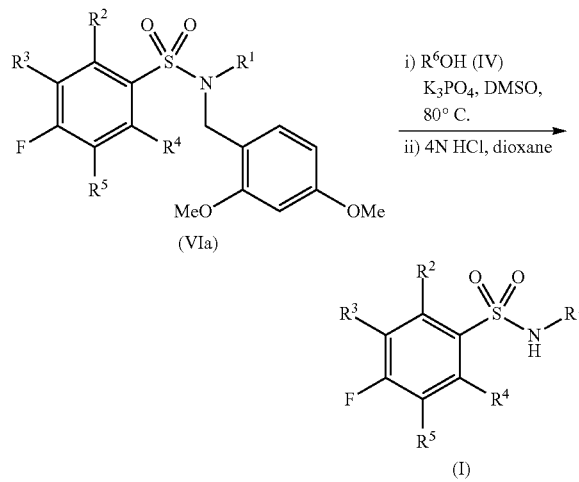

To a 0.2M solution in DMSO of the appropriate sulphonamide (compound of formula (VIa), 500 uL, 100 umol) was added a 0.2M solution in DMSO of the appropriate phenol/hydroxypyridine (compound of formula (IV), 500 uL, 100 umol) followed by anhydrous $K_3PO_4$ (64 mg, 300 umol) and the reaction mixtures were stirred at 80° C. for 18 hours. The reaction mixtures were concentrated in vacuo and treated with 4M HCl in dioxane (1 mL). The reaction mixtures were concentrated in vacuo and purified using preparative HPLC as described below to afford the desired compounds of formula (I).

Preparative HPLC Method:
Mobile phase A: 10 mM ammonium acetate in water; Mobile phase B: MeCN
Column: Sunfire C18 (19×150 mm, 5 u)
Gradient: Initial 10% B; 2 mins 30% B; 10 mins 60% B, 12-13 mins 95% B, 14-15 mins 10% B
Flow rate: 16 mL/min.

The compounds of the Examples in the table below were prepared from the appropriate sulphonamide of formula (VIa) and the appropriate phenol of formula (IV) according to Library Protocol 3.

| Ex | Name | Phenol & sulfonamide | Data |
|---|---|---|---|
| 209 | 3-cyano-4-(3-cyano-4-fluorophenoxy)-N-(pyrimidin-2-yl)benzenesulfonamide | 3-cyano-4-fluorophenol and 3-cyano-N-(2,4-dimethoxybenzyl)-4-fluoro-N-(pyrimidin-2-yl)benzenesulfonamide. | m/z 396 [M + H]⁺ |
| 210 | 5-chloro-4-(3,4-difluorophenoxy)-2-fluoro-N-(pyrimidin-2-yl)benzenesulfonamide | 3,4-difluorophenol and 5-chloro-N-(2,4-dimethoxybenzyl)-2,4-difluoro-N-(pyrimidin-2-yl)benzenesulfonamide (WO2012004743) | m/z 416 [M + H]⁺ |
| 211 | 3-cyano-4-(3,4-difluorophenoxy)-N-(pyrimidin-2-yl)benzenesulfonamide | 3,4-difluorophenol and 3-cyano-N-(2,4-dimethoxybenzyl)-4-fluoro-N-(pyrimidin-2-yl)benzenesulfonamide. | m/z 389 [M + H]⁺ |
| 212 | 5-chloro-4-(3,4-difluorophenoxy)-2-fluoro-N-(5-fluoropyrimidin-2-yl)benzenesulfonamide | 3,4-difluorophenol and 5-chloro-N-(2,4-dimethoxybenzyl)-2,4-difluoro-N-(5-fluoropyrimidin-2-yl)benzenesulfonamide (WO2012004706) | m/z 434 [M + H]⁺ |
| 213 | 5-chloro-4-(3-cyano-4-fluorophenoxy)-2-fluoro-N-(pyrimidin-2-yl)benzenesulfonamide | 3-cyano-4-fluorophenol and 5-chloro-N-(2,4-dimethoxybenzyl)-2,4-difluoro-N-(pyrimidin-2-yl)benzenesulfonamide (WO2012004743) | m/z 423 [M + H]⁺ |

-continued

| Ex | Name | Phenol & sulfonamide | Data |
|---|---|---|---|
| 214 | 5-chloro-4-(3-cyano-4-fluorophenoxy)-2-fluoro-N-(5-fluoropyrimidin-2-yl)benzenesulfonamide | 3-cyano-4-fluorophenol and 5-chloro-N-(2,4-dimethoxybenzyl)-2,4-difluoro-N-(5-fluoropyrimidin-2-yl)benzenesulfonamide (WO2012004706) | m/z 441 [M + H]+ |
| 215 | 5-chloro-4-(4-cyano-3-fluorophenoxy)-2-fluoro-N-(5-fluoropyridin-2-yl)benzenesulfonamide | 3-cyano-4-fluorophenol and 5-chloro-N-(2,4-dimethoxybenzyl)-2,4-difluoro-N-(5-fluoro-2-pyridinyl)benzenesulfonamide (WO2012004743) | m/z 440 [M + H]+ |

Library Protocol 4

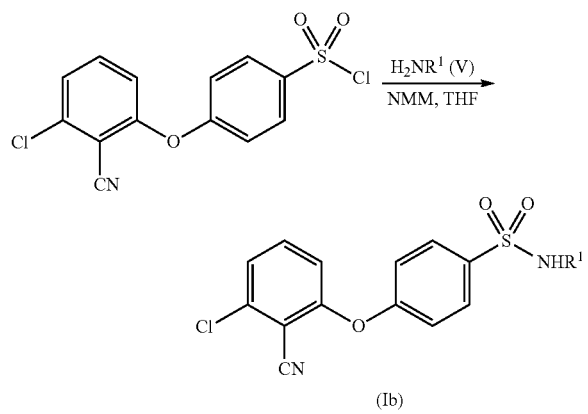

To a stock solution of the appropriate amine of formula (V) (1 mmol) in THF (5 mL) was added NMM (111 uL, 1 mmol).

An aliquot of this solution (50 uL, 10 umol) was added to a solution of 4-(3-chloro-2-cyanophenoxy)benzene-1-sulfonyl chloride (3.6 mg, 12 umol) in DCM (120 uL) and the reaction mixture stirred at room temperature for 24 hours. The reaction mixture was concentrated in vacuo to afford the desired compound of formula (Ib).

The compounds of the Reference Examples in the table below were prepared from 4-(3-chloro-2-cyanophenoxy)benzene-1-sulfonyl chloride (commercially available) and the appropriate amine of formula (V) according to Library Protocol 4. These compounds do not fall within the scope of formula (I).

Example 224

4-(4-aminophenoxy)-3-cyano-N-(5-fluoropyridin-2-yl)benzenesulfonamide

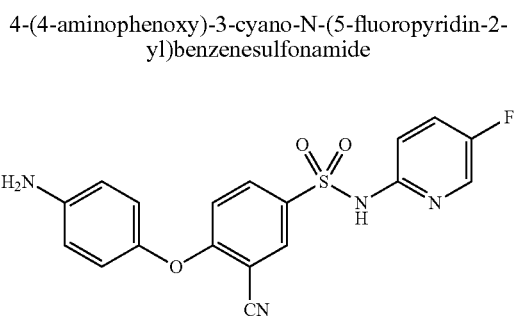

The title compound was prepared according to the method described for Library Protocol 2 using 3-cyano-4-fluoro-N-(5-fluoropyridin-2-yl)benzenesulfonamide (Preparation 2), 4-aminophenol.

MS m/z 385 [M+H]+

Example 225

5-chloro-4-(3-cyano-4-fluorophenoxy)-2-fluoro-N-(pyrimidin-2-yl)benzenesulfonamide

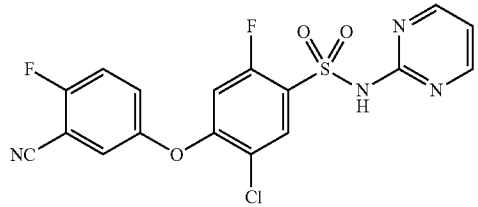 [SMILES: N#Cc1cc(Oc2cc(F)c(S(=O)(=O)Nc3ncccn3)cc2Cl)ccc1F]

| Ref Ex | Name | Amine |
|---|---|---|
| 216 | 4-(3-chloro-2-cyanophenoxy)-N-(4-methylpyridin-2-yl)benzenesulfonamide | 4-methyl-2-aminopyridine |
| 217 | 4-(3-chloro-2-cyanophenoxy)-N-(pyridin-4-yl)benzenesulfonamide | 4-aminopyridine |
| 218 | 4-(3-chloro-2-cyanophenoxy)-N-(pyridin-2-yl)benzenesulfonamide | 2-aminopyridine |
| 219 | 4-(3-chloro-2-cyanophenoxy)-N-(pyridin-3-yl)benzenesulfonamide | 3-aminopyridine |
| 220 | 4-(3-chloro-2-cyanophenoxy)-N-(4-methylpyrimidin-2-yl)benzenesulfonamide | 4-methyl-2-aminopyrimidine |
| 221 | 4-(3-chloro-2-cyanophenoxy)-N-(5-methylpyridin-2-yl)benzenesulfonamide | 5-methyl-2-aminopyridine |
| 222 | 4-(3-chloro-2-cyanophenoxy)-N-(pyrimidin-2-yl)benzenesulfonamide | 2-aminopyrimidine |
| 223 | 4-(3-chloro-2-cyanophenoxy)-N-(pyrazin-2-yl)benzenesulfonamide | 2-aminopyrazine |

The title compound was prepared according to the method described for Library Protocol 2 using 5-chloro-N-(2,4-dimethoxybenzyl)-2,4-difluoro-N-(pyrimidin-2-yl)benzenesulfonamide (WO2012004743) and 3-cyano-4-fluorophenol. MS m/z 423 [M+H]+

The compounds of the Examples in the table below were prepared from appropriate compounds of formulae (II) and (IV) according to the specified Method Variation (MV) and, as necessary, purified according to the specified Purification Method (PM).

| Ex | Name | Phenol and Sulfonamide | MS Data (MV, PM) |
|---|---|---|---|
| 226 | 5-chloro-4-(3-chloro-4-cyanophenoxy)-2-fluoro-N-(5-fluoropyrimidin-2-yl)benzenesulfonamide | 3-chloro-4-cyanophenol and 5-chloro-N-[(2,4-dimethoxyphenyl)methyl]-2,4-difluoro-N-(5-fluoro-2-pyrimidinyl)-benzene sulphonamide (WO 2012004706). | m/z 457 [M + H]+ MV 5 PM A |
| 227 | 5-chloro-4-(3-chloro-4-cyanophenoxy)-2-fluoro-N-(pyridazin-3-yl)benzenesulfonamide | 3-chloro-4-cyanophenol and 5-chloro-N-(2,4-dimethoxybenzyl)-2,4-difluoro-N-(pyridazin-3-yl)benzenesulfonamide (Prep 31). | m/z 439 [M + H]+ MV 5 PM B, D. |
| 228 | 3-chloro-4-(4-cyano-3-fluorophenoxy)-N-(5-fluoropyridin-2-yl)benzenesulfonamide | 3-fluoro-4-cyanophenol and 3-chloro-N-(2,4-dimethoxybenzyl)-4-fluoro-N-(5-fluoropyridin-2-yl)benzenesulfonamide (Prep 32). | m/z 422 [M + H]+ MV 5 PM A, B. |
| 229 | 4-(3-chloro-4-fluorophenoxy)-3-cyano-N-(4-cyanopyridin-2-yl)benzenesulfonamide | 3-chloro-4-fluorophenol and 3-cyano-N-(4-cyanopyridin-2-yl)-N-(2,4-dimethoxybenzyl)-4-fluorobenzenesulfonamide (Prep 36) | m/z 429 [M + H]+ MV 5 PM A. |
| 230 | 4-(3-chloro-4-fluorophenoxy)-3-cyano-N-(5-cyanopyridin-2-yl)benzenesulfonamide | 3-chloro-4-fluorophenol and 3-cyano-N-(5-cyanopyridin-2-yl)-N-(2,4-dimethoxybenzyl)-4-fluorobenzenesulfonamide (Prep 38) | m/z 429 [M + H]+ MV 5 PM A. |
| 231 | 4-((5-chloro-6-(difluoromethoxy)pyridin-3-yl)oxy)-3-cyano-N-(5-fluoropyridin-2-yl)benzenesulfonamide | 5-chloro-6-(difluoromethoxy)-3-pyridinol (WO 2012007869) and 3-cyano-4-fluoro-N-(5-fluoropyridin-2-yl)benzenesulfonamide (Preparation 2). | m/z 471 [M + H]+ MV 1 PM E. |
| 232 | 4-(3-chloro-4-cyanophenoxy)-N-(5-chloropyridin-2-yl)-3-cyanobenzenesulfonamide | 3-chloro-4-cyanophenol and 3-cyano-4-fluoro-N-(5-chloropyridin-2-yl)benzenesulfonamide (Preparation 39). | m/z 445 [M + H]+ MV 1 PM E. |
| 233 | 4-(3-chloro-4-cyanophenoxy)-3-cyano-N-(5-methylpyridin-2-yl)benzenesulfonamide | 3-chloro-4-cyanophenol and 3-cyano-4-fluoro-N-(5-methylpyridin-2-yl)benzenesulfonamide (Preparation 40). | m/z 425 [M + H]+ MV 1 PM A. |
| 234 | 3-cyano-N-(5-fluoropyridin-2-yl)-4-(4-(2-hydroxypropan-2-yl)phenoxy)benzenesulfonamide | 4-(hydroxypropan-2-yl)phenol (Preparation 45) and 3-cyano-4-fluoro-N-(5-fluoropyridin-2-yl)benzenesulfonamide (Preparation 2). | m/z 428 [M + H]+ MV 1 PM B. |
| 235 | 3-cyano-4-({4-cyano-3,5-bis[methyl-D3]-2,3-D2-phenyl}oxy)-N-(5-fluoropyridin-2-yl)benzenesulfonamide | 4-hydroxy-2,6-bis(methyl-D3)-3,5-D2-benzonitrile (Journal of Labelled Compounds and Radiopharmaceuticals (2009), 52, 10, 435-442) and 3-cyano-4-fluoro-N-(5-fluoropyridin-2-yl)benzenesulfonamide (Preparation 2). | m/z 431 [M + H]+ MV 1 PM B, C. |
| 236 | 5-bromo-4-({4-cyano-3,5-bis[methyl-D3]-2,3-D2-phenyl}oxy)-N-(5-fluoropyridin-2-yl)benzenesulfonamide | 4-hydroxy-2,6-bis(methyl-D3)-3,5-D2-benzonitrile (Journal of Labelled Compounds and Radiopharmaceuticals (2009), 52, 10, 435-442) and 5-bromo-N-(2,4-dimethoxybenzyl)-2,4-difluoro-N-(5-fluoropyridin-2-yl)benzenesulfonamide (Preparation 12). | m/z 504 [M + H]+ MV 5 No PM. |

-continued

| Ex | Name | Phenol and Sulfonamide | MS Data (MV, PM) |
|---|---|---|---|
| 237 | 4-(3-chloro-4-cyano-5-fluorophenoxy)-3-cyano-N-(5-fluoropyridin-2-yl)benzenesulfonamide | 2-chloro-6-fluoro-4-hydroxybenzonitrile (Prep 44) and 3-cyano-N-(2,4-dimethoxybenzyl)-4-fluoro-N-(5-fluoropyridin-2-yl)benzenesulfonamide (Prep 18) | m/z 445 [M − H]⁻ MV 5 PM A. |
| 238 | 4-((5-chloro-6-methylpyridin-3-yl)oxy)-3-cyano-N-(5-fluoropyridin-2-yl)benzenesulfonamide | 5-chloro-6-methylpyridin-3-ol (J. Med. Chem. (1977), 17 (2), 172-81) and 3-cyano-N-(2,4-dimethoxybenzyl)-4-fluoro-N-(5-fluoropyridin-2-yl)benzenesulfonamide (Prep 18). | m/z 419 [M + H]⁺ MV 5 PM A. |
| 239 | 4-{[5-chloro-6-(hydroxymethyl)pyridin-3-yl]oxy}-2-fluoro-N-(5-fluoropyridin-2-yl)benzenesulfonamide | 3-chloro-4-(hydroxymethyl)phenol and N-(2,4-dimethoxybenzyl)-2,4-difluoro-N-(5-fluoropyridin-2-yl)benzenesulfonamide (Prep 34). | m/z 428 [M + H]⁺ MV 5 PM B. |
| 240 | 4-(4-chloro-3-(hydroxymethyl)phenoxy)-3-cyano-N-(5-fluoropyridin-2-yl)benzenesulfonamide | 4-chloro-3-(hydroxymethyl)phenol and 3-cyano-N-(2,4-dimethoxybenzyl)-4-fluoro-N-(5-fluoropyridin-2-yl)benzenesulfonamide (Prep 18). | m/z 434 [M + H]⁺ MV 5 PM B. |

Example 241

3-cyano-4-(3,5-dichloro-4-cyanophenoxy)-N-(5-fluoropyridin-2-yl)benzenesulfonamide

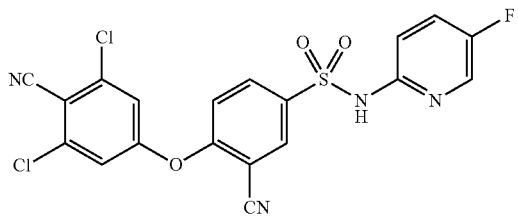 [SMILES: N#Cc1cc(S(=O)(=O)Nc2ccc(F)cn2)ccc1Oc1cc(Cl)c(C#N)c(Cl)c1]

The title compound was prepared according to the method described for Method Variation 5 using 3-cyano-N-(2,4-dimethoxybenzyl)-4-fluoro-N-(5-fluoropyridin-2-yl)benzenesulfonamide (Preparation 18) and 2,6-dichloro-4-hydroxybenzonitrile, and then purified using preparative HPLC.

¹H NMR (400 MHz, DMSO-d₆): δ ppm 6.58 (d, 1H), 7.13-7.21 (m, 2H), 7.58-7.59 (m, 2H), 7.78 (s, 1H), 7.94 (m, 1H), 8.12 (s, 1H).

LCMS Rt=3.29 minutes MS m/z no mass ion

Example 242

4-[(5-chloro-6-fluoropyridin-3-yl)oxy]-3-cyano-N-(5-fluoropyridin-2-yl)benzenesulfonamide

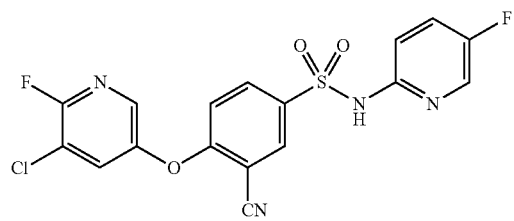 [SMILES: N#Cc1cc(S(=O)(=O)Nc2ccc(F)cn2)ccc1Oc1cnc(F)c(Cl)c1]

The title compound was prepared according to the method described for Method Variation 1 using 3-cyano-4-fluoro-N-(5-fluoropyridin-2-yl)benzenesulfonamide (Preparation 2) and 3-chloro-2-fluoro-5-hydroxypyridine and then purified using silica gel column chromatography eluting with 30-35% EtOAc in heptanes.

MS m/z 423 [M+H]⁺

Example 243

4-[(6-(azetidin-1-yl)-5-chloropyridin-3-yl)oxy]-3-cyano-N-(5-fluoropyridin-2-yl)benzenesulfonamide

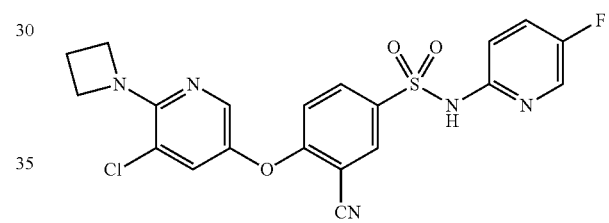

To a solution of 4-((5-chloro-6-fluoropyridin-3-yl)oxy)-3-cyano-N-(5-fluoropyridin-2-yl)benzenesulfonamide (Example 242, 200 mg, 0.47 mmol) in dimethylsulfoxide (2 mL) was added azetidine (54 mg, 0.94 mmol) followed by potassium carbonate (130 mg, 0.94 mmol) and the reaction was heated to 50° C. for 17 hours. The mixture was filtered and purified using preparative HPLC to afford the title compound.

¹H NMR (400 MHz, DMSO-d₆): δ ppm 2.08 (quintet, 2H), 3.98 (t, 4H), 6.84 (d, 1H), 6.90 (dd, 1H), 7.49 (dd, 1H), 7.65 (d, 1H), 7.88 (dd, 1H), 7.93 (d, 1H), 8.01 (d, 1H), 8.15 (d, 1H), 11.08 (br s, 1H).

MS m/z 459 [M+H]⁺

Example 244

4-[(5-chloro-6-(methylamino)pyridin-3-yl)oxy]-3-cyano-N-(5-fluoropyridin-2-yl)benzenesulfonamide

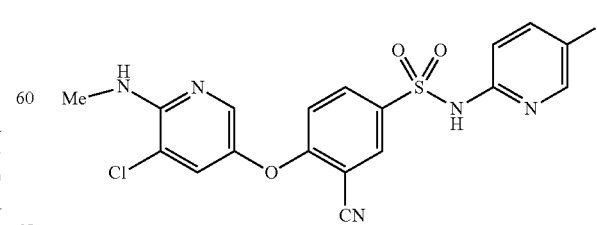

The title compound was prepared according to the method described for Example 243 using methylamine.

¹H NMR (400 MHz, DMSO-d₆): δ ppm 2.68 (d, 3H), 6.54 (q, 1H), 6.83 (d, 1H), 6.90 (dd, 1H), 7.49 (dt, 1H), 7.62 (d, 1H), 7.85-7.88 (m, 2H), 8.01 (d, 1H), 8.14 (d, 1H), 11.07 (br s, 1H).
MS m/z 433 [M+H]⁺

Example 245

4-{[5-chloro-6-(dimethylamino)pyridin-3-yl]oxy}-3-cyano-N-(5-fluoropyridin-2-yl)benzenesulfonamide

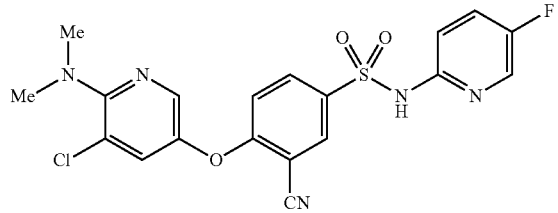 [SMILES: CN(C)c1ncc(Oc2ccc(S(=O)(=O)Nc3ccc(F)cn3)cc2C#N)cc1Cl]

The title compound was prepared according to the method described for Example 243 using dimethylamine.
¹H NMR (400 MHz, d₄-MeOH): δ ppm 3.00 (s, 6H), 6.99 (d, 1H), 7.16 (dd, 1H), 7.52 (dt, 1H), 7.68 (d, 1H), 8.06-8.11 (m, 3H), 8.31 (d, 1H).
MS m/z 447 [M+H]⁺

Example 246

4-[(6-amino-5-chloropyridin-3-yl)oxy]-3-cyano-N-(5-fluoropyridin-2-yl)benzenesulfonamide

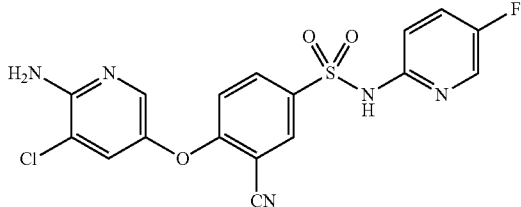 [SMILES: N#Cc1cc(S(=O)(=O)Nc2ccc(F)cn2)ccc1Oc1cnc(N)c(Cl)c1]

The method described by Example 243 was followed, but using dimethoxybenzylamine instead of azetidine and with heating to 70° C. followed by stirring the residue in TFA (12 mL) for 1 hour. The resulting mixture was concentrated in vacuo and purified using reverse phase column chromatography eluting from 5% to 80% MeCN (0.1% HCO₂H) in water (0.1% HCO₂H) to afford the title compound.
¹H NMR (400 MHz, d₄-MeOH): δ ppm 6.97 (d, 1H), 7.16 (dd, 1H), 7.50-7.55 (m, 1H), 7.61 (d, 1H), 7.86 (d, 1H), 8.07 (d, 1H), 8.09 (dd, 1H), 8.29 (d, 1H).
MS m/z 419 [M+H]⁺

Example 247

4-[3-chloro-4-(hydroxymethyl)phenoxy]-3-cyano-N-(5-fluoropyridin-2-yl)benzenesulfonamide

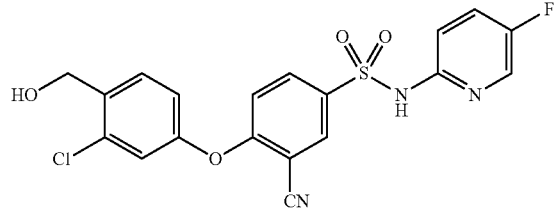 [SMILES: N#Cc1cc(S(=O)(=O)Nc2ccc(F)cn2)ccc1Oc1ccc(CO)c(Cl)c1]

To a stirred solution of 3-chloro-4-(hydroxymethyl)phenol (120 mg, 0.54 mmol) and 3-cyano-N-(2,4-di methoxybenzyl)-4-fluoro-N-(5-fluoropyridin-2-yl)benzenesulfonamide (Preparation 18, 100 mg, 0.22 mmol) in DMSO (1.5 mL) was added potassium carbonate (78 mg, 0.56 mmol) and the reaction stirred at room temperature for 72 hours. Water (10 mL) and EtOAc (15 mL) were added and the layers separated. The aqueous phase was extracted with EtOAc. The combined organic extracts were washed with brine, dried over magnesium sulphate and concentrated in vacuo. The crude product was purified by silica gel column chromatography eluting with 3:2 EtOAc:heptanes. The residue (76 mg, 0.13 mmol) was dissolved in DCM (2 mL) and treated with TFA (2 mL). The reaction was stirred at room temperature for 18 hours. MeOH (1 mL) was added and the reaction concentrated in vacuo. The crude product was purified by silica gel column chromatography eluting with 10-30% EtOAc in DCM to afford the title compound (25 mg, 44%) as a colourless solid (25 mg, 44%).
¹H NMR (400 MHz, CDCl₃): δ ppm 4.56 (d, 2H), 5.48 (t, 1H), 7.02 (d, 1H), 7.08 (dd, 1H), 7.28 (d, 1H), 7.46 (s, 1H), 7.62-7.72 (m, 2H), 8.08 (d, 1H), 8.20 (s, 1H), 8.36 (s, 1H), 11.24 (br s, 1H).
MS m/z 434 [M+H]⁺

Example 248

4-(3-chloro-4-cyanophenoxy)-3-cyano-5-fluoro-N-(5-fluoropyridin-2-yl)benzenesulfonamide

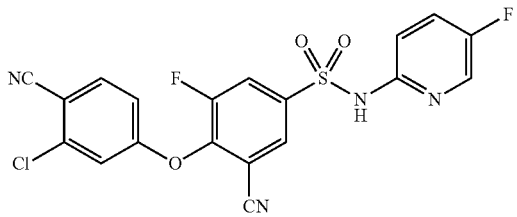 [SMILES: N#Cc1ccc(Oc2c(F)cc(S(=O)(=O)Nc3ccc(F)cn3)cc2C#N)cc1Cl]

To a solution of 3-cyano-4-(4-cyano-3-fluorophenoxy)-5-fluorobenzene-1-sulfonyl chloride (Preparation 43, 27 mg, 0.153 mmol) in DCM (5 mL) was added 5-fluoro-2-aminopyridine (26 mg, 0.230 mmol) followed by pyridine (36 mg, 0.459 mmol, 0.037 mL) and the reaction was stirred at room temperature for 18 hours. The reaction was diluted with DCM (20 mL) and water (30 mL). The organic layer was separated and the aqueous re-extracted with DCM (2×30 mL). The combined organic layers were dried over sodium sulfate, filtered and concentrated in vacuo. The residue was purified by reverse phase chromatography eluting with (acetonitrile/0.1% formic acid) and (water/0.1% formic acid), gradient 5% to 60% to afford the title compound as colourless solid (21 mg, 31%).
¹H NMR (400 MHz, Acetone-d₆): δ ppm 7.29-7.34 (m, 2H), 7.53 (d, 1H), 7.60-7.65 (m, 1H), 7.95 (d, 1H), 8.18 (d, 1H), 8.29 (dd, 1H), 8.34 (m, 1H).
MS m/z 447 [M+H]⁺

Example 249

4-({4-cyano-3,5-bis[methyl-D₃]-2,3-D₂-phenyl}oxy)-N-(5-fluoropyridin-2-yl)benzenesulfonamide

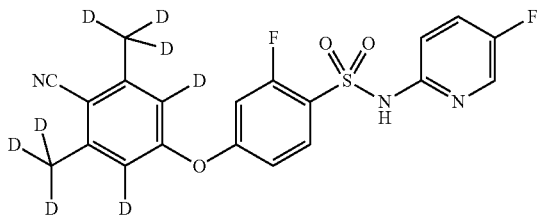 [SMILES: [2H]c1c(Oc2ccc(S(=O)(=O)Nc3ccc(F)cn3)c(F)c2)c([2H])c(C([2H])([2H])[2H])c(C#N)c1C([2H])([2H])[2H]]

To a degassed mixture of lithium chloride (42 mg, 1 mmol) in tetrahydrofuran (2 mL) was added tetrakis-(triphenylphosphine)palladium (0) (12 mg, 0.01 mmol) followed by a degassed solution of 5-bromo-4-({4-cyano-3,5-bis[methyl-$D_3$]-2,3-$D_2$-phenyl}oxy)-N-(5-fluoropyridin-2-yl)benzenesulfonamide (Example 236, 100 mg, 0.20 mmol) in tetrahydrofuran (2 mL) and triethylsilane (26 mg, 0.22 mmol). The reaction mixture was heated under reflux for 17 hours. An additional aliquot of tetrakis-(triphenylphosphine)palladium (0) (12 mg, 0.01 mmol), followed by another aliquot of triethylsilane (26 mg, 0.22 mmol), were added and the mixture heated under reflux for a further 24 hours. The reaction was cooled, diluted with ethyl acetate (20 mL), and washed with saturated aqueous ammonium chloride solution (20 mL), water (50 mL) and brine (10 mL). The organic layer was concentrated in vacuo and the residue purified using preparative HPLC to afford the title compound (21 mg, 25%).

$^1$H NMR (400 MHz, DMSO-$d_6$): δ ppm 6.99 (dd, 1H), 7.05 (dd, 1H), 7.14 (dd, 1H), 7.67 (dt, 1H), 7.92 (t, 1H), 8.14 (d, 1H), 11.41 (br s, 1H).

MS m/z 424 [M+H]$^+$

The compounds of formula (I) that follow may be prepared by procedures described in the aforementioned: Schemes; General Methods and Method Variations, as further illustrated by the Examples and corresponding Preparations; or by processes similar thereto.

5-Chloro-4-(3-cyano-4-fluorophenoxy)-2-fluoro-N-(pyridazin-3-yl)benzenesulfonamide.
5-Chloro-4-(3-chloro-4-cyanophenoxy)-2-fluoro-N-(pyrimidin-2-yl)benzenesulfonamide.
4-(3-Chloro-4-cyanophenoxy)-3-cyano-N-(5-cyanopyridin-2-yl)benzenesulfonamide.
4-(4-Cyano-3-fluorophenoxy)-N-(5-fluoropyridin-2-yl)-2-(trifluoromethyl)benzenesulfonamide.
3-Cyano-4-[4-cyano-3-(trifluoromethoxy)phenoxy]-N-(5-fluoropyridin-2-yl)benzenesulfonamide.
3-Cyano-4-[4-cyano-3-(difluoromethoxy)phenoxy]-N-(5-fluoropyridin-2-yl)benzenesulfonamide.
3-Cyano-4-[4-cyano-3-(difluoromethyl)phenoxy]-N-(5-fluoropyridin-2-yl)benzenesulfonamide.
3-Cyano-4-[4-cyano-3-(cyclopropyloxy)phenoxy]-N-(5-fluoropyridin-2-yl)benzenesulfonamide.
3-Cyano-4-[3-cyano-4-(trifluoromethoxy)phenoxy]-N-(5-fluoropyridin-2-yl)benzenesulfonamide.
3-Cyano-4-[3-cyano-4-(difluoromethoxy)phenoxy]-N-(5-fluoropyridin-2-yl)benzenesulfonamide.
3-Cyano-4-[3-cyano-4-(trifluoromethyl)phenoxy]-N-(5-fluoropyridin-2-yl)benzenesulfonamide.
3-Cyano-4-[3-cyano-4-(difluoromethyl)phenoxy]-N-(5-fluoropyridin-2-yl)benzenesulfonamide.
3-Cyano-4-[3-cyano-4-(cyclopropyloxy)phenoxy]-N-(5-fluoropyridin-2-yl)benzenesulfonamide.
3-Cyano-4-(3-cyano-5-fluorophenoxy)-N-(5-fluoropyridin-2-yl)benzenesulfonamide.
3-Cyano-4-(2-cyano-3-fluorophenoxy)-N-(5-fluoropyridin-2-yl)benzenesulfonamide.
3-Cyano-4-(2-cyano-5-fluorophenoxy)-N-(5-fluoropyridin-2-yl)benzenesulfonamide.
3-Cyano-4-(2-cyano-6-fluorophenoxy)-N-(5-fluoropyridin-2-yl)benzenesulfonamide.
3-Cyano-4-(4-cyano-3,5-difluorophenoxy)-N-(5-fluoropyridin-2-yl)benzenesulfonamide.
3-Cyano-4-[4-cyano-3-(2,2,2-trifluoroethyl)phenoxy]-N-(5-fluoropyridin-2-yl)benzenesulfonamide.
3-Cyano-4-(4-cyano-3-ethylphenoxy)-N-(5-fluoropyridin-2-yl)benzenesulfonamide.
3-Cyano-4-[4-cyano-3-(propan-2-yl)phenoxy]-N-(5-fluoropyridin-2-yl)benzenesulfonamide.
3-Cyano-4-[3-cyano-4-(hydroxymethyl)phenoxy]-N-(5-fluoropyridin-2-yl)benzenesulfonamide.
3-Cyano-4-[4-cyano-3-(hydroxymethyl)phenoxy]-N-(5-fluoropyridin-2-yl)benzenesulfonamide.
4-[4-Chloro-3-(hydroxymethyl)phenoxy]-3-cyano-N-(5-fluoropyridin-2-yl)benzenesulfonamide.
4-(3-Chloro-4-cyano-2-fluorophenoxy)-3-cyano-N-(5-fluoropyridin-2-yl)benzenesulfonamide.
4-(3-Chloro-4-cyano-2-methoxyphenoxy)-3-cyano-N-(5-fluoropyridin-2-yl)benzenesulfonamide.
4-(5-Chloro-4-cyano-2-fluorophenoxy)-3-cyano-N-(5-fluoropyridin-2-yl)benzenesulfonamide.
4-(5-Chloro-4-cyano-2-methoxyphenoxy)-3-cyano-N-(5-fluoropyridin-2-yl)benzenesulfonamide.
4-(4-Chloro-3-cyano-2-fluorophenoxy)-3-cyano-N-(5-fluoropyridin-2-yl)benzenesulfonamide.
4-(4-Chloro-3-cyano-2-methoxyphenoxy)-3-cyano-N-(5-fluoropyridin-2-yl)benzenesulfonamide.
4-(4-Chloro-5-cyano-2-fluorophenoxy)-3-cyano-N-(5-fluoropyridin-2-yl)benzenesulfonamide.
4-(4-Chloro-5-cyano-2-methoxyphenoxy)-3-cyano-N-(5-fluoropyridin-2-yl)benzenesulfonamide.
4-(3-Chloro-4-cyanophenoxy)-3-cyano-N-(5-fluoropyridin-2-yl)-5-methylbenzenesulfonamide.
3-Chloro-4-(3-chloro-4-cyanophenoxy)-5-cyano-N-(5-fluoropyridin-2-yl)benzenesulfonamide.

Preparation 1

5-bromo-4-(4-cyano-3-fluorophenoxy)-N-(2,4-dimethoxybenzyl)-2-fluoro-N-(5-fluoropyridin-2-yl)benzenesulfonamide

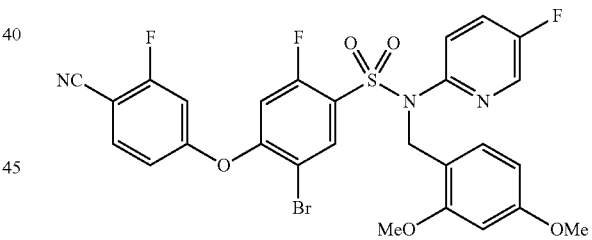

To a solution of 5-bromo-N-(2,4-dimethoxybenzyl)-2,4-difluoro-N-(5-fluoropyridin-2-yl)benzenesulfonamide (Preparation 12, 425 mg, 0.90 mmol) in DMSO (5 mL) was added $K_2CO_3$ (372 g, 2.70 mmol) followed by 2-fluoro-4-hydroxybenzonitrile (123 g, 0.90 mmol). The reaction mixture was left to stir at room temperature for 18 hours. To the reaction mixture was added water (20 mL) and saturated brine (20 mL) and the product was extracted with EtOAc (50 mL). The organic layer was retained and washed with saturated brine (3×40 mL), dried over $MgSO_4$, and the solvent removed under vacuum. The residue was purified using silica gel column chromatography eluting with 15% EtOAc in heptanes followed by trituration with heptane to afford the title compound as a colourless solid (74 mg, 28%).

$^1$H NMR (400 MHz, CDCl$_3$): δ ppm 3.68 (s, 3H), 3.76 (s, 3H), 5.00 (s, 2H), 6.34-6.38 (m, 2H), 6.82-6.86 (m, 3H), 7.17 (d, 1H), 7.30-7.35 (m, 2H), 7.66 (dd, 1H, 8.12 (d, 1H), 8.17 (d, 1H).

$^{19}$F NMR (376 MHz, CDCl$_3$) δ ppm −101.9 (m, 1F), −104.1 (m, 1F), −128.5 (m, 1F).

Preparation 2

3-cyano-4-fluoro-N-(5-fluoropyridin-2-yl)benzenesulfonamide

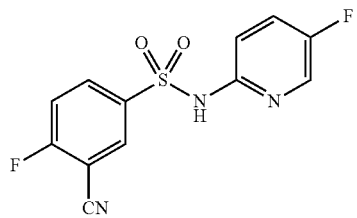 [SMILES: N#Cc1cc(S(=O)(=O)Nc2ccc(F)cn2)ccc1F]

3-Cyano-4-fluorobenzene-1-sulfonyl chloride (25 g, 114 mmol) was added to a solution of 5-fluoropyridin-2-amine (16.85 g, 150 mmol) and pyridine (23.7 g, 300 mmol) in dichloromethane (500 mL) at room temperature. The resulting mixture was stirred at room temperature for 3 hours. After evaporating the solvent the solid was stirred in diluted aqueous hydrochloric acid (2N, 400 mL) for 16 hours. The reaction mixture was filtered, washed with water (200 mL) and dried under high vacuum to afford the title compound as an orange solid (30.9 g, 98%).

$^1$H NMR (400 MHz, DMSO-d$_6$): δ ppm 7.09 (dd, 1H), 7.65-7.77 (m, 2H), 8.18 (d, 1H), 8.22-8.29 (m, 1H), 8.44 (dd, 1H)), 10.82 (br s, 1H).
MS m/z 296 [M+H]$^+$ Preparation 3

3-cyano-4-fluoro-N-(pyridin-2-yl)benzenesulfonamide

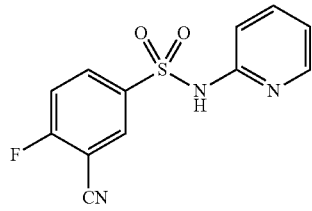 [SMILES: N#Cc1cc(S(=O)(=O)Nc2ccccn2)ccc1F]

The title compound was prepared according to the method described for Preparation 2 using 2-aminopyridine.
$^1$H NMR (400 MHz, DMSO-d$_6$): δ ppm 6.85 (t, 1H), 7.25 (d, 1H), 7.65 (t, 1H), 7.75-7.83 (m, 1H), 7.93 (d, 1H), 8.19 (ddd, 1H), 8.35 (dd, 1H).
MS m/z 278 [M+H]$^+$ Preparation 4

3-cyano-4-fluoro-N-(pyrazin-2-yl)benzenesulfonamide

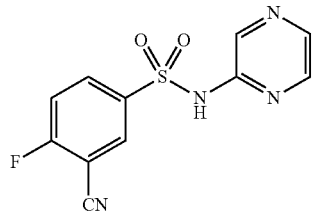

The title compound was prepared according to the method described for Preparation 2 using 2-aminopyrazine.
$^1$H NMR (400 MHz, DMSO-d$_6$): δ ppm 7.75 (t, 1H), 8.23 (m, 1H), 8.26-8.27 (m, 1H), 8.32-8.36 (m, 2H), 8.53 (dd, 1H).

Preparation 5

3-cyano-4-fluoro-N-(pyridin-3-yl)benzenesulfonamide

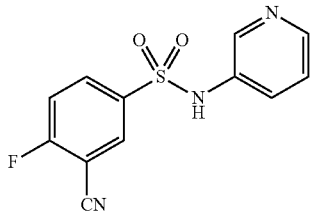 [SMILES: N#Cc1cc(S(=O)(=O)Nc2cccnc2)ccc1F]

The title compound was prepared according to the method described for Preparation 2 using 2-aminopyrazine.
MS m/z 278 [M+H]$^+$ Preparation 6

3-Cyano-4-fluoro-N-(pyridazin-3-yl)benzenesulfonamide

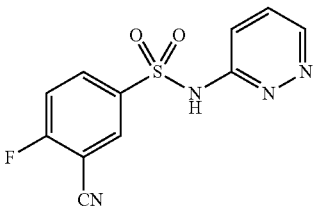 [SMILES: N#Cc1cc(S(=O)(=O)Nc2cccnn2)ccc1F]

To a solution of 3-cyano-4-fluorobenzenesulfonyl chloride (11.55 g, 52.63 mmol) in anhydrous acetonitrile (250 mL) was added pyridazin-3-amine (5 g, 52.63 mmol) followed by DABCO (5.9 g, 52.63 mmol) at 0° C. The reaction was stirred at room temperature for 18 hours, and then filtered. The filtrate was concentrated in vacuo and purified using silica gel column chromatography to afford the title compound (4.5 g, 30%)

$^1$H NMR (400 MHz, DMSO-d$_6$): δ ppm 7.61-7.71 (m, 2H), 7.87-7.92 (m, 1H), 8.16 (m, 1H), 8.32-8.37 (m, 2H), 14.61 (s, 1H).

Preparation 7

3-Cyano-4-fluoro-N-(pyrimidin-5-yl)benzenesulfonamide

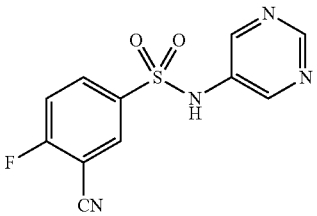 [SMILES: N#Cc1cc(S(=O)(=O)Nc2cncnc2)ccc1F]

The title compound was prepared according to the method described for Preparation 2 using 5-aminopyrimidine.
MS m/z 277 [M−H]$^−$ Preparation 8

3-Cyano-4-fluoro-N-(pyridazin-4-yl)benzene-sulfonamide

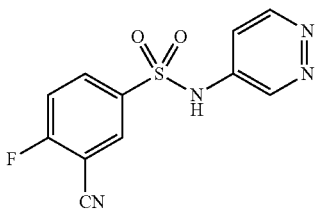 [SMILES: N#Cc1cc(S(=O)(=O)Nc2ccnnc2)ccc1F]

The title compound was prepared according to the method described for Preparation 6 using 4-aminopyridazine.
$^1$H NMR (400 MHz, DMSO-$d_6$): δ ppm 7.29 (dd, 1H), 7.66 (t, 1H), 8.19 (ddd, 1H), 8.34 (d, 1H), 8.39 (dd, 1H), 8.57 (d, 1H).

Preparation 9

3-cyano-4-fluoro-N-(pyridin-3-yl)benzenesulfonamide

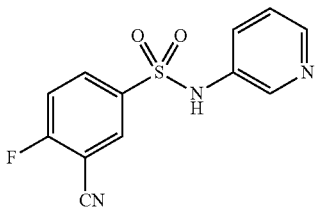 [SMILES: N#Cc1cc(S(=O)(=O)Nc2cccnc2)ccc1F]

The title compound was prepared according to the method described for Preparation 2 using 4-aminopyridazine.
MS m/s 276 [M−H]$^-$ Preparation 10

3-cyano-4-fluoro-N-(methoxymethyl)-N-(pyridazin-3-yl)benzenesulfonamide

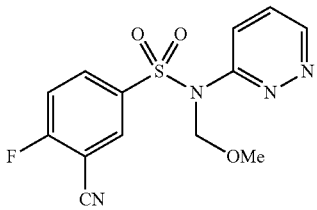 [SMILES: COCN(c1cccnn1)S(=O)(=O)c1ccc(F)c(C#N)c1]

To a solution of 3-cyano-4-fluoro-N-(pyridazin-3-yl)benzenesulfonamide (Preparation 6, 6.70 g, 24.1 mmol) in DCM (150 mL) at 0° C. was added DIPEA (6.48 mL, 35.18 mmol) followed by chloromethoxymethane (1.46 mL, 25.54 mmol) and the reaction mixture was stirred at room temperature for 2 hours. The reaction mixture was quenched by the addition of 1N NaOH (aq) solution, the organic layer was collected, washed with water, brine, and dried over Na$_2$SO$_4$ before concentrating in vacuo. The residue was purified using silica gel column chromatography eluting with EtOAc:Heptane 1:1 to afford the title compound as a mixture of isomers (3.85 g, 49%) that was used without further purification.
MS m/z 323 [M+H]$^+$ Preparation 11

5-cyano-N-(2,4-dimethoxybenzyl)-2,4-difluoro-N-(pyrimidin-4-yl)benzenesulfonamide

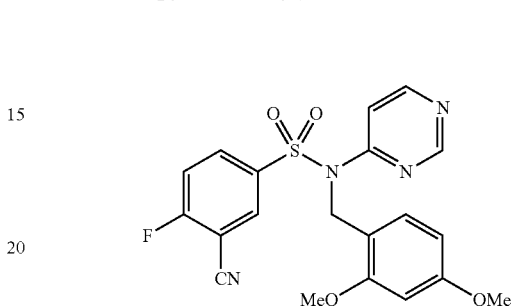

N-(2,4-Dimethoxybenzyl)pyrimidin-4-amine (WO2012004743, 0.70 g, 2.86 mmol), 3-cyano-4-fluorobenzene-1-sulfonyl chloride (0.75 g, 3.43 mmol) and 1,4-diazabicyclo[2.2.2]octane (0.39 g, 3.43 mmol) in acetonitrile (15 mL) were stirred at room temperature for 18 hours. The reaction mixture was diluted with dichloromethane (100 mL), washed with water (100 mL), the organic layer was dried over anhydrous magnesium sulphate and the filtrate was concentrated in vacuo. The residue was purified by silica gel column chromatography eluting with 10% dichloromethane in ethyl acetate to afford the title compound as a yellow glass (0.69 g, 57%).
$^1$HNMR (400 MHz, CDCl$_3$): δ ppm 3.59 (s, 3H), 3.80 (s, 3H), 5.15 (s, 2H), 6.35 (d, 1H), 6.45-6.43 (m, 1H), 7.17-7.10 (m, 2H), 7.30 (t, 1H), 8.00-7.98 (m, 1H), 8.23-8.19 (m, 1H), 8.55 (d, 1H), 8.87 (s, 1H).
$^{19}$F NMR (376 MHz, CDCl$_3$): δ ppm −98.30

Preparation 12

5-bromo-N-(2,4-dimethoxybenzyl)-2,4-difluoro-N-(5-fluoropyridin-2-yl)benzenesulfonamide

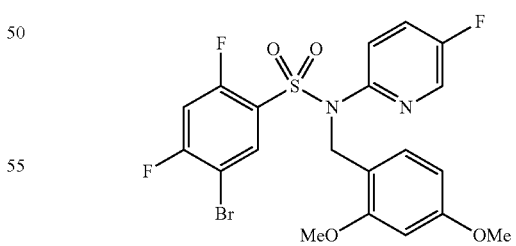

The title compound was prepared according to the method described for Preparation 11 using N-(2,4-dimethoxybenzyl)-5-fluoropyridin-2-amine (Preparation 20).
$^1$H NMR (400 MHz, CDCl$_3$): δ ppm 3.65 (s, 3H), 3.76 (3, 3H), 4.99 (s, 2H), 6.32-6.36 (m, 2H), 6.97 (dd, 1H), 7.16 (dd, 1H), 7.28-7.38 (m, 2H), 8.02 (t, 1H), 8.17 (s, 1H).
$^{19}$F NMR (376 MHz, CDCl$_3$): δ ppm −128 (s, 1F), −104 (s, 1F), −94 (s, 1F).

Preparation 13

N-2,4-dimethoxybenzyl-2,4,5-trifluoro-N-(5-fluoro-pyridin-2-yl)benzenesulfonamide

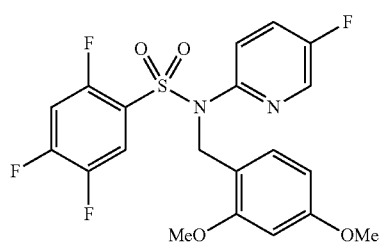 [SMILES: COc1ccc(CN(c2ccc(F)cn2)S(=O)(=O)c2cc(F)c(F)cc2F)c(OC)c1]

The title compound may be prepared according to the method described for Preparation 11 using 2,4,5-trifluorobenzenesulfonyl chloride and N-2,4-dimethoxybenzyl-5-fluoropyridin-2-amine (WO2012004743).

$^1$H NMR (400 MHz, CDCl$_3$): δ ppm 3.65 (s, 3H), 3.76 (3, 3H), 4.99 (s, 2H), 6.32-6.36 (m, 2H), 6.97 (dd, 1H), 7.16 (dd, 1H), 7.28-7.38 (m, 2H), 8.02 (t, 1H), 8.17 (s, 1H).

Preparation 14

3-cyano-N-(2,4-dimethoxybenzyl)-4-fluoro-N-(pyridazin-3-yl)benzenesulfonamide

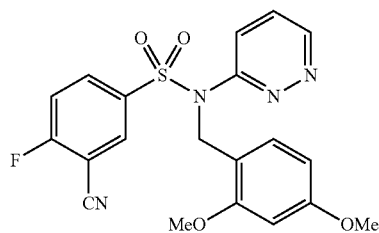 [SMILES: COc1ccc(CN(c2cccnn2)S(=O)(=O)c2ccc(F)c(C#N)c2)c(OC)c1]

To a suspension of N-(2,4-dimethoxybenzyl)pyridazin-3-amine (Preparation 19, 1.0 g, 4.00 mmol) in THF (15 mL) at −20° C. was slowly added LiHMDS (1M, 4.0 mL, 4.00 mmol). The reaction mixture was left to stir at −20° C. for 30 minutes and then cooled to −78° C. To the reaction mixture was slowly added 3-cyano-4-fluorobenzene-1-sulfonyl chloride (0.8 g, 3.64 mmol) suspended in THF (15 mL). The reaction mixture was slowly warmed to room temperature and left at room temperature for 18 hours. To the vessel was added saturated aqueous NH$_4$Cl solution (30 mL) and the product was extracted with EtOAc (25 mL). The organic layer was washed with saturated brine (40 mL), dried over MgSO$_4$, and the solvent removed under vacuum. The residue was purified using silica gel column chromatography eluting with 70% EtOAc in heptanes to afford the title compound as an orange oil (561 mg, 36%).

$^1$H NMR (400 MHz, CDCl$_3$): δ ppm 3.54 (s, 3H), 3.76 (s, 3H), 5.01 (s, 2H), 6.28 (d, 1H), 6.36 (dd, 1H), 7.16 (d, 1H), 7.32 (t, 1H), 7.48 (m, 2H), 7.94 (dd, 1H), 8.09 (ddd, 1H), 9.03 (dd, 1H).

$^{19}$F NMR (376 MHz, MeOD): δ ppm −98.8

Preparation 15

3-cyano-N-(2,4-dimethoxybenzyl)-4-fluoro-N-(5-fluoropyrimidin-2-yl)benzenesulfonamide

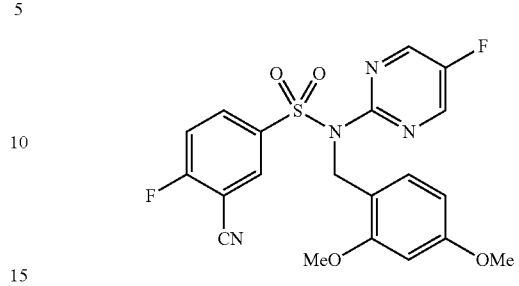

The title compound was prepared according to the method described for Preparation 14 using N-(2,4-dimethoxybenzyl)-5-fluoropyrimidin-2-amine (WO2012004706).

$^1$H NMR (400 MHz, CDCl$_3$): δ ppm 3.30 (s, 3H), 3.81 (s, 3H), 5.38 (s, 2H), 6.23 (d, 1H), 6.46 (dd, 1H), 7.15-7.20 (m, 2H), 7.77 (dd, 1H), 8.14 (m, 1H), 8.23 (s, 2H).

Preparation 16

N-3,4-dimethoxybenzyl-3,4-di-fluoro-N-(5-fluoropyridin-2-yl)benzenesulfonamide

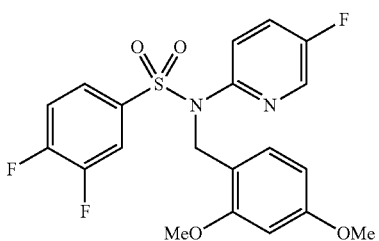 [SMILES: COc1ccc(CN(c2ccc(F)cn2)S(=O)(=O)c2ccc(F)c(F)c2)c(OC)c1]

The title compound was prepared according to the method described for Preparation 14 using 3,4,-difluorobenzenesulfonyl chloride and N-2,4-dimethoxybenzyl-5-fluoropyridin-2-amine (WO2012004743).

$^1$H NMR (400 MHz, CDCl$_3$): δ ppm 3.64 (s, 3H), 3.75 (s, 3H), 4.82 (s, 2H), 6.36 (m, 2H), 7.22 (d, 1H), 7.27 (m, 1H), 7.38 (m, 2H), 7.46 (m, 1H), 7.53 (m, 1H), 8.18 (d, 1H).

Preparation 17

3-cyano-N-(2,4-dimethoxybenzyl)-4-fluoro-N-(pyrimidin-2-yl)benzenesulfonamide

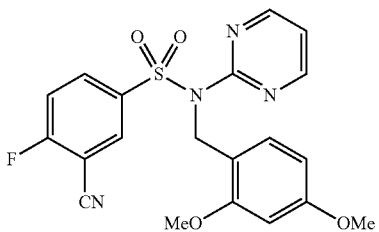 [SMILES: COc1ccc(CN(c2ncccn2)S(=O)(=O)c2ccc(F)c(C#N)c2)c(OC)c1]

The title compound was prepared according to the method described for Preparation 14 using NaHMDS and N-(2,4-dimethoxybenzyl)-2-pyrimidinamine (WO2012004743) at −50° C. The residue was triturated with EtOAc:Heptane 1:1 followed by acetone.

$^1$H NMR (400 MHz, CDCl$_3$): δ ppm 3.28 (s, 3H), 3.82 (s, 3H), 4.42 (s, 2H), 6.23 (s, 1H), 6.44 (m, 1H), 6.99 (m, 1H), 7.18 (m, 2H), 7.82 (m, 1H), 8.15 (m, 1H), 8.57 (d, 2H).

Preparation 18

3-cyano-N-(2,4-dimethoxybenzyl)-4-fluoro-N-(5-fluoropyridin-2-yl)benzenesulfonamide

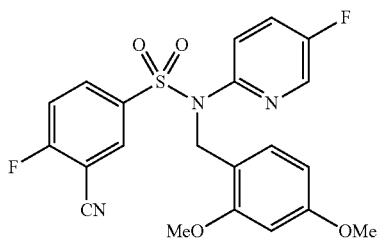 [SMILES: COc1ccc(CN(c2ccc(F)cn2)S(=O)(=O)c2ccc(F)c(C#N)c2)c(OC)c1]

To a −40° C. solution of N-(2,4-dimethoxybenzyl)-5-fluoropyridin-2-amine (Preparation 20, 2.32 g, 8.84 mmol) in THF (60 ml) was added LiHMDS (9.72 ml, 9.72 mmol, 1M in THF) keeping the temperature below −35° C. The reaction mixture was warmed to 0° C. for 40 minutes before re-cooling to −40° C. 3-Cyano-4-fluorobenzene-1-sulfonyl chloride (1.94 g, 8.84 mmol) was added to the reaction mixture as a solution in THF (10 mL) and the reaction mixture allowed to warm to room temperature for 18 hours. The reaction mixture was quenched with saturated ammonium chloride solution (100 mL) and extracted with EtOAc (2×100 mL). The organic layer was washed with saturated brine (100 mL), dried over MgSO$_4$, filtered and the solvent removed under vacuum. The crude material was purified by silica gel column chromatography eluting with 20-40 EtOAc in heptane followed by reverse phase chromatography eluting with 0-100% MeCN in H$_2$O to afford the title compound as a brown gum (2.48 g, 63%).

$^1$H NMR (400 MHz, CDCl$_3$): δ ppm 3.62 (s, 3H), 3.76 (s, 3H), 4.82 (s, 2H), 6.31 (d, 1H), 6.35 (dd, 1H), 7.10 (d, 1H), 7.26-7.41 (m, 3H), 7.95-8.01 (m, 2H), 8.19 (d, 1H).

$^{19}$F NMR (376 MHz, CDCl$_3$): δ ppm −99.36, −127.93

Preparation 19

N-[(2,4-dimethoxyphenyl)methyl]pyridazin-3-amine

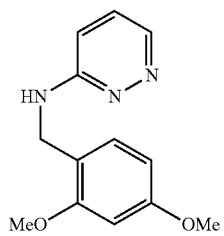 [SMILES: COc1ccc(CNc2cccnn2)c(OC)c1]

To a solution of 3,6-dichloropyridazine (1 g, 6.71 mmol) in "BuOH (25 mL) was added DIPEA (3.31 mL, 18.6 mmol) and 2,4-dimethoxybenzylamine (1.12 g, 6.71 mmol) and the reaction mixture was heated to 100° C. for 18 hours. The reaction mixture was concentrated in vacuo to afford 6-chloro-N-(2,4-dimethoxybenzyl)pyridazin-3-amine.

To a solution of 6-chloro-N-(2,4-dimethoxybenzyl)pyridazin-3-amine (7.5 g, 26.9 mmol) in ethanol (250 mL) was added ammonium formate (5.94 g, 94.15 mmol) and the mixture was degassed with nitrogen three times. Palladium on charcoal (10 wt %, 2.14 g) was added and the mixture was degassed and recharged with nitrogen and stirred at 80° C. for 90 minutes under a nitrogen atmosphere. The mixture was filtered, concentrated to 15 mL and partitioned between DCM (200 mL) and water (150 mL). The organic layer was washed with brine (150 mL) and concentrated in vacuo. The residue was recrystallised from EtOAc to afford the title compound as cream coloured solid (4.5 g, 68%).

$^1$H NMR (400 MHz, CDCl$_3$): δ ppm 3.79 (s, 3H), 3.83 (s, 3H), 4.51 (d, 2H), 5.19 (br s, 1H), 6.43 (dd, 1H), 6.47 (d, 1H), 6.62 (dd, 1H), 7.12 (dd, 1H), 7.24 (d, 1H), 8.52 (d, 1H).

Preparation 20

N-(2,4-dimethoxybenzyl)-5-fluoropyridin-2-amine

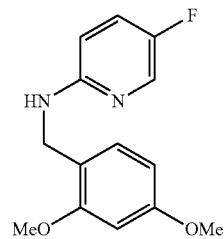 [SMILES: COc1ccc(CNc2ccc(F)cn2)c(OC)c1]

Potassium carbonate (16.75 g, 128.1 mmol) was added to a solution of 2,5-difluoropyridine (4.91 g, 42.7 mmol) and 2,4-dimethoxybenzylamine (6.85 g, 42.7 mmol) in DMSO (30 mL). The mixture was heated to 110° C. for 16 hours, cooled to room temperature and poured into water (100 mL) and ethyl acetate (100 mL). The organic layer was separated and the aqueous layer was extracted with two further portions of ethyl acetate (25 mL). The combined organic extracts were washed with brine (50 mL), dried over MgSO$_4$ and concentrated in vacuo. The residue was purified using silica gel column chromatography eluting with 10 to 30% ethyl acetate in heptanes to afford the title compound as a white solid (2.43 g, 22%).

$^1$H NMR (400 MHz, CDCl$_3$): δ ppm 3.79 (s, 3H), 3.83 (s, 3H), 4.37 (m, 2H), 4.91 (br s, 1H), 6.34-6.44 (m, 3H), 7.17 (m, 2H) 7.94 (s, 1H).

Preparation 21

4-(3-chloro-4-cyanophenoxy)-3-cyanobenzene-1-sulfonyl chloride

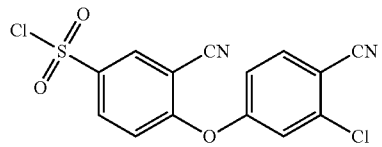 [SMILES: N#Cc1ccc(Oc2ccc(S(=O)(=O)Cl)cc2C#N)cc1Cl]

To a solution of trichloroisocyanuric acid (2.68 g, 11.55 mmol) in acetonitrile (25 ml) was added a solution of benzyltrimethylammonium chloride (6.56 g, 35.28 mmol) in water (11.7 ml) and the mixture was stirred at room temperature for 30 min, then cooled with an ice bath. The mixture was added to an ice cold solution of 4-(4-(benzylthio)-2-cyanophenoxy)-2-chlorobenzonitrile (Preparation 22, 4.61 g, 10.50 mmol) in acetonitrile (50 ml) with 1M sodium carbonate (10.5 ml, 10.5 mmol). The reaction mixture was stirred for 30 minutes at 0° C. The reaction mixture was doubled in volume using ethyl acetate and washed twice with dilute sodium hydrogen carbonate solution (2×200 mL). The organic layer was dried over MgSO$_4$, filtered, and concentrated in vacuo. The residue was purified using silica gel column chromatography eluting with 0% to 20% ethyl acetate in heptanes to afford the title compound as a yellow solid (2.1 g, 46%).

$^1$H NMR (400 MHz, CDCl$_3$): δ ppm 7.13 (d, 1H), 7.19 (d, 1H), 7.36 (s, 1H), 7.83 (d, 1H), 8.22 (d, 1H), 8.41 (s, 1H).

Preparation 22

4-(4-(benzylthio)-2-cyanophenoxy)-2-chlorobenzonitrile

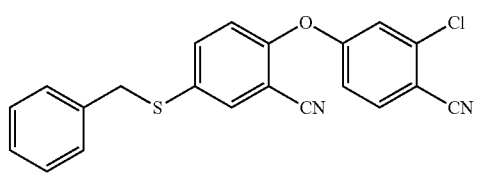 [SMILES: N#Cc1ccc(Oc2ccc(SCc3ccccc3)cc2C#N)cc1Cl]

To a solution of 5-(benzylthio)-2-fluorobenzonitrile (Preparation 23, 6.18 g, 25.4 mmol) in dimethylsulfoxide (64 mL) was added potassium carbonate (10.92 g, 79 mmol) and 2-fluoro-4-hydroxybenzonitrile (6.07 g, 39.5 mmol). The reaction mixture was heated at 80° C. for 18 hours. The reaction mixture was diluted to 500 mL volume with diethyl ether and washed with dilute brine (250 mL), then 2N sodium hydroxide (aq) (2×250 mL) and finally dilute brine (250 mL). The combined organic layers were dried over MgSO$_4$, filtered and the solvent removed in vacuo. The crude material was dissolved in 10% methanol in ethyl acetate, silica (25 g) was added and the mixture evaporated to dryness under vacuum. The resulting solid was purified using silica gel column chromatography eluting with 0% to 100% ethyl acetate in heptanes to furnish the title compound as light brown solid (5.61 g, 51%).

$^1$H NMR (400 MHz, CDCl$_3$): δ ppm 4.14 (s, 2H), 6.98 (d, 2H), 7.17 (s, 1H), 7.22 to 7.38 (m, 5H), 7.46 (d, 1H), 7.58 (s, 1H), 7.65 (d, 1H).

Preparation 23

5-(benzylthio)-2-fluorobenzonitrile

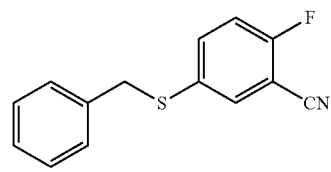 [SMILES: N#Cc1cc(SCc2ccccc2)ccc1F]

To a degassed solution of 5-bromo-2-fluorobenzonitrile (10 g, 50 mmol) in toluene (250 mL) was added N,N-diisopropylethylamine (26 mL, 150 mmol), benzyl mercaptan (5.87 mL, 52 mmol) and dichloro[1,1' bis(di-tert-butylphosphino)]ferrocene palladium (II) (500 mg, 1 mmol). The reaction mixture was heated at 60° C. for 16 hours. The reaction mixture was diluted to 500 mL volume with ethyl acetate and washed with dilute brine (300 mL), then 2N HCl (2×300 mL) and finally dilute brine (300 mL). The combined organic layers were dried over MgSO$_4$, filtered and the solvent removed in vacuo. The residue was purified using silica gel column chromatography eluting with 10% ethyl acetate in heptane to afford the title compound as light brown solid (6.18 g, 51%)

$^1$H NMR (400 MHz, CDCl$_3$): δ ppm 4.04 (s, 2H), 7.08 (t, 1H), 7.40 to 7.55 (m, 5H), 7.43 (m, 2H).

Preparation 24

4-chloro-2-D$_3$-methoxyphenol

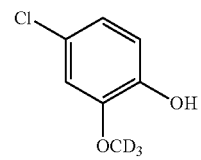

To a solution of 3-D$_3$-methoxy-4-acetylchlorobenzene (Preparation 25, 200 mg, 1.07 mmol) in DCM (10 mL) was added metachloroperbenzoic acid (276 mg, 1.6 mmol) and TFA (200 uL) and the reaction mixture was stirred at reflux for 18 hours. The cooled reaction mixture was poured onto 10% aqueous sodium metabisulphite (100 mL) and extracted with DCM (3×50 mL). The combined organic extracts were washed with saturated aqueous NaHCO$_3$ (3×100 mL), dried over MgSO$_4$ and concentrated in vacuo. The residue was dissolved in THF/water, sodium hydroxide (40 mg, 1 mmol) was added and the reaction stirred at room temperature for 18 hours. The reaction mixture was concentrated in vacuo then partitioned between EtOAc and water. The aqueous layer was collected and acidified with 2N HCl (aq). The compound was extracted from the aqueous phase with EtOAc, dried over MgSO$_4$ and concentrated in vacuo to afford the title compound as an oil (125 mg, 78%), which was used without further purification.

Preparation 25

3-D$_3$-methoxy-4-acetylchlorobenzene

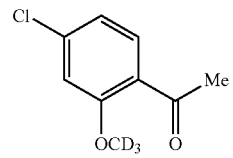

To a solution of 3-chloro-4-acetylphenol (5 g, 5.88 mmol) in DMF (5 mL) was added potassium carbonate (974 mg, 7.05 mmol) followed by CD$_3$I (1.02 g, 7.05 mmol) and the reaction mixture was stirred at 50° C. for 18 hours. The reaction mixture was poured into diethyl ether and washed with water, dried over MgSO$_4$ and concentrated in vacuo to afford the title compound as a pale yellow solid (1.24 g, 94%).

MS m/z 188 [M+H]$^+$

Preparation 26

4-chloro-2-(difluoromethoxy)phenol

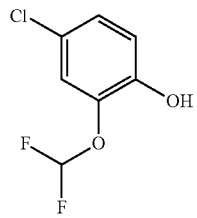 [SMILES: Oc1ccc(Cl)cc1OC(F)F]

To a solution of 4-chloro-2-(difluoromethoxy)bromobenzene (Preparation 27, 200 mg, 0.63 mmol) in THF (6 mL) was added bis-neopentylglycolatodiboron (149 mg, 0.660 mmol), potassium acetate (191 mg, 1.88 mmol) and Pd(dppf)Cl$_2$ (23 mg, 0.031 mmol). The reaction mixture was heated to reflux for 4 hours before cooling and diluting with EtOAc and water. The organic layer was collected, washed with brine, dried over Na$_2$SO$_4$ and concentrated in vacuo. The residue was dissolved in acetone (6 mL) and treated with a solution of oxone (1.64 g, 2.54 mmol) in water (6 mL). The reaction mixture was stirred at room temperature for 15 minutes. The reaction mixture was diluted with diethyl ether (10 mL) and water (5 mL). The organic layer was collected, washed with brine, dried over Na$_2$SO$_4$ and concentrated in vacuo. The residue was purified using silica gel column chromatography eluting with 0-15% diethyl ether in DCM to afford the title compound.

MS m/z 193 [M−H]$^−$

Preparation 27

4-chloro-2-(difluoromethoxy)bromobenzene

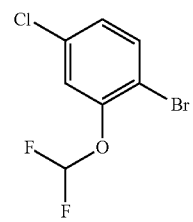

To a solution of 2-bromo-5-chlorophenol (1 g, 4.8 mmol) in DMF/water (45 mL/5 mL) was added sodium chlorodifluoroacetate (1.95 g, 12.0 mmol) and cesium carbonate (3.14 g, 9.64 mmol), and the reaction mixture was heated to 100° C. for 4 hours. The reaction mixture was cooled and diluted with TBME (20 mL) and water (20 mL). The organic layer was collected, washed with saturated aqueous NaHCO$_3$ solution, brine, dried over Na$_2$SO$_4$ and concentrated in vacuo to afford the title compound (1.21 g, 98%), which was used without further purification.

Preparation 28

5-cyano-2-(difluoromethoxy)phenol

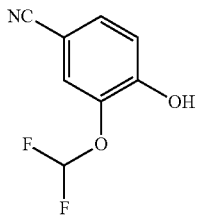

To a solution of trimethylsilylethanol (0.953 mL, 6.68 mmol) in THF (20 mL) was added sodium hydride (267 mg, 6.68 mmol) at 0° C. The reaction mixture was stirred at this temperature for 30 minutes before the addition of 4-cyano-2-(difluoromethoxy)fluorobenzene (Preparation 29, 500 mg, 2.67 mmol). The reaction mixture was stirred at room temperature for 5 hours. The reaction mixture was quenched by the addition of methanol and concentrated in vacuo. The residue was purified using silica gel column chromatography eluting with 10-80% EtOAc in heptanes. The residue was dissolved in THF (6 mL) and TBAF (2 mL) was added. The reaction mixture was stirred at room temperature for 5 hours before the addition of silica gel and concentrating in vacuo. The residue was purified using silica gel column chromatography eluting with 10-100% EtOAc in heptanes to afford the title compound (260 mg, 41%).

MS m/z 184 [M−H]$^−$

Preparation 29

4-cyano-2-(difluoromethoxy)fluorobenzene

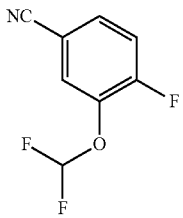 [SMILES: N#Cc1ccc(F)c(OC(F)F)c1]

The title compound was prepared according to the method described for Preparation 27 using 2-fluoro-5-cyanophenol and was used without further purification.

Preparation 30

5-chloro-6-ethoxypyridin-3-ol

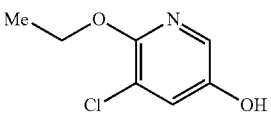 [SMILES: CCOc1ncc(O)cc1Cl]

The title compound was prepared according to the method described for the preparation of 5-chloro-6-(2-methylpropoxy)-3-pyridinol (WO2012007869), using 2-ethoxy-3-chloro-5-hydroxypyridine.

Preparation 31

5-chloro-N-(2,4-dimethoxybenzyl)-2,4-difluoro-N-(pyridazin-3-yl)benzenesulfonamide

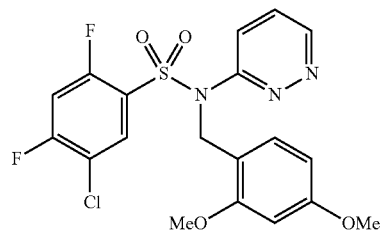 [SMILES: COc1ccc(CN(c2cccnn2)S(=O)(=O)c2cc(Cl)c(F)cc2F)c(OC)c1]

The title compound was prepared according to the method described for Preparation 14 using N-[(2,4-dimethoxyphenyl)methyl]pyridazin-3-amine (Preparation 19) and 2,4-difluoro-5-chlorobenzenesulfonyl chloride.

MS m/z 456 [M+H]$^+$

Preparation 32

3-chloro-N-(2,4-dimethoxybenzyl)-4-fluoro-N-(5-fluoropyridin-2-yl)benzenesulfonamide

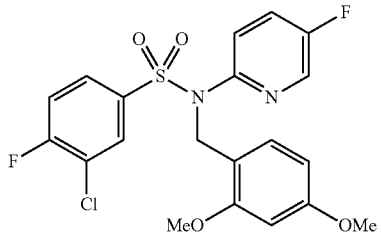 [SMILES: COc1ccc(CN(c2ccc(F)cn2)S(=O)(=O)c2ccc(F)c(Cl)c2)c(OC)c1]

The title compound was prepared according to the method described for Preparation 18 using N-(2,4-dimethoxybenzyl)-5-fluoropyridin-2-amine (Preparation 20) and 4-fluoro-5-chlorobenzenesulfonyl chloride.

$^1$H NMR (400 MHz, CDCl$_3$): δ ppm 3.63 (s, 3H), 3.73 (s, 3H), 4.82 (s, 2H), 6.30-6.34 (m, 2H), 7.11 (d, 1H), 7.20 (t, 1H), 7.29-7.37 (m, 2H), 7.57 (ddd, 1H), 7.75 (dd, 1H), 8.16 (dd, 1H).

$^{19}$F NMR (400 MHz, CDCl$_3$): δ ppm −128.61 (dd, ArF), −107.49 to −107.44 (m, ArF).

Preparation 33

3-bromo-N-(2,4-dimethoxybenzyl)-4-fluoro-N-(5-fluoropyridin-2-yl)benzenesulfonamide

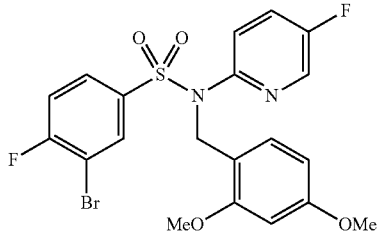 [SMILES: COc1ccc(CN(c2ccc(F)cn2)S(=O)(=O)c2ccc(F)c(Br)c2)c(OC)c1]

The title compound was prepared according to the method described for Preparation 11 using N-(2,4-dimethoxybenzyl)-5-fluoropyridin-2-amine (Preparation 20) and 4-fluoro-5-bromobenzenesulfonyl chloride at 40° C. The residue was purified by silica gel column chromatography eluting with 10% EtOAc in heptanes.

$^1$H NMR (400 MHz, CDCl$_3$): δ ppm 3.63 (s, 3H), 3.73 (s, 3H), 4.82 (s, 2H), 6.30 (d, 1H), 6.32 (dd, 1H), 7.11 (d, 1H), 7.17 (t, 1H), 7.29-7.37 (m, 2H), 7.60-7.63 (m, 1H), 7.89 (dd, 1H), 8.16 (d, 1H).

$^{19}$F NMR (400 MHz, CDCl$_3$): δ ppm −128.63 (dd, ArF), −99.49 to −99.44 (m, ArF).

Preparation 34

N-(2,4-dimethoxybenzyl)-2,4-difluoro-N-(5-fluoropyridin-2-yl)benzenesulfonamide

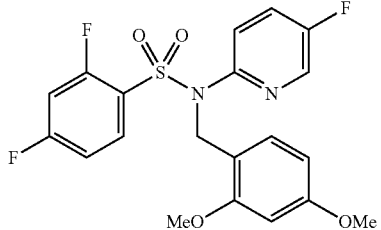 [SMILES: COc1ccc(CN(c2ccc(F)cn2)S(=O)(=O)c2ccc(F)cc2F)c(OC)c1]

The title compound was prepared according to the method described for Preparation 11 using N-(2,4-dimethoxybenzyl)-5-fluoropyridin-2-amine (Preparation 20) and 2,4-difluorobenzene-1-sulfonyl chloride.

$^1$H NMR (400 MHz, CDCl$_3$): δ ppm 3.67 (s, 3H), 3.75 (s, 3H), 4.99 (s, 2H), 6.34 (s, 2H), 6.87-6.97 (m, 2H), 7.16 (d, 1H), 7.29-7.36 (m, 2H), 7.80-7.86 (m, 1H), 8.13 (d, 1H).

Preparation 35

2-((2,4-dimethoxybenzyl)amino)isonicotinonitrile

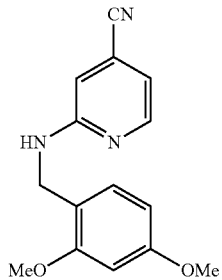 [SMILES: COc1ccc(CNc2cc(C#N)ccn2)c(OC)c1]

The title compound was prepared according to the method described for Preparation 20 using 2,4-dimethoxybenzylamine and 2-fluoroisonicotinonitrile.

$^1$H NMR (400 MHz, CDCl$_3$): δ ppm 3.80 (s, 3H), 3.84 (s, 3H), 4.41 (d, 2H), 5.26 (br s, 1H), 6.44 (dd, 1H), 6.48 (d, 1H), 6.70 (dd, 1H), 7.18 (d, 1H), 8.19 (d, 1H).

MS m/z 270 [M+H]$^+$

Preparation 36

3-cyano-N-(4-cyanopyridin-2-yl)-N-(2,4-dimethoxybenzyl)-4-fluorobenzenesulfonamide

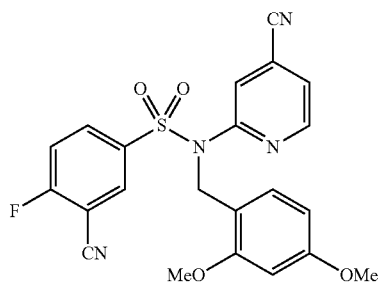 [SMILES: COc1ccc(CN(c2cc(C#N)ccn2)S(=O)(=O)c2ccc(F)c(C#N)c2)c(OC)c1]

The title compound was prepared according to the method described for Preparation 18 using 2-((2,4-dimethoxybenzyl)amino)isonicotinonitrile (Preparation 35) and 3-cyano-4-fluorobenzene-1-sulfonyl chloride. The residue was purified by reverse phase chromatography eluting with 0-100% MeCN in water/0.1% formic acid.

$^1$H NMR (400 MHz, CDCl$_3$): δ ppm 3.60 (s, 3H), 3.78 (s, 3H), 4.96 (s, 2H), 6.32 (d, 1H), 6.39 (dd, 1H), 7.13 (d, 1H), 7.29-7.34 (m, 2H), 7.48 (s, 1H), 8.01 (dd, 1H), 8.05 (m, 1H), 8.50 (d, 1H).

$^{19}$F NMR (376 MHz, CDCl$_3$): δ ppm −98.74.

Preparation 37

6-((2,4-dimethoxybenzyl)amino)nicotinonitrile

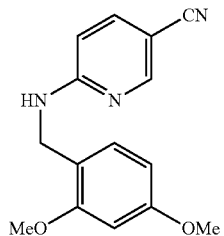 [SMILES: COc1ccc(CNc2ccc(C#N)cn2)c(OC)c1]

The title compound was prepared according to the method described for Preparation 20 using 2,4-dimethoxybenzylamine and 6-fluororonicotinonitrile.

$^1$H NMR (400 MHz, CDCl$_3$): δ ppm 3.80 (s, 3H), 3.84 (s, 3H), 4.47 (d, 2H), 5.47 (br s, 1H), 6.38 (d, 1H), 6.44 (dd, 1H), 6.48 (d, 1H), 7.53 (dd, 1H), 8.36 (d, 1H).

MS m/z 270 [M+H]$^+$

Preparation 38

3-cyano-N-(5-cyanopyridin-2-yl)-N-(2,4-dimethoxybenzyl)-4-fluorobenzenesulfonamide

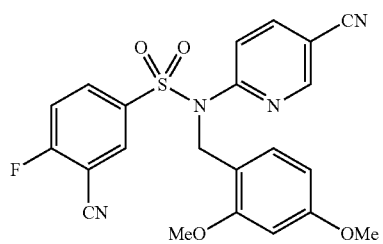

The title compound was prepared according to the method described for Preparation 18 using 6-((2,4-dimethoxybenzyl)amino)nicotinonitrile (Preparation 37) and 3-cyano-4-fluorobenzene-1-sulfonyl chloride. The residue was purified by reverse phase chromatography eluting with 0-100% MeCN in water/0.1% formic acid.

$^1$H NMR (400 MHz, d$_4$-MeOH): δ ppm 3.47 (s, 3H), 3.77 (s, 3H), 5.10 (s, 2H), 6.34 (d, 1H), 6.44 (dd, 1H), 7.14 (d, 1H), 7.45-7.51 (m, 2H), 7.98 (dd, 1H), 8.10 (dd, 1H), 8.24 (m, 1H), 8.68 (d, 1H).

$^{19}$F NMR (376 MHz, CDCl$_3$): δ ppm −102.69.

Preparation 39

3-cyano-4-fluoro-N-(5-chloropyridin-2-yl)benzenesulfonamide

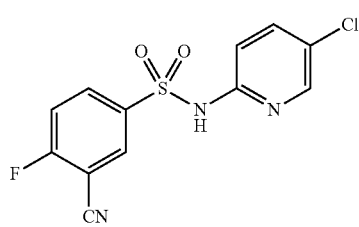 [SMILES: N#Cc1cc(S(=O)(=O)Nc2ccc(Cl)cn2)ccc1F]

The title compound was prepared according to the method described for Preparation 2 using 5-chloropyridin-2-amine.

MS m/z 310 [M−H]$^−$

Preparation 40

3-cyano-4-fluoro-N-(5-methylpyridin-2-yl)benzenesulfonamide

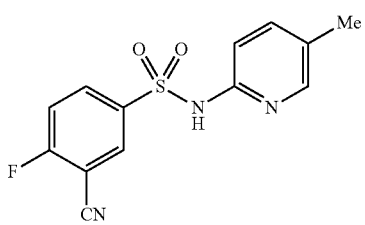 [SMILES: Cc1ccc(NS(=O)(=O)c2ccc(F)c(C#N)c2)nc1]

The title compound was prepared according to the method described for Preparation 2 using 5-methylpyridin-2-amine.

$^1$H NMR (400 MHz, DMSO-d$_6$): δ ppm 2.12 (s, 3H), 5.73 (s, 1H), 7.17 (d, 1H), 7.62-7.66 (m, 2H), 7.79 (br s, 1H), 8.14-8.18 (m, 1H), 8.34 (dd, 1H).

MS m/z 292 [M+H]$^+$

Preparation 41

5-bromo-2-(4-cyano-3-chlorophenoxy)-3-fluorobenzonitrile

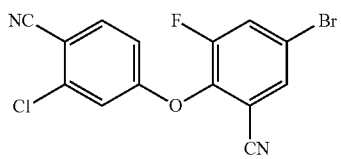 [SMILES: N#Cc1ccc(Oc2c(F)cc(Br)cc2C#N)cc1Cl]

The title compound was prepared according to the method described for Preparation at 120° C. for 68 hours using 5-bromo-3-fluoro-2-hydroxybenzonitrile (WO 2006022374) and 2-chloro-4-fluorobenzonitrile.

$^1$H NMR (400 MHz, CDCl$_3$): δ ppm 6.94 (dd, 1H), 7.06 (d, 1H), 7.65-7.70 (m, 3H).

Preparation 42

5-(benzylthio)-2-(4-cyano-3-chlorophenoxy)-3-fluorobenzonitrile

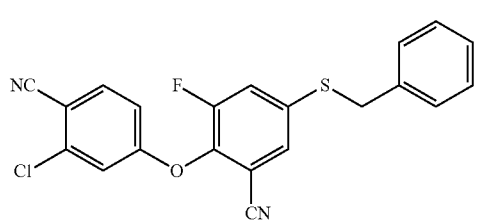 [SMILES: N#Cc1ccc(Oc2c(F)cc(SCc3ccccc3)cc2C#N)cc1Cl]

The title compound was prepared according to the method described for Preparation at reflux using 5-bromo-2-(4-cyano-3-chlorophenoxy)-3-fluorobenzonitrile (Preparation 41) and benzyl mercaptan. The reaction was allowed to cool to room temperature and diluted with EtOAc (100 mL), water (50 mL) and saturated aqueous sodium hydrogen carbonate solution (100 mL). The organic was separated and the aqueous was re-extracted with EtOAc (2×100 mL). The combined organic layers were washed with brine (100 mL), dried over sodium sulfate, filtered and concentrated in vacuo. The residue was absorbed onto silica and purified by silica gel column chromatography eluting with 10% EtOAc in heptanes to afford the title compound as a yellow solid (115 mg, 28%).

$^1$H NMR (400 MHz, CDCl$_3$): δ ppm 4.18 (s, 2H), 6.89 (dd, 1H), 7.00 (d, 1H), 7.29-7.35 (m, 7H), 7.63 (d, 1H).

Preparation 43

3-cyano-4-(4-cyano-3-chlorophenoxy)-5-fluorobenzene-1-sulfonyl chloride

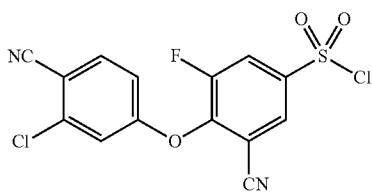 [SMILES: N#Cc1ccc(Oc2c(F)cc(S(=O)(=O)Cl)cc2C#N)cc1Cl]

The title compound was prepared according to the method described for Preparation 21 using 5-(benzylthio)-2-(4-cyano-3-chlorophenoxy)-3-fluorobenzonitrile (Preparation 42).

$^1$H NMR (400 MHz, CDCl$_3$): δ ppm 7.01 (dd, 1H), 7.16 (d, 1H), 7.75 (m, 1H), 8.13 (dd, 1H), 8.23 (m, 1H).

Preparation 44

2-chloro-6-fluoro-4-hydroxybenzonitrile

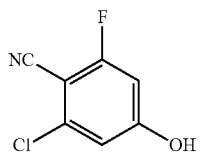 [SMILES: N#Cc1c(F)cc(O)cc1Cl]

A solution of 2-chloro-6-fluoro-4-hydroxybenzaldehyde (WO 2008141249, 90 mg, 0.344 mmol) in formic acid (1 mL) was treated with hydroxylamine hydrochloride (23.9 mg, 0.344 mmol) and sodium formate (23.4 mg, 0.344 mmol) and stirred under nitrogen for 3.5 hours at 105° C. The mixture was concentrated in vacuo and the residue treated with saturated aqueous sodium bicarbonate solution (10 mL). The aqueous solution was extracted with ethyl acetate (2×10 mL), dried over sodium sulphate and concentrated in vacuo. The residue was purified using silica gel column chromatography eluting with 30-50% EtOAc in heptanes to afford the title compound as a beige solid (33 mg, 56%).

$^1$H NMR (400 MHz, MeOH-d$_4$): δ ppm 6.70 (dd, 1H), 6.85 (d, 1H).

Preparation 45

4-(2-hydroxypropan-2-yl)phenol

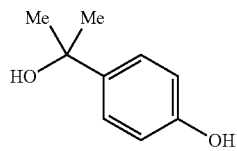

To a solution of 4-acetylphenyl acetate (250 mg, 1.4 mmol) in anhydrous THF (5 mL) cooled to −10° C. under nitrogen was added 3M methylmagnesium chloride solution in THF (2.81 mL, 8.42 mmol) over 10 minutes, keeping the internal temperature below −5° C. The resulting pale yellow solution was allowed to warm to room temperature for 5 hours. The reaction mixture was cooled in an ice bath and quenched with saturated aqueous ammonium chloride solution (20 mL). The resulting clear solution was extracted with EtOAc (2×50 mL). The combined organic extracts were washed with brine (50 mL), dried over MgSO$_4$, filtered and concentrated in vacuo. The solid residue was purified by silica gel column chromatography eluting with 10-50% EtOAc in heptanes to afford the title compound as white solid (100 mg, 47%).

$^1$H NMR (400 MHz, DMSO-d$_6$): δ ppm 1.34 (s, 6H), 4.75 (s, 1H), 6.62 (d, 2H), 7.21 (d, 2H), 9.08 (s, 1H).

Biological Assay

1. Generation of a Custom Clonal Cell Line for URAT1 Transporter Activity Assay The nucleotide sequence for the long isoform of URAT1 (NM_144585) was C-terminally fused to that of enhanced green fluorescent protein (eGFP) (hereinafter referred to as URAT1(L)GFP). The combined sequence was codon-optimised and custom synthesized. The synthesized sequence was generated in pDONR221 Gateway entry vector (Invitrogen Life Technologies) prior to cloning in pLenti6.3/V5 Gateway destination vector (Invitrogen Life Technologies). A schematic of the URAT1(L)GFP construct is set forth in FIG. 1A. The nucleotide and amino acid sequence of the URAT1(L)GFP construct is set out in FIG. 1B, which also shows alignment of the nucleotide sequence with NM_144585.

Lentiviral particles were generated according to ViraPower HiPerform expression system procedure (Invitrogen Life Technologies) and used to transduce CHO cells. Blasticidin selection enabled the generation of a stable clonal pool of cells, confirmed by expression of GFP and V5 epitope. The clonal pools were sorted using fluorescence-activated cell sorting (FACS) on the basis of GFP expression with the gating set at the top 50% of expression into single cells which were subsequently expanded to generate clonal lines. One clone was identified with the best assay performance as determined by maximal separation between complete inhibition of uric acid transport (with 10 μM benzbromarone) and no inhibition (DMSO). This cell line was used for all screening activities and is referred to as CHO-URAT1(L)GFP#8 or CHO#8.

2. URAT-1 Inhibitor Activity

The potency of the compounds of formula (I) as inhibitors of the URAT-1 transporter was determined as follows.

CHO#8 cells were cultured in cell line maintenance flasks in medium consisting of Dulbecco's modified Eagle medium (DMEM) with high glucose and sodium pyruvate (4.5 g of glucose per liter, Invitrogen Life Technologies), supplemented with heat-inactivated foetal bovine serum (FBC, 10% v/v), 1×NEAA (non-essential amino acids) and blasticidin (10 μg/ml). Cultures were grown in 175 cm$^2$ tissue culture flasks in a humidified incubator at approximately 37° C. in approximately 95% air/5% CO$_2$. Near confluent CHO#8 cell cultures were harvested by trypsinisation, re-suspended in culture medium and the process was repeated once or twice weekly to provide sufficient cells for use.

Assay ready flasks were generated by the same method, except the cells were not cultured in blasticidin.

Assay ready frozen cells were generated by freezing 40,000,000 cells in 1 ml of FBS (without blasticidin) containing 10% DMSO per vial. One vial was sufficient for 5 assay plates. Each vial was thawed rapidly to 37° C., washed and re-suspended in pre-warmed culture medium for seeding onto assay plates.

CHO#8 cells were seeded onto Cytostar™ 96-well plates at a density of 5×10$^5$ cells per well. The cells were cultured for 1 day at approximately 37° C. in a humidified incubator containing approximately 5% $CO_2$ in air. After approximately 24 hours culture, cells were used for uptake experiments.

On the day of assay, culture medium was removed from the wells and the cells were washed once with 50 µL of chloride-containing buffer (136.7 mM NaCl, 5.36 mM KCl, 0.952 mM $CaCl_2$, 0.441 mM $KH_2PO_4$, 0.812 mM $MgSO_4$, 5.6 mM D-glucose, 0.383 mM $Na_2HPO_4.2H_2O$, 10 mM HEPES, pH 7.4 with NaOH). The cells were pre-incubated with another 50 µL of chloride-containing buffer for one hour at approximately 37° C. in a humidified incubator containing approximately 5% $CO_2$ in air.

Assay compound plates were prepared by diluting the compounds of formula (I) with chloride-free buffer (125 mM Na-gluconate, 4.8 mM K-gluconate, 1.3 mM Ca-gluconate, 1.2 mM $KH_2PO_4$, 1.2 mM $MgSO_4$, 5.6 mM D-glucose, 25 mM HEPES, pH 7.4 with NaOH) in 100% DMSO to a final concentration of 1% DMSO. [$^{14}$C]-Uric Uric acid working stock was made by addition of radiolabeled compound to a final concentration of 120 nM in chloride-free buffer. In all wells, the final assay concentration of solvent (DMSO) was 0.25%; the final assay concentration of [$^{14}$C]-uric acid was 30 nM in chloride-free buffer and the final compound of formula (I) concentrations ranged from 0 to 10 µM. The vehicle comparator was DMSO (i.e. no inhibition of uric acid transport) and the pharmacological blockade (i.e. 100% inhibition of uric acid transport) was defined by benzbromarone at 10 µM final assay concentration.

After pre-incubation, cells were washed with 50 µL of chloride-free buffer and another 50 µL of chloride-free buffer was added. Thereafter, 25 µL of compound of formula (I) was added from the prepared compound plate and the cells were pre-incubated for 15 minutes prior to the addition of 25 mL of [$^{14}$C] uric acid. The plate was incubated at room temperature and protected from light for three hours prior to measuring proximity-induced scintillation on a Wallac microbeta at 1 minute/well.

The accumulation of [$^{14}$C]-uric acid into CHO#8 cells was calculated and the $IC_{50}$ (µM) values, defined as the concentration of inhibitor required for 50% inhibition of transport, were determined from a 4 parameter logistic fit to generate sigmoid curves from dose response data.

| Ex. | $IC_{50}$ |
|---|---|
| 1 | 0.013 |
| 2 | >10.000 |
| 3 | 0.141 |
| 4 | >10.000 |
| 5 | 0.148 |
| 6 | 0.267 |
| 7 | 0.064 |
| 8 | 0.119 |
| 9 | 0.208 |
| 10 | 0.074 |
| 11 | 0.125 |
| 12 | 0.047 |
| 13 | 0.084 |
| 14 | 0.206 |
| 15 | 0.135 |
| 16 | 0.218 |
| 17 | 0.495 |
| 18 | >10.000 |
| 19 | 0.057 |
| 20 | 0.088 |
| 21 | 0.084 |
| 22 | 0.209 |
| 23 | >10.000 |
| 24 | 0.135 |
| 25 | 0.086 |
| 26 | 0.057 |
| 27 | 0.274 |
| 28 | 0.092 |
| 29 | >10.000 |
| 30 | 0.183 |
| 31 | 0.078 |
| 32 | 0.212 |
| 33 | 0.117 |
| 34 | 0.080 |
| 35 | >10.000 |
| 36 | 0.241 |
| 37 | 0.196 |
| 38 | 0.055 |
| 39 | 0.080 |
| 40 | 0.988 |
| 41 | 0.162 |
| 42 | 0.383 |
| 43 | 0.053 |
| 44 | 0.167 |
| 45 | 0.174 |
| 46 | 0.107 |
| 47 | 0.050 |
| 48 | 0.683 |
| 49 | >1.382 |
| 50 | >10.000 |
| 51 | 0.171 |
| 52 | 0.259 |
| 53 | 0.191 |
| 54 | >10.000 |
| 55 | 0.129 |
| 56 | 0.182 |
| 57 | >10.000 |
| 58 | 0.287 |
| 59 | >10.000 |
| 60 | 0.092 |
| 61 | 0.039 |
| 62 | 0.027 |
| 63 | 0.321 |
| 64 | >1.127 |
| 65 | 0.182 |
| 66 | 0.135 |
| 67 | 3.517 |
| 68 | 0.155 |
| 69 | 1.308 |
| 70 | 0.025 |
| 71 | 0.027 |
| 72 | 0.077 |
| 73 | 0.418 |
| 74 | >10.000 |
| 75 | 2.209 |
| 76 | 0.057 |
| 77 | 0.043 |
| 78 | 0.019 |
| 79 | 0.007 |
| 80 | 0.728 |
| 81 | >10.000 |
| 82 | 0.409 |
| 83 | >5.966 |
| 84 | >8.866 |
| 85 | >10.000 |
| 86 | >5.332 |
| 87 | >7.674 |
| 88 | 0.429 |
| 89 | 0.105 |
| 90 | >3.578 |
| 91 | 1.954 |
| 92 | 0.414 |
| 93 | 2.982 |
| 94 | >10.000 |
| 95 | >10.000 |
| 96 | >10.000 |
| 97 | >1.674 |
| 98 | 3.868 |
| 99 | 0.029 |
| 100 | >10.000 |
| 101 | 0.594 |
| 102 | 3.130 |
| 103 | 0.145 |

| Ex. | IC$_{50}$ |
|---|---|
| 104 | 0.015 |
| 105 | >10.000 |
| 106 | >10.000 |
| 107 | 0.058 |
| 108 | 0.098 |
| 109 | 0.892 |
| 110 | 0.123 |
| 111 | 0.074 |
| 112 | 0.177 |
| 113 | >10.000 |
| 114 | 0.069 |
| 115 | 0.024 |
| 116 | >10.000 |
| 117 | >10.000 |
| 118 | >10.000 |
| 119 | 0.090 |
| 120 | >10.000 |
| 121 | >10.000 |
| 122 | 0.099 |
| 123 | 0.091 |
| 124 | >10.000 |
| 125 | 0.237 |
| 126 | >10.000 |
| 127 | >10.000 |
| 128 | >10.000 |
| 129 | >10.000 |
| 130 | 0.119 |
| 131 | >10.000 |
| 132 | 0.038 |
| 133 | 0.793 |
| 134 | >10.000 |
| 135 | >10.000 |
| 136 | >10.000 |
| 137 | >10.000 |
| 138 | 9.206 |
| 139 | >10.000 |
| 140 | >10.000 |
| 141 | 0.043 |
| 142 | 0.075 |
| 143 | 0.079 |
| 144 | 0.040 |
| 145 | 0.096 |
| 146 | 0.506 |
| 147 | 0.187 |
| 148 | 0.053 |
| 149 | 0.095 |
| 150 | 0.329 |
| 151 | >10.000 |
| 152 | 0.050 |
| 153 | >10.000 |
| 154 | >10.000 |
| 155 | 0.191 |
| 156 | >10.000 |
| 157 | 0.051 |
| 158 | 0.122 |
| 159 | 0.514 |
| 160 | >10.000 |
| 161 | >10.000 |
| 162 | 0.125 |
| 163 | >10.000 |
| 164 | 6.163 |
| 165 | 0.139 |
| 166 | 0.116 |
| 167 | 0.050 |
| 168 | 0.612 |
| 169 | 0.134 |
| 170 | 0.570 |
| 171 | 0.215 |
| 172 | 0.502 |
| 173 | 0.131 |
| 174 | >10.000 |
| 175 | 0.455 |
| 176 | 1.020 |
| 177 | 0.246 |
| 178 | >10.000 |
| 179 | >0.728 |
| 180 | 0.877 |
| 181 | >10.000 |
| 182 | 0.175 |
| 183 | 0.183 |
| 184 | 0.385 |
| 185 | NT |
| 186 | 0.324 |
| 187 | >10.000 |
| 188 | 3.743 |
| 189 | 0.103 |
| 190 | >10.000 |
| 191 | 1.993 |
| 192 | NT |
| 193 | NT |
| 194 | >10.000 |
| 195 | NT |
| 196 | >10.000 |
| 197 | >10.000 |
| 198 | 0.792 |
| 199 | 0.129 |
| 200 | 0.053 |
| 201 | 0.074 |
| 202 | 0.037 |
| 203 | 0.037 |
| 204 | >10.000 |
| 205 | 2.628 |
| 206 | 1.084 |
| 207 | >10.000 |
| 208 | >10.000 |
| 209 | >10.000 |
| 210 | >10.000 |
| 211 | >2.998 |
| 212 | >10.000 |
| 213 |  |
| 214 | >1.153 |
| 215 | >10.000 |
| 216 | >10.000 |
| 217 | >10.000 |
| 218 | >10.000 |
| 219 | >10.000 |
| 220 | >10.000 |
| 221 | >10.000 |
| 222 | >10.000 |
| 223 | >10.000 |
| 224 | >10.000 |
| 225 | 2.331 |
| 226 | 1.779 |
| 227 | >10.000 |
| 228 | 0.244 |
| 229 | 0.126 |
| 230 | 0.062 |
| 231 | 0.053 |
| 232 | 0.012 |
| 233 | 0.233 |
| 234 | 1.150 |
| 235 | 0.013 |
| 236 | NT |
| 237 | 0.008 |
| 238 | 0.088 |
| 239 | 0.002 |
| 240 | 0.106 |
| 241 | 0.003 |
| 242 | NT |
| 243 | 1.000 |
| 244 | 0.258 |
| 245 | 0.472 |
| 246 | 0.087 |
| 247 | 0.001 |
| 248 | 0.324 |
| 249 | 0.021 | nT = Not Tested

The invention claimed is:

1. A compound of formula (I):

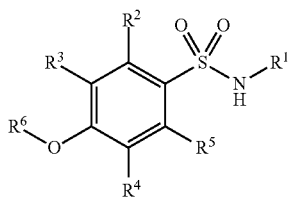

or a pharmaceutically acceptable salt thereof, wherein $R^1$ is a 'C-linked' 6-membered heteroaryl containing one, two or three nitrogen atoms wherein said heteroaryl is optionally substituted by one, two or, three valency permitting, $X^1$;

each $X^1$ is independently selected from: F; Cl; CN; ($C_1$-$C_4$)alkyl optionally substituted by one, two or three F; or ($C_1$-$C_4$)alkyloxy optionally substituted by one two or three F;

$R^2$, $R^3$ and $R^5$ are independently selected from: H; halogen; CN; ($C_1$-$C_4$)alkyl optionally substituted by one, two or three F; or ($C_1$-$C_4$)alkyloxy optionally substituted by one, two or three F;

$R^4$ is selected from: halogen; CN; ($C_1$-$C_4$)alkyl optionally substituted by one, two or three F; or ($C_1$-$C_4$)alkyloxy optionally substituted by one, two or three F;

$R^6$ is phenyl substituted by one, two or three $X^2$; or a 'C-linked' 6-membered heteroaryl containing one or two nitrogen atoms wherein said heteroaryl is optionally substituted by one, two or three $X^2$;

each $X^2$ is independently selected from: F; Cl; CN; —S($C_1$-$C_4$)alkyl; —$NR^7R^8$; ($C_1$-$C_6$)alkyloxy optionally substituted by one, two or three F; ($C_3$-$C_6$)cycloalkyloxy; ($C_1$-$C_6$)alkyl optionally substituted by one, two or three F; or ($C_1$-$C_6$)alkyl substituted by OH; and $R^7$ and $R^8$ are independently H or ($C_1$-$C_4$)alkyl or, together with the nitrogen atom to which they are attached, form a saturated 4- to 6-membered nitrogen containing monocycle.

2. The compound according to claim 1 or a pharmaceutically acceptable salt thereof, wherein $R^1$ is a 'C-linked' 6-membered heteroaryl containing one or two nitrogen atoms, wherein said heteroaryl is optionally substituted by one or two $X^1$.

3. The compound according to claim 2 or a pharmaceutically acceptable salt thereof, wherein said heteroaryl is optionally substituted by $X^1$.

4. The compound according to claim 1 or a pharmaceutically acceptable salt thereof, wherein $R^1$ is a 'C-linked' pyridinyl optionally substituted by $X^1$.

5. The compound according to claim 1 or a pharmaceutically acceptable salt thereof, wherein $R^1$ is a 'C-linked' pyridinyl substituted by $X^1$.

6. The compound according to claim 1 or a pharmaceutically acceptable salt thereof, wherein $X^1$ is F.

7. The compound according to claim 1 or a pharmaceutically acceptable salt thereof, wherein $R^4$ is either halogen or CN, and $R^2$, $R^3$ and $R^5$ are independently selected from: H; halogen; or CN.

8. The compound according to claim 1 or a pharmaceutically acceptable salt thereof, wherein $R^4$ is CN; and each of $R^2$, $R^3$ and $R^5$ are H.

9. The compound according to claim 1 or a pharmaceutically acceptable salt thereof, wherein $R^6$ is phenyl substituted by one, two or three $X^2$.

10. The compound according to claim 1 or a pharmaceutically acceptable salt thereof, wherein $R^6$ is a 'C-linked' 6-membered heteroaryl containing one or two nitrogen atoms, wherein said heteroaryl is optionally substituted by one, two or three $X^2$.

11. The compound according to claim 1 or a pharmaceutically acceptable salt thereof, wherein each $X^2$ is independently selected from: F; Cl; CN; —S($C_1$-$C_3$)alkyl; ($C_1$-$C_4$) alkyloxy optionally substituted by one, two or three F; or ($C_1$-$C_4$)alkyl optionally substituted by one, two or three F.

12. The compound according to claim 1 or a pharmaceutically acceptable salt thereof, wherein each $X^2$ is independently selected from: F; Cl; CN; methoxy; or methyl.

13. A pharmaceutical composition comprising a compound according to claim 1 or a pharmaceutically acceptable salt thereof, and a pharmaceutically acceptable excipient.

14. The pharmaceutical composition according to claim 13, wherein said composition further comprises one or more additional therapeutic agents.

15. A method of inhibiting URAT-1 in a human or animal in need thereof comprising administering to said human or animal a therapeutically effective amount of a compound according to claim 1 or a pharmaceutically acceptable salt thereof.

16. The method of claim 15 wherein the inhibition of URAT-1 is a human or animal is for the treatment of gout.

* * * * *

SEQUENCE LISTING

<160> NUMBER OF SEQ ID NOS: 3

<210> SEQ ID NO 1
<211> LENGTH: 1692
<212> TYPE: DNA
<213> ORGANISM: Homo sapiens

<400> SEQUENCE: 1

```
gggcccctct tctgggcccc ttgagtaggt tccatggcat tttctgaact cctggacctc    60
gtgggtggcc tgggcaggtt ccaggttctc cagacgatgg ctctgatggt ctccatcatg   120
tggctgtgta cccagagcat gctggagaac ttctcggccg ccgtgcccag ccaccgctgc   180
tgggcacccc tcctggacaa cagcacggct caggccagca tcctagggag cttgagtcct   240
gaggccctcc tggctatttc catcccgccg ggccccaacc agaggcccca ccagtgccgc   300
cgcttccgcc agccacagtg gcagctcttg gaccccaatg ccacggccac cagctggagc   360
gaggccgaca cggagccgtg tgtggatggc tgggtctatg accgcagcat cttcacctcc   420
acaatcgtgg ccaagtggaa cctcgtgtgt gactctcatg ctctgaagcc catggcccag   480
tccatctacc tggctgggat tctggtggga gctgctgcgt gcggccctgc ctcagacagg   540
tttgggcgca ggctggtgct aacctggagc taccttcaga tggctgtgat gggtacggca   600
gctgccttcg cccctgcctt ccccgtgtac tgcctgttcc gcttcctgtt ggcctttgcc   660
gtggcaggcg tcatgatgaa cacgggcact ctcctgatgg agtggacggc ggcacgggcc   720
cgacccttgg tgatgacctt gaactctctg ggcttcagct tcggccatgg cctgacagct   780
gcagtggcct acggtgtgcg ggactggaca ctgctgcagc tggtggtctc ggtcccttc    840 ttcctctgct ttttgtactc ctggtggctg gcagagtcgg cacgatggct cctcaccaca   900
ggcaggctgg attgggggcct gcaggagctg tggagggtgg ctgccatcaa cggaaagggg   960
gcagtgcagg acaccctgac ccctgaggtc ttgctttcag ccatgcggga ggagctgagc  1020
atgggccagc tcctgccagc ctgggcacc ctgctccgca tgcccggact gcgcttccgg   1080
acctgtatct ccacgttgtg ctggttcgcc tttggcttca ccttcttcgg cctggccctg   1140
gacctgcagg ccctgggcag caacatcttc ctgctccaaa tgttcattgg tgtcgtggac   1200
atcccagcca agatgggcgc cctgctgctg ctgagccacc tgggccgccg ccccacgctg   1260
gccgcatccc tgttgctggc agggctctgc attctggcca acacgctggt gccccacgaa   1320
atgggggctc tgcgctcagc cttggccgtg ctggggctgg gcggggtggg ggctgccttc   1380
acctgcatca ccatctacag cagcgagctc ttccccactg tgctcaggat gacggcagtg   1440
ggcttgggcc agatggcagc ccgtggagga gccatcctgg ggcctctggt ccggctgctg   1500
ggtgtccatg gccctggct gcccttgctg gtgtatggga cggtgccagt gctgagtggc  1560
ctggccgcac tgcttctgcc cgagacccag agcttgccgc tgcccgacac catccaagat   1620
gtgcagaacc aggcagtaaa gaaggcaaca catggcacgc tggggaactc tgtcctaaaa   1680
tccacacagt tt                                                       1692
```

<210> SEQ ID NO 2
<211> LENGTH: 2546
<212> TYPE: DNA
<213> ORGANISM: Artificial Sequence
<220> FEATURE:
<223> OTHER INFORMATION: Primer

```
<400> SEQUENCE: 2
acaagtttgt acaaaaaaga ggcttcgcca ccatggcctt cagcgagctg ctggacctgg      60
tgggaggcct gggcagattc caggtgctgc agaccatggc cctgatggtg tccatcatgt     120
ggctgtgcac ccagagcatg ctggaaaact tctctgccgc cgtgcccagc cacagatgct     180
gggcccctct gctggacaac agcaccgccc aggccagcat cctgggcagc ctgtctccag     240
aggccctgct ggccatcagc atccccctg gccccaacca gaggccccac cagtgcagac      300
ggttccggca gcctcagtgg cagctgctgg atccaacgc caccgccacc tcttggagcg      360
aggccgacac cgagccctgt gtggacggct gggtgtacga ccgtccatc ttcaccagca      420 ccatcgtggc caagtggaac ctggtgtgcg acagtcacgc cctgaagccc atggcccaga     480
gcatctacct ggccggcatt ctggtgggag ccgccgcttg tggccctgcc agcgatagat     540
tcggcagacg gctggtgctg acctggtcct acctgcagat ggccgtgatg ggcaccgccg     600
cagcctttgc ccctgccttc cctgtgtact gcctgttccg gttcctgctg gccttcgccg     660
tggccggcgt gatgatgaac accggcaccc tgctgatgga atggaccgcc gccagagcca     720 gaccctggt gatgaccctg aacagcctgg gcttcagctt cggacatggc ctcacagccg      780
ctgtggctta tggcgtgcgg gactggacac tgctgcagct ggtggtgtcc gtgcccttct     840
tcctgtgctt cctgtacagc tggtggctcc gctgagagcgc ccggtggctg ctgaccacag    900
gcagactgga ctggggcctg caggaactgt ggcgggtcgc cgccatcaat ggcaagggcg     960
ccgtgcagga caccctgacc cctgaggtgc tgctgagcgc catgcgcgag gaactgagca    1020
tgggccagcc tccagccagc ctgggcacac tgctgagaat gccgcgcctg cggttccgga   1080
cctgcatcag caccctgtgt tggttcgcct tcggcttcac cttcttcggc ctggccctgg   1140
acctccaggc cctgggcagc aacatcttcc tgctgcagat gttcatcggc gtggtggaca   1200
tccccgccaa gatgggcgcc ctgctgctgc tgtctcacct gggcagaagg cctaccctgg   1260
ccgcctctct gctgctggcc ggactgtgca tcctggccaa cacccctgtg ccccacgaga   1320
tgggagccct gagatctgcc ctggccgtcc tgggactggg aggcgtggga gctgccttca   1380
cctgtatcac catctacagc agcgagctgt tccccaccgt gctgcggatg acagccgtgg   1440
gcctgggaca gatggccgcc agaggcggag ccatcctggg acctctggtg cgcctgctgg   1500
gagtgcacgg accttggctc cctctgctgg tgtacggcac cgtgcctgtg ctgtctggac   1560
tggctgctct gctgctgccc gagacacaga gcctgccct gcccgacacc atccaggacg    1620
tgcagaacca ggccgtgaag aaggccacc acggcaccct gggcaacagc gtgctgaagt   1680
ccacccagtt catggtgtcc aagggggagg aactgtttac cggcgtggtg cccatcctgg   1740
tggaactgga cggcgacgtg aacgccaca agttcagcgt gtccggcgag ggcgaaggcg    1800
acgccaccta cggcaagctg accctgaagt tcatctgcac caccggcaag ctgcccgtgc   1860
cttggcccac cctggtgaca accttcacct acggcgtgca gtgcttcgcc agataccccg   1920
accacatgaa gcagcacgat ttcttcaagt ccgccatgcc cgagggctac gtgcaggaac   1980
ggaccatctt cttcaaggac gacggcaact acaagaccag agccgaagtg aagttcgagg   2040
gcgataccct ggtgaaccgg atcgagctga agggcatcga cttcaaagag gacggcaata   2100
tcctgggcca caagctggag tacaactaca acagccacaa ggtgtacatc accgccgaca   2160
agcagaaaaa cggcatcaaa gtgaacttca gaccccggca aacatcgag gacggaagcg     2220 tgcagctggc cgaccactac cagcagaaca ccccatcgg cgacggcccc gtgctgctgc     2280
ctgacaacca ctacctgagc acccagtccg ccctgagcaa ggaccccaac gagaagcggg   2340
```

-continued

```
accacatggt gctgctggaa ttcgtgaccg ccgctggcat cacactgggc atggacgagc    2400
tgtacaagta cccagctttc ttgtacaaag tggttgatat ccagcacagt ggcggccgct    2460
cgagtctaga gggcccgcgg ttcgaaggta agcctatccc taaccctctc ctcggtctcg    2520
attctacgcg taccggttag taatga                                         2546
```

<210> SEQ ID NO 3
<211> LENGTH: 835
<212> TYPE: PRT
<213> ORGANISM: Homo sapiens

<400> SEQUENCE: 3

```
Met Ala Phe Ser Glu Leu Leu Asp Leu Val Gly Gly Leu Gly Arg Phe
1               5                   10                  15

Gln Val Leu Gln Thr Met Ala Leu Met Val Ser Ile Met Trp Leu Cys
            20                  25                  30

Thr Gln Ser Met Leu Glu Asn Phe Ser Ala Ala Val Pro Ser His Arg
        35                  40                  45

Cys Trp Ala Pro Leu Leu Asp Asn Ser Thr Ala Gln Ala Ser Ile Leu
    50                  55                  60

Gly Ser Leu Ser Pro Glu Ala Leu Leu Ala Ile Ser Ile Pro Pro Gly
65                  70                  75                  80

Pro Asn Gln Arg Pro His Gln Cys Arg Arg Phe Arg Gln Pro Gln Trp
                85                  90                  95

Gln Leu Leu Asp Pro Asn Ala Thr Ala Thr Ser Trp Ser Glu Ala Asp
            100                 105                 110

Thr Glu Pro Cys Val Asp Gly Trp Val Tyr Asp Arg Ser Ile Phe Thr
        115                 120                 125

Ser Thr Ile Val Ala Lys Trp Asn Leu Val Cys Asp Ser His Ala Leu
    130                 135                 140

Lys Pro Met Ala Gln Ser Ile Tyr Leu Ala Gly Ile Leu Val Gly Ala
145                 150                 155                 160

Ala Ala Cys Gly Pro Ala Ser Asp Arg Phe Gly Arg Arg Leu Val Leu
                165                 170                 175

Thr Trp Ser Tyr Leu Gln Met Ala Val Met Gly Thr Ala Ala Ala Phe
            180                 185                 190

Ala Pro Ala Phe Pro Val Tyr Cys Leu Phe Arg Phe Leu Leu Ala Phe
        195                 200                 205

Ala Val Ala Gly Val Met Met Asn Thr Gly Thr Leu Leu Met Glu Trp
    210                 215                 220

Thr Ala Ala Arg Ala Arg Pro Leu Val Met Thr Leu Asn Ser Leu Gly
225                 230                 235                 240

Phe Ser Phe Gly His Gly Leu Thr Ala Ala Val Ala Tyr Gly Val Arg
                245                 250                 255

Asp Trp Thr Leu Leu Gln Leu Val Val Ser Val Pro Phe Phe Leu Cys
            260                 265                 270

Phe Leu Tyr Ser Trp Trp Leu Ala Glu Ser Ala Arg Trp Leu Leu Thr
        275                 280                 285

Thr Gly Arg Leu Asp Trp Gly Leu Gln Glu Leu Trp Arg Val Ala Ala
    290                 295                 300

Ile Asn Gly Lys Gly Ala Val Gln Asp Thr Leu Thr Pro Glu Val Leu
305                 310                 315                 320

Leu Ser Ala Met Arg Glu Glu Leu Ser Met Gly Gln Pro Pro Ala Ser
                325                 330                 335
```

-continued

```
Leu Gly Thr Leu Leu Arg Met Pro Gly Leu Arg Phe Arg Thr Cys Ile
            340                 345                 350

Ser Thr Leu Cys Trp Phe Ala Phe Gly Phe Thr Phe Phe Gly Leu Ala
        355                 360                 365

Leu Asp Leu Gln Ala Leu Gly Ser Asn Ile Phe Leu Leu Gln Met Phe
    370                 375                 380

Ile Gly Val Val Asp Ile Pro Ala Lys Met Gly Ala Leu Leu Leu Leu
385                 390                 395                 400

Ser His Leu Gly Arg Arg Pro Thr Leu Ala Ala Ser Leu Leu Leu Ala
                405                 410                 415

Gly Leu Cys Ile Leu Ala Asn Thr Leu Val Pro His Glu Met Gly Ala
            420                 425                 430

Leu Arg Ser Ala Leu Ala Val Leu Gly Leu Gly Val Gly Ala Ala
        435                 440                 445

Phe Thr Cys Ile Thr Ile Tyr Ser Ser Glu Leu Phe Pro Thr Val Leu
    450                 455                 460

Arg Met Thr Ala Val Gly Leu Gly Gln Met Ala Ala Arg Gly Gly Ala
465                 470                 475                 480

Ile Leu Gly Pro Leu Val Arg Leu Leu Gly Val His Gly Pro Trp Leu
                485                 490                 495

Pro Leu Leu Val Tyr Gly Thr Val Pro Val Leu Ser Gly Leu Ala Ala
            500                 505                 510

Leu Leu Leu Pro Glu Thr Gln Ser Leu Pro Leu Pro Asp Thr Ile Gln
        515                 520                 525

Asp Val Gln Asn Gln Ala Val Lys Lys Ala Thr His Gly Thr Leu Gly
    530                 535                 540

Asn Ser Val Leu Lys Ser Thr Gln Phe Met Val Ser Lys Gly Glu Glu
545                 550                 555                 560

Leu Phe Thr Gly Val Val Pro Ile Leu Val Glu Leu Asp Gly Asp Val
                565                 570                 575

Asn Gly His Lys Phe Ser Val Ser Gly Glu Gly Glu Gly Asp Ala Thr
            580                 585                 590

Tyr Gly Lys Leu Thr Leu Lys Phe Ile Cys Thr Thr Gly Lys Leu Pro
        595                 600                 605

Val Pro Trp Pro Thr Leu Val Thr Thr Phe Thr Tyr Gly Val Gln Cys
    610                 615                 620

Phe Ala Arg Tyr Pro Asp His Met Lys Gln His Asp Phe Phe Lys Ser
625                 630                 635                 640

Ala Met Pro Glu Gly Tyr Val Gln Glu Arg Thr Ile Phe Phe Lys Asp
                645                 650                 655

Asp Gly Asn Tyr Lys Thr Arg Ala Glu Val Lys Phe Glu Gly Asp Thr
            660                 665                 670

Leu Val Asn Arg Ile Glu Leu Lys Gly Ile Asp Phe Lys Glu Asp Gly
        675                 680                 685

Asn Ile Leu Gly His Lys Leu Glu Tyr Asn Tyr Asn Ser His Lys Val
    690                 695                 700

Tyr Ile Thr Ala Asp Lys Gln Lys Asn Gly Ile Lys Val Asn Phe Lys
705                 710                 715                 720

Thr Arg His Asn Ile Glu Asp Gly Ser Val Gln Leu Ala Asp His Tyr
                725                 730                 735

Gln Gln Asn Thr Pro Ile Gly Asp Gly Pro Val Leu Leu Pro Asp Asn
            740                 745                 750
```

```
His Tyr Leu Ser Thr Gln Ser Ala Leu Ser Lys Asp Pro Asn Glu Lys
        755                 760                 765

Arg Asp His Met Val Leu Leu Glu Phe Val Thr Ala Ala Gly Ile Thr
    770                 775                 780

Leu Gly Met Asp Glu Leu Tyr Lys Ile Pro Ala Phe Leu Tyr Lys Val
785                 790                 795                 800

Val Asn Ile Gln His Ser Gly Gly Arg Ser Ser Leu Glu Gly Pro Arg
                805                 810                 815

Phe Glu Gly Lys Pro Ile Pro Asn Pro Leu Leu Gly Leu Asp Ser Thr
            820                 825                 830

Arg Thr Gly
        835
```